US012560595B2

(12) United States Patent
Juncker et al.

(10) Patent No.: US 12,560,595 B2
(45) Date of Patent: Feb. 24, 2026

(54) COLOCALIZATION-BY-LINKAGE SANDWICH ASSAYS FOR MULTIPLEXING

(71) Applicant: NOMIC BIO INC., Montréal (CA)

(72) Inventors: David Juncker, Verdun (CA); Milad Dagher, Montréal (CA)

(73) Assignee: NOMIC BIO INC., Montreal (CA)

( * ) Notice: Subject to any disclaimer, the term of this patent is extended or adjusted under 35 U.S.C. 154(b) by 804 days.

(21) Appl. No.: 17/711,731

(22) Filed: Apr. 1, 2022

(65) Prior Publication Data

US 2023/0090326 A1     Mar. 23, 2023

Related U.S. Application Data

(63) Continuation of application No. PCT/IB2020/000813, filed on Oct. 2, 2020.

(60) Provisional application No. 62/909,701, filed on Oct. 2, 2019.

(51) Int. Cl.
| | |
|---|---|
| *C12Q 1/68* | (2018.01) |
| *C12Q 1/6804* | (2018.01) |
| *G01N 33/53* | (2006.01) |
| *G01N 33/543* | (2006.01) |

(52) U.S. Cl.
CPC ....... *G01N 33/5308* (2013.01); *C12Q 1/6804* (2013.01); *G01N 33/54306* (2013.01); *C12Q 2537/143* (2013.01); *G01N 2400/00* (2013.01); *G01N 2458/00* (2013.01); *G01N 2458/10* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,945,042 A | 7/1990 | Geiger et al. | |
| 4,965,188 A | 10/1990 | Mullis et al. | |
| 5,168,038 A | 12/1992 | Tecott et al. | |
| 5,210,015 A | 5/1993 | Gelfand et al. | |
| 5,399,491 A | 3/1995 | Kacian et al. | |
| 5,539,082 A | 7/1996 | Nielsen et al. | |
| 5,695,926 A | 12/1997 | Cros et al. | |
| 5,854,033 A | 12/1998 | Lizardi | |
| 5,925,517 A | 7/1999 | Tyagi et al. | |
| 6,174,670 B1 | 1/2001 | Wittwer et al. | |
| 6,569,627 B2 | 5/2003 | Wittwer et al. | |
| 6,670,461 B1 | 12/2003 | Wengel et al. | |
| 7,306,904 B2 | 12/2007 | Landegren et al. | |
| 8,268,554 B2 | 9/2012 | Schallmeiner | |
| 9,481,945 B2 | 11/2016 | Juncker et al. | |
| 11,493,505 B2 * | 11/2022 | Juncker .............. | G01N 33/5308 |
| 2003/0092901 A1 | 5/2003 | Farooqui et al. | |
| 2007/0009914 A1 | 1/2007 | Wallace et al. | |
| 2016/0153973 A1 | 6/2016 | Smith | |
| 2019/0237166 A1 | 8/2019 | Juncker et al. | |
| 2020/0319173 A1 | 10/2020 | Juncker et al. | |
| 2021/0278398 A1 | 9/2021 | Luo et al. | |
| 2021/0285937 A1 | 9/2021 | Dagher et al. | |
| 2023/0111239 A1 * | 4/2023 | Juncker .............. | G01N 33/5308 |
| | | | 435/61 |
| 2023/0116205 A1 | 4/2023 | Dagher et al. | |

FOREIGN PATENT DOCUMENTS

| | | | | |
|---|---|---|---|---|
| CA | 2948547 A1 | 11/2015 | | |
| CN | 1902496 A | 1/2007 | | |
| CN | 101374965 A | 2/2009 | | |
| CN | 102549170 A | 7/2012 | | |
| CN | 104245960 A | 12/2014 | | |
| CN | 104812915 A | 7/2015 | | |
| CN | 112236527 A | 1/2021 | | |
| EP | 0168689 A2 | 1/1986 | | |
| EP | 0168689 B1 | 9/1990 | | |
| EP | 0703296 A1 | 3/1996 | | |
| EP | 1767937 A1 | 3/2007 | | |
| EP | 3102698 B1 | 1/2019 | | |
| JP | H04262799 A | 9/1992 | | |
| WO | WO-2004042030 A2 | 5/2004 | | |
| WO | WO-2007044903 A2 | 4/2007 | | |
| WO | WO-2015006503 A1 | 1/2015 | | |
| WO | WO-2018058073 A2 | 3/2018 | | |
| WO | WO-2019191838 A1 * | 10/2019 | ....... | G01N 33/54306 |
| WO | WO-2019222708 A2 | 11/2019 | | |
| WO | WO-2021064460 A1 * | 4/2021 | ....... | G01N 33/54306 |
| WO | WO-2021181161 A1 | 9/2021 | | |

OTHER PUBLICATIONS

Becker-Andre, et al. Absolute mRNA quantification using the polymerase chain reaction (PCR). A novel approach by a PCR aided transcript titration assay (PATTY). Nucleic Acids Res. Nov. 25, 1989;17(22):9437-46.

Bernard et al., Color multiplexing hybridization probes using the apolipoprotein E locus as a model system for genotyping. Anal Biochem 273(2):221-228 (1999).

Blank et al., Double-chip protein arrays: force-based multiplex sandwich immunoassays with increased specificity. Analytical and bioanalytical chemistry 379(7): 974-981 (2004).

Boyle, M. Bacterial Immunoglobulin-Binding Proteins: Applications in Immunotechnology. Academic press (2014).

(Continued)

*Primary Examiner* — Gary Benzion
*Assistant Examiner* — Olayinka A Oyeyemi
(74) *Attorney, Agent, or Firm* — Wilson Sonsini Goodrich & Rosati

(57) ABSTRACT

There are provided methods and systems for detecting and/or quantifying an analyte. In particular, there are provided methods and systems for simultaneous detection and/or quantitation of two or more analytes in a sample. Colocalization-by-linkage assays on microparticles (CLAMP) can be engineered and used to effectively multiplex the detection of analytes within a sample. Features and methods of CLAMP systems can provide robust and scalable analysis of analytes in a sample.

11 Claims, 30 Drawing Sheets

Specification includes a Sequence Listing.

(56) References Cited

OTHER PUBLICATIONS

Bunt, G. et al., "FRET from single to multiplexed signaling events", Biophys Rev, 2017, vol. 9, pp. 119-129.

Corry, B. et al., "A Flexible Approach to the Calculation of Resonance Energy Transfer Efficiency between Multiple Donors and Acceptors in Complex Geometries", Biophysical Journal, 2005, vol. 89, pp. 3822-3836.

Dagher et al., Ensemble multicolour FRET model enables barcoding at extreme FRET levels. Nature Nanotechnology 13: 925-932 (2018).

Dagher et al., One-pot microsphere barcoding using fluorescent oligonucleotides. Biomedical Engineering Department and Genome Quebec, McGill University (2016).

Dagher, M. Scalable affinity-proteomics on microparticles. Chapter IV (2019).

Diviacco et al., A novel procedure for quantitative polymerase chain reaction by coamplification of competitive templates. Gene 122(2):313-320 (1992).

Extended European Search Report dated Nov. 11, 2021 for European Application No. 19781762.0.

Freeman, et al. Quantitative RT-PCR: pitfalls and potential. Biotechniques. Jan. 1999;26(1):112-126.

Fu et al., Multiplex Assays for Biomarker Research and Clinical Application: Translational Science Coming of Age. Proteomics Clin Appl. 4(3):271-284 (2010).

Galperin et al., Three-chromophore FRET microscopy to analyze multiprotein interactions in living cells. Nature Methods 1(3): 209-217 (2004).

Gerver et al., Programmable microfluidic synthesis of spectrally encoded microspheres. Lab on a Chip 12(22): 4716 (2012).

Huiyan, Novel antibody microarray technologies for multiplex protein analysis in complex samples. Doctor of Philosophy Department of Biomedical Engineering, McGill University. Montreal, Quebec, Canada (2014). 180 pages.

Indian Patent Application No. 202017043052 Office Action dated Apr. 22, 2022.

Jani et al., Multiplexed immunoassays by flow cytometry for diagnosis and surveillance of infectious diseases in resource-poor settings. The Lancet 2(4): 243-250 (2002).

Juncker et al., Cross-reactivity in antibody microarrays and multiplexed sandwich assays: shedding light on the dark side of multiplexing. Current opinion in chemical biology 18: 29-37 (2014).

King et al., Understanding the FRET signatures of interacting membrane proteins. The Journal of Biological Chemistry 292(13): 5291-5310 (2017).

Krishhan et al., Multiplexed Microbead Immunoassays by Flow Cytometry for Molecular Profiling: Basic Concepts and Proteomics Applications. Crit Rev Biotechnol. 29(1): 29-43 (2009).

Kumar et al., Point-of-care strategies for Detection of Waterborne Pathogens. Sensors 19: 4476 (2019).

Laforte et al., Antibody colocalization microarray for cross-reactivity-free multiplexed protein analysis. Serum/Plasma Proteomics. Human Press 239-261 (2017).

Leone, et al. Molecular beacon probes combined with amplification by NASBA enable homogeneous, real-time detection of RNA. Nucleic Acids Res. May 1, 1998;26(9):2150-5.

Li et al., A new class of homogeneous nucleic acid probes based on specific displacement hybridization. Nucleic Acids Research 30(2): e5 (2002).

Li et al., Novel Antibody Microarray Technologies for Multiplex Protein Analysis in Complex Samples. Doctor of Philosophy Department of Biomedical Engineering. McGill University, Montreal, Quebec, Canada 180 pages (2011).

Mackay, et al. Real-time PCR in virology. Nucleic Acids Res. Mar. 15, 2002;30(6):1292-305.

PCT/CA2019/050405 International Preliminary Report on Patentability dated Oct. 6, 2020.

PCT/CA2019/050405 International Search Report and Written Opinion dated Jun. 17, 2019.

PCT/IB2020/000813 International Preliminary Report on Patentability dated Apr. 5, 2022.

PCT/IB2020/000813 International Search Report and Written Opinion dated Jan. 15, 2021.

PCT/IB2021/000140 International Search Report and Written Opinion dated Jun. 17, 2021.

PCT/IB2021/000140 International Preliminary Report on Patentability dated Sep. 22, 2022.

Stuchly et al., An automated analysis of highly complex flow cytometry-based proteomic data. Cytometry Part A 81A(2): 120-129 (2012).

Tighe, et al. ELISA in the multiplex era: Potentials and pitfalls. Proteomics—Clinical Applications. 9 (2015): 406-422.

Tighe et al., Utility, Reliability and Reproducibility of Immunoassay Multiplex Kits. Methods 61(1):23-29 (2013).

U.S. Appl. No. 16/153,071 Restriction Requirement dated Mar. 4, 2022.

U.S. Appl. No. 16/153,071 Office Action dated Jan. 25, 2023.

U.S. Appl. No. 16/898,338 Final Office Action dated Apr. 13, 2021.

U.S. Appl. No. 16/898,338 First Action Interview dated Dec. 8, 2020.

U.S. Appl. No. 16/898,338 First Action Interview dated Sep. 4, 2020.

U.S. Appl. No. 17/200,680 Final Office Action dated Apr. 17, 2023.

U.S. Appl. No. 17/200,680 Final Office Action dated Nov. 30, 2021.

U.S. Appl. No. 17/200,680 Non-Final Office Action dated May 20, 2021.

U.S. Appl. No. 17/200,680 Non-Final Office Action dated Sep. 29, 2022.

Wagh et al., Polymeric nanoparticles with sequential and multiple FRET cascade mechanism for multicolor and multiplexed imaging. Small 9(12): 2129-2139 (2013).

Wang et al., Multicolor FRET silica nanoparticles by single wavelength excitation. Nano Letters 6(1): 84-88 (2006).

Wolber et al., An analytic solution to the Forster energy transfer problem in two dimensions. Biophysical Journal 28(2): 197-210 (1979).

Zhang et al., Control of DNA strand displacement kinetics using toehold exchange. J Am Chem Soc 131(47):17303-17314 (2009).

Zimmerman et al., "Technical aspects of quantitative competitive PCR," Biotechniques, 21(2):268-279, 1996.

Bioconjugation and Crosslinking Technical Handbook: Reagents for Bioconjugation, Crosslinking, Biotinylation, and Modification of Proteins and Peptides. Thermo Fisher Scientific (2022).

Hein, Christopher D. et al. Click Chemistry, a Powerful Tool for Pharmaceutical Sciences. Pharmaceutical Research 25(10):2216-2230 (2008).

Kolb, Hartmuth C. et al. Click Chemistry: Diverse Chemical Function from a Few Good Reactions. Angewandte Chemie 40(11):2004-2021 (2001).

Lahann, Joerg. Click Chemistry for Biotechnology and Materials Science. John Wiley and Sons (2009).

Li, Jingjing, and Jun-Jie Zhu. Quantum dots for fluorescent biosensing and bio-imaging applications. Analyst 138(9):2506-2515 (2013).

Li, Yougen. et al. Controlled Assembly of Dendrimer-like DNA. Nature Materials 3(1):38-42 (2004).

Li, Yougen. et al. Multiplexed Detection of Pathogen DNA with DNA-based Fluorescence Nanobarcodes. Nature Biotechnology 23(7):885-889 (2005).

Massa, Sam, and Nick Devoogdt. Bioconjugation: Methods and Protocols. Springer Science+Business Media (2019).

Reyes-Garcés, Nathaly et al. Solid Phase Microextraction Devices Prepared on Plastic Support as Potential Single-Use Samplers for Bioanalytical Applications. Analytical Chemistry 87(19):9722-9730 (2015).

Shelbourne, Montserrat et al. Fast Copper-free Click DNA Ligation by the Ring-strain Promoted Alkyne-Azide Cycloaddition Reaction. Chemical Communications 47(22):6257-6259 (2011).

Spitale, Robert C. et al. Structural Imprints in Vivo Decode RNA Regulatory Mechanisms. Nature 519(7544):486-490 (2015).

Sun, Wei. et al. Casting Inorganic Structures With DNA Molds. Science 346(6210):1258361, 1-13 (2014).

U.S. Appl. No. 16/153,071 Office Action dated Aug. 7, 2023.

(56)                References Cited

OTHER PUBLICATIONS

U.S. Appl. No. 16/153,071 Office Action dated Jul. 8, 2024.
U.S. Appl. No. 16/153,071 Office Action dated Mar. 26, 2025.
U.S. Appl. No. 17/200,680 Office Action dated Jul. 29, 2024.
Zhang, Shuaihua. et al. Zeolitic imidazole framework templated synthesis of nanoporous carbon as a novel fiber coating for solid-phase microextraction Analyst 141(3):1127-1135 (2016). Published Online Dec. 24, 2015.
CN202080084264.3 Office Action with Search Report dated Jul. 4, 2025, and an English translation.

\* cited by examiner

Singleplex Sandwich Assay

Multiplex Sandwich Assay

Colocalization-by-Linkage Assay a b

FIG. 18

CLAMP ID

| | | | | | |
|---|---|---|---|---|---|
| Activin A | 1 | CXCL6 | 61 | IL-3 | 121 |
| AITRL (GITR Ligand) | | CXCL7 | | IL-31 | |
| alpha-Synuclein | | CXCL9 | | IL-33 | |
| Amphiregulin | | EGF | | IL-35 | |
| APRIL | | EGFR | | IL-4 | |
| BAFF | | EMMPRIN | | IL-5 | |
| BCMA (TNFRSF17) | | FAS-L | | IL-6 | |
| BDNF | | FGF-1 | | IL-6 R alpha | |
| BMP-9 | | FGF-19 | | IL-7 | |
| BMP2 | 10 | FGF-2 | 70 | IL-8 | 130 |
| BMP4 | | FGF-4 | | IL-9 | |
| BMP6 | | FGF-6 | | LIF | |
| BMP7 | | FGF-7 (KGF) | | M-CSF | |
| C5/C5a | | FGF-9 | | M-CSF R (CD115) | |
| CCL1 | | FLRG (FSTL3) | | MIF | |
| CCL11 | | Flt-3 Ligand | | MMP-1 | |
| CCL13 | | G-CSF | | MMP-10 | |
| CCL14 | | GDF-15 (MIC-1) | | MMP-12 | |
| CCL15 | | GDNF | | MMP-2 | |
| CCL16 | 20 | GM-CSF | 80 | MMP-2 | 140 |
| CCL17 | | Granzyme B | | MMP-3 | |
| CCL18 | | Growth Hormone (Somatotropin) | | MMP-7 | |
| CCL19 | | HGF | | MMP-9 | |
| CCL2 | | HVEM | | NGF beta | |
| CCL20 | | ICAM-1 | | NRG1 beta 1 | |
| CCL21 | | ICAM-2 | | PCSK9 | |
| CCL22 | | IFN alpha | | PDGF-BB | |
| CCL23 | | IFN beta | | PLGF | |
| CCL24 | | IFN gamma | | PTX3 (Pentraxin 3) | |
| CCL25 | 30 | IGF-1 | 90 | S100A8 | 150 |
| CCL26 | | IGF-2 | | SCF | |
| CCL27 | | IL-1 alpha | | ST2 (IL-33R) | |
| CCL28 | | IL-1 beta | | TGF-beta 1 (LAP & Latent) | |
| CCL3 | | IL-1 R1 | | TGF-beta 2 | |
| CCL4 | | IL-1 RA/RN | | TGF-beta 3 | |
| CCL5 | | IL-10 | | Tie-2 | |
| CCL7 | | IL-11 | | TIMP1 | |
| CCL8 | | IL-12 p40 | | Tissue Factor (TF) | |
| CD14 | | IL-12 p70 | | TNF alpha | |
| CD163 | 40 | IL-13 | 100 | TNF alpha | 160 |
| CD276 (B7-H3) | | IL-15 | | TNF beta | |
| CD27L | | Il-15/IL-15R alpha complex | | TNF RI | |
| CD30 | | IL-16 | | TNF RII | |
| CD40 (TNFRSF5) | | IL-17A | | TNF RIII (Lymphotoxin Beta R) | |
| CD40L | | IL-17B | | TPO (Thrombopoietin) | |
| CRP | | IL-17C | | TRAIL | |
| CX3CL1 | | IL-17D | | TREM2 | |
| CXCL1 | | IL-17E (IL-25) | | TSLP | |
| CXCL10 | | IL-17F | | TWEAK | |
| CXCL11 | 50 | IL-18 | 110 | uPA | 170 |
| CXCL12 (alpha) | | IL-2 RA | | VCAM-1 | |
| CXCL12 (beta) | | IL-20 | | VEGF Receptor 2 (Flk-1) | |
| CXCL13 | | IL-21 | | VEGF-A (165) | |
| CXCL14 | | IL-22 | | VEGF-C | |
| CXCL16 | | IL-22 BP | | VEGF-D | |
| CXCL17 | | IL-23 | | VEGFR-1 | |
| CXCL2 | | IL-24 | | WISP-1 (CCN4) | |
| CXCL3 | | IL-27 | | XCL1 (Lymphotactin) | 178 |
| CXCL4 | | IL-28A | | | |
| CXCL5 | 60 | IL-29 | 120 | | |

FIG. 27 (cont.)

GM-CSF CLAMP dynamic range extension and modulation

A

B

SEQUENCE LISTING

```
<160> NUMBER OF SEQ ID NOS: 15

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gtccgatcaa cagccccata aactctcaat aaccaat                              37

<210> SEQ ID NO 2
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tttttttttg tggcggcggt gattggttat tgagagttta tg                       42

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tttttttttg tggcggcggt g                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
caccgccgcc acaaaaaaaa a                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
```

-continued

```
caccgccgcc acaaaaaaaa a                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
caccgccgcc acaaaaaaaa a                                              21

<210> SEQ ID NO 7
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7 tttttactt ttcaaccacc actcaaccat attcaactca ttcgccataa actcattcgc     60
cataaactct caataaccaa t                                              81

<210> SEQ ID NO 8
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8 tttttactt ttcaaccacc actcaaccat attcaactca ttcgccataa actcattcgc     60
cataaactct caataaccaa t                                              81

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
attggttatt gagagtttat ggcgaatgag                                     30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
attggttatt gagagtttat ggcgaatgag                                     30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: Synthetic
```

-continued

```
          oligonucleotide

<400> SEQUENCE: 11
gttgagtggt ggttgattgg ttgggattga                                    30

<210> SEQ ID NO 12
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12 ttttttttttg tggcggcggt ggttgagtgg tggttggtgt tgatt               45

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ctcgtcataa tgtaaaccgg gaatcaacac caaccaccac tcaac                45

<210> SEQ ID NO 14
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14 tttttttactt ttcaaccacc actcaaccat attcaactca ttcgccataa actcattcgc      60
cataaactct caataaccaa t                                          81

<210> SEQ ID NO 15
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15 tttttttactt ttcaaccacc actcaaccat attcaactca ttcgccataa actcattcgc      60
cataaactct caataaccaa tcaccgccgc cacaaaaaaa aa                  102
```

COLOCALIZATION-BY-LINKAGE SANDWICH ASSAYS FOR MULTIPLEXING

CROSS REFERENCE

This application is a continuation of International Patent Application No. PCT/IB2020/000813, filed on Oct. 2, 2020, which claims the benefit of U.S. Provisional Application No. 62/909,701, filed on Oct. 2, 2019, which application is incorporated herein by reference.

SEQUENCE LISTING

The instant application contains a Sequence Listing which has been submitted electronically in ASCII format and is hereby incorporated by reference in its entirety. Said ASCII copy, created on Nov. 8, 2022, is named 57392_701_301_SL.txt and is 4,220 bytes in size.

BACKGROUND

Rapid and specific detection of biological cells and biomolecules, such as red blood cells, white blood cells, platelets, proteins, DNA, and RNA, has become increasingly important in diverse fields such as genomics, proteomics, diagnoses, therapeutics, and pathological studies. For example, the rapid and accurate detection of specific antigens and viruses is critical for combating pandemic diseases such as AIDS, flu, and other infectious diseases. The maturation of genomic technologies and advances in personalized medicine will require faster and more sensitive assays for detecting and quantifying large numbers of cells and biomolecules. Advances in medical research will increasingly rely on the accurate, timely, and cost-effective assessment of multiple proteins through proteomics. However, current automated, highly-sensitive and low-cost assays cannot be multiplexed efficiently.

The sandwich assay is one of the most popular formats for biological assays. In this format, a capture probe molecule is immobilized on a surface. A biological sample containing a target cell or biomolecule of interest is then applied to the surface. The target binds in a concentration dependent manner to the capture probe molecule immobilized on the surface. In a subsequent step, a detection probe molecule is applied to the surface. The detection probe molecule binds to the target biomolecule which is thus "sandwiched" between the capture probe and the detection probe molecules. In some assays, a secondary probe which can bind the detection probe molecule is also applied to the surface. The secondary probe can be conjugated to a label such as a fluorophore, in which case the binding can be detected using a fluorescence scanner or a fluorescence microscope. In some cases, the secondary probe is conjugated to a radioactive element, in which case the radioactivity is detected to read out the assay result. In some cases, the secondary probe is conjugated to an enzyme, in which case a solution containing a substrate is added to the surface and the conversion of the substrate by the enzyme is detected. In all cases the intensity of the signal detected is proportional to the concentration of the target in the biological sample. The requirement of dual recognition in a sandwich assay provides a highly-fidelity signal with low background noise and, as a result, high sensitivity detection.

The enzyme-linked immunosorbent assay (ELISA) is a well-known example of a sandwich assay. The ELISA typically uses antibodies and a color change reaction to identify a biomolecule in a biological sample. For example, an ELISA can use a solid-phase enzyme immunoassay (EIA) to detect the presence of a biomolecule, such as an antigen, in a liquid or wet biological sample applied to the solid-phase. ELISAs are often performed in 96-well or 384-well polystyrene plates, which passively bind antibodies and proteins. It is this binding and immobilization of reagents on a solid surface that makes ELISAs so easy to design and perform. Immobilizing the reagents on the microplate surface makes it easy to separate the bound target biomolecules from unbound materials during the assay and to wash away non-specifically bound materials. In addition, the requirement for dual recognition by both capture and detection probe molecules provides high specificity. The ELISA is thus a powerful tool for measuring specific target biomolecules within a crude preparation.

Sandwich assays can be designed and fabricated to measure or detect multiple analytes in parallel (also called multiplexing). Multiplexed sandwich assays (MSAs) can be carried out using microarrays, such as DNA microarrays, protein microarrays or antibody microarrays. A microarray is a collection of microscopic spots containing biomolecules attached to a substrate surface, such as a glass, plastic or silicon, which thereby form a "microscopic" array. Such microarrays can be used for example to measure the expression levels of large numbers of genes or proteins simultaneously. The biomolecules, such as DNAs, proteins or antibodies, on a microarray chip are typically detected through optical readout of fluorescent labels attached to a target molecule that is specifically attached or hybridized to a probe molecule. The labels used may consist for example of an enzyme, radioisotopes, or a fluorophore.

MSAs can also be conducted on particles. In this case, particles suspended in solution are attached to biomolecules necessary to capture the targets of interest, such as proteins or specific DNA molecules. To conduct assays in multiplex, the particles must be encoded to allow the different assays in solution to be distinguished. A popular format is spectrally-encoded microparticles, which are encoded using fluorescent or luminescent dyes. Particles can also be encoded graphically—hence they are often referred to as "barcoded particles". Particle sizes may range in size from nanometer (nanoparticles) to micrometer (microparticles). Of these, fluorescently-encoded microparticles can be read-out rapidly and with high-throughput on cytometers.

However, current sandwich assays have poor performance when used to measure multiple biomolecules in a sample at the same time (multiplexing). Multiplexed ELISAs are limited by cross-reactivity between reagents such as antibodies, proteins, etc., and are prone to nonspecific signaling as a result. In conventional multiplexed sandwich assays in both array and bead formats, detection antibodies are typically applied as a mixture, but this method gives rise to interactions among reagents that constitute a liability for cross-reactivity. The application of detection antibody mixtures hence leads to spurious binding and generates false-positive signals from non-specific binding events, for example, between a capture and a non-targeted analyte (illustrated in FIG. 1 herein) that can be difficult to distinguish from the real target protein-binding signal. Such reagent-driven cross-reactivity is an inherent problem in MSAs and scales quadratically with the number of targets, severely limiting the scale of multiplexing. Due to problems with cross-reactivity, current MSAs are generally limited to 30-40 targets. Even then, lengthy and costly optimization protocols are needed to uncover and remove cross-reactive reagents (e.g., antibodies), which severely limits the applicability of these assays and increases their cost.

Cross-reactivity also hinders other types of multiplexed assays. For example, accurate protein phosphorylation analysis can be used to reveal cellular signaling events not evident from protein expression levels. Current methods and workflows for quantifying the fraction of post-translational modification (PTM) of a specific protein are severely limited in multiplexing because PTM-specific antibodies often possess inadequate specificity for the protein itself (that is, a phosphor-specific antibody is highly susceptible to the problem of reagent-driven cross-reactivity). As a result, conventional PTM panels are not multiplexed.

Conventional sandwich immunoassays are also not suitable for analyzing protein-protein interactions. Protein-protein interactions are a key part of cellular processes and understanding modulators of these interactions is extremely important to address correlating diseases. However, the use of detection antibody mixtures allows unwanted interactions and leads to spurious binding that can obfuscate the interaction signals. Current multiplexed sandwich assays are also costly because expensive reagents such as antibodies are used inefficiently during manufacturing and performance of the assays. For example, the addition of antibody mixtures in solution necessitates high concentrations (nanomolar), whereas the amount needed to bind to proteins to quantitate for microarrays or microbeads is 3 orders of magnitude less, which corresponds to a 99.9% loss of antibodies. Further, the sensitivity of a given sandwich immunoassay is highly affected by background signal which is often due to non-specific binding and/or incomplete washing of labeled detection antibodies. Methods to reduce incomplete washing by increasing washing cycles and including additive reagents have been used, however these methods result in increased assay times and assay complexity.

U.S. Pat. No. 9,481,945 describes antibody colocalization microarrays (ACM) which depends on the addressing of each capture antibody spot on a microarray by a single detection antibody, thus avoiding interaction between antibody reagents and reproducing assay conditions that are found in single-plex ELISA assays. Execution of this method requires first spotting the capture antibody, removing the slide from the spotter, incubating it with sample, washing and rinsing it as needed, and placing it back for the spotting of the detection antibody followed by binding and incubation. This method thus depends on the transfer of n different reagents to n spots each with a different reagent as well, representing an n-to-n transfer. The need to perform spotting as part of the assay is cumbersome and slow and throughput is limited.

U.S. Pat. No. 7,306,904 describes assays for detection and/or quantification of one or several analyte(s) is solution using so called proximity probes. The proximity probes comprise a binding moiety and a nucleic acid. The nucleic acid from one proximity probe is only capable of interaction with the nucleic acid from the other proximity probe when these are in close proximity, i.e. have bound to the analytes for which they are specific. However, in general multiplexed proximity-based assays require detection or read-out in single-plex format and hence necessitate complex microfluidics to fractionate the sample into n fractions for n-plex assays.

U.S. Patent Application Publication No. US 2016/0153973 describes a method and system which uses cleavable linkers to detect an analyte in an immunoassay. However, the method and system is not suitable for multiplexing or simultaneous detection of multiple analytes in an immunoassay with high sensitivity, due to high background signal and cross-reactivity between reagents.

SUMMARY

There are provided methods and systems for detection and/or quantification of biomolecules using biochemical assays. It is an object of the invention to ameliorate at least some of the deficiencies present in the prior art. Embodiments of the present technology have been developed based on the inventors' appreciation that there is a need for scalable, cost-efficient, sensitive, rapid and/or simple multiplexing sandwich assays, for example to replace the ELISA for routine use. In some aspects therefore, there are provided herein multiplexed sandwich assays, including multiplexed sandwich immunoassays with minimal cross-reactivity between reagents that are rapid, sensitive, cost-effective and/or scalable, allowing simultaneous detection and/or quantification of multiple analytes in a sample.

Methods and systems provided herein are based, at least in part, on the design and construction of linkages between reagents and supports, wherein the linkages enable addressable and programmable topology and function. Without wishing to be limited by theory, it is believed the systems and methods provided herein can reduce or eliminate one or more sources of background noise and/or false-positives in multiplexed sandwich assays. In some embodiments, cross-reactivity between reagents in multiplexed assays is minimized or eliminated by minimizing or eliminating interactions between non-cognate affinity binders. In some embodiments, methods and systems provided herein can reduce or eliminate background noise caused by incomplete washing and/or non-specific binding of detection reagents. In some embodiments, methods and systems provided herein can allow multiplexed detection of post-translational modifications and/or identification of protein-protein interactions through assembly of combinatorial reagent pairs on distinct assay supports. In some embodiments, surface architecture, linker lengths, and/or surface spacing of reagents can be controlled to modulate stringency of binding and signal generation. In some embodiments, additional steps allow stabilizing an assay signal by transducing it from a reversible reaction into stable oligo hybrids to minimize unbinding and hence minimize signal loss after assay completion and thereby increase sensitivity.

In a first aspect, there is provided a biomolecule complex for the detection and/or quantitation of an analyte in a sample, comprising:

an anchor strand attached to a support;

a capture reagent attached to the support; and a detection reagent releasably attached to the anchor strand, the detection reagent or the anchor strand being optionally attached to a first label, the first label being inactive or undetectable;

wherein: the capture reagent and the detection reagent can simultaneously bind to the analyte, if present in the sample, forming a tertiary complex; release of the detection reagent from the anchor strand can release the detection reagent from the support in the absence of the analyte; and the first label can be activated or detected when the detection reagent is released from the anchor strand. The presence of the analyte in the sample is thus determined through detection of the first label on the support after the detection reagent has been released from the anchor strand, since the detection reagent will only remain attached to the support if bound to the analyte in a tertiary complex with the capture reagent. In some embodiments, therefore, the first label is only detected on the support when the analyte is present.

In some embodiments, the amount of the first label on the support, or detected on the support, when the detection reagent is released from the anchor strand is proportional to the quantity and/or concentration of the analyte in the sample.

In some embodiments, the detection reagent or the anchor strand is optionally attached to the first label. In some embodiments, the detection reagent is optionally attached to the first label. In some embodiments, the anchor strand is optionally attached to the first label.

In some embodiments, the detection reagent is releasably attached to the anchor strand directly via a covalent bond, a biotin-streptavidin bond, hydrogen bonding, a hydrophobic interaction, affinity binding, or a non-covalent interaction.

In other embodiments, the detection reagent is attached to the anchor strand indirectly via a hook strand, the detection reagent being linked to the hook strand and the hook strand being releasably attached to the anchor strand, wherein release of the hook strand from the anchor strand can release the detection reagent from the support in the absence of the analyte, and the first label can be activated or detected when the hook strand is released from the anchor strand. In some such embodiments, the amount of the first label on the support when the hook strand is released from the anchor strand is proportional to the quantity and/or concentration of the analyte in the sample.

In some embodiments, at least one of the detection reagent and the hook strand is optionally attached to the first label. For example, the first label may be attached to the hook strand; the first label may be attached to the detection reagent; or the first label may be attached to both the hook strand and the detection reagent. In some embodiments, the first label is absent, i.e., not attached to either the first strand or the detection reagent, e.g., where a second label is attached to a different component in the biomolecule complex.

In some embodiments, the capture reagent is attached to the support directly, e.g., via a covalent bond, a biotin-streptavidin bond, an oligonucleotide linker (such as a DNA oligonucleotide linker), or a polymer linker (such as a polyethylene glycol (PEG) linker). In other embodiments, the capture reagent is attached to the support indirectly, e.g., via linkage to the anchor strand attached to the support, e.g., via an oligonucleotide linker, a polymer linker, or a covalent bond. It should be understood that the capture reagent may be attached to the support using any suitable means, including chemical interaction, affinity binding, etc.

In some embodiments, the anchor strand is a polymer such as PEG or an oligonucleotide such as a single-stranded DNA oligonucleotide, a single-stranded RNA oligonucleotide, or a double-stranded DNA or RNA oligonucleotide. It should be understood that the anchor strand may be attached to the support using any suitable means, such as covalent bond, chemical interaction, affinity binding, a covalent bond, a biotin-streptavidin bond, a DNA oligonucleotide linker, a polymer linker, and the like.

The support is not particularly limited, and any suitable support may be used. Non-limiting examples of supports include microparticles (such as beads), the surface of a multi-well plate, the surface of a glass slide, or a hydrogel matrix. In some embodiments, the support is a bead or microparticle, typically micron-sized, such as without limitation a polystyrene bead, a magnetic bead, a paramagnetic bead, a plastic bead, and the like. In another embodiment, the support is a planar microarray. In some embodiments, the support is a barcoded bead, e.g., a bead attached to a fluorescent or luminescent dye or mixtures thereof.

The hook strand attached to the detection reagent is generally a linker of sufficient length and flexibility to allow the detection reagent and the capture reagent to bind simultaneously to the analyte to form a tertiary complex. Non-limiting examples of hook strands include polymers such as PEG and oligonucleotides such as a single-stranded DNA oligonucleotide, a single-stranded RNA oligonucleotide, or a double-stranded DNA or RNA oligonucleotide.

In certain embodiments of the biomolecule complex provided herein, the hook strand is absent, and the detection reagent is releasably attached to the anchor strand directly, e.g., via a covalent bond, a biotin-streptavidin bond, affinity binding, or the like.

The capture reagent can be any molecule capable of specifically recognizing and binding to a target analyte. Non-limiting examples of capture reagents include antibodies, antigens, proteins, polypeptides, multi-protein complexes, exosomes, oligonucleotides, aptamers, modified aptamers (such as slow off-rate modified aptamers or somamers), and low molecular weight compounds. In certain embodiments, the capture reagent is an antibody and the analyte is an antigen, a protein, a polypeptide, a multi-protein complex, a hormone, or an exosome. In other embodiments, the capture reagent is an antigen, a protein, a polypeptide, a multi-protein complex, or an exosome, and the analyte is an antibody.

Similarly, the detection reagent can be any molecule capable of specifically recognizing and binding to a target analyte. Non-limiting examples of detection reagents include antibodies, antigens, proteins, polypeptides, multi-protein complexes, exosomes, oligonucleotides, and low molecular weight compounds. In certain embodiments, the detection reagent is an antibody and the analyte is an antigen, a protein, a polypeptide, a multi-protein complex, or an exosome. In other embodiments, the detection reagent is an antigen, a protein, a polypeptide, a multi-protein complex, or an exosome, and the analyte is an antibody.

It should be understood that if the capture reagent is an antibody and the analyte is an antigen, a protein, a polypeptide, a multi-protein complex, or an exosome, then the detection reagent is also an antibody capable of binding the analyte at the same time as the capture reagent. Similarly, if the capture reagent is an antigen, a protein, a polypeptide, a multi-protein complex, or an exosome and the analyte is an antibody, then the detection reagent will also be an antigen, a protein, a polypeptide, a multi-protein complex, or an exosome capable of binding the analyte at the same time as the capture reagent.

The capture reagent and the detection reagent may be the same or different, as long as they can both bind the target analyte at the same time, forming a tertiary complex. In some embodiments, the capture reagent and the detection reagent are both antibodies. They may be the same antibodies or different antibodies. They may be different antibodies that bind to the same epitope on the analyte, or they may be different antibodies that bind to different epitopes on the analyte. In the case where the capture reagent and the detection reagent bind the same epitope, they generally bind to different repeats of the epitope on the analyte, the analyte having two or more repeats of the epitope.

The analyte is not meant to be particularly limited and may be any biomolecule or biological cell for which detection and/or quantitation in a sample is desired. Non-limiting examples of analytes include an antigen, an antibody, a protein, a polypeptide, a multi-protein complex, a hormone, an exosome, an oligonucleotide, or a low molecular weight compound. Analytes may be detected in any sample of interest, particularly but not limited to biological samples, such as without limitation bodily fluids (e.g., urine, saliva, blood, serum, plasma, sweat), extracts (e.g., cellular extracts), and solutions containing proteins and/or DNA (e.g., reaction mixtures).

In some embodiments, the detection reagent is attached to the first label. In some embodiments, the hook strand is attached to the first label. In some embodiments, both the detection reagent and the hook strand are attached to the first label. In some embodiments where the first label is absent, neither the detection reagent nor the hook strand are attached to the first label.

In some embodiments, the releasable link between the hook strand and the anchor strand comprises a double-stranded DNA hybrid, the hook strand and the anchor strand comprising complementary single-stranded DNA oligo-nucleotides that hybridize together to form the double-stranded DNA hybrid. In some such embodiments, release of the hook strand from the anchor strand can be performed by raising the temperature so that the DNA hybrid "melts" or is unbound. For example, in embodiments where the melting temperature (Tm) of the double-stranded DNA hybrid is from about 50 to about 80 degrees Celsius, the temperature may be raised above the Tm such that the double-stranded DNA hybrid dissociates, thereby releasing the hook strand from the anchor strand.

In some embodiments, the biomolecule complex provided herein further comprises a displacer agent capable of releas-ing the hook strand from the anchor strand, thereby releasing the detection agent from the support in the absence of the analyte. The displacer agent may be any agent capable of specifically breaking or releasing the link between the hook strand and the anchor strand. For example, the displacer agent may be an enzyme or other agent that cleaves (or otherwise breaks) the releasable link between the hook strand and the anchor strand. Non-limiting examples of displacer agents include enzymes, light, and reducing agents such as DTT. The displacer agent may be capable, for example, of breaking the link between the hook strand and the anchor strand via an enzymatic reaction or by photo-cleavage.

In some embodiments, the displacer agent is an oligo-nucleotide. For example, when the releasable link between the hook strand and the anchor strand comprises a double-stranded DNA hybrid, the displacer agent can be a single-stranded DNA or RNA oligonucleotide that hybridizes to the hook strand or the anchor strand, thereby releasing the hook strand from the anchor strand via an oligonucleotide or DNA displacement reaction. In embodiments where the displacer agent hybridizes to the hook strand, the displacer agent forms a double-stranded DNA or RNA hybrid with the hook strand. In some such embodiments, the displacer agent can be detectably labeled, such that the displacer agent will only be retained on the support after washing if the detection reagent to which the hook strand is attached is bound to the analyte, detection of the label on the displacer agent thereby indicating presence of the analyte in the sample. In some such embodiments, the first label is absent, and detection of the label on the displacer agent is used to detect and/or quantitate the analyte. In some such embodiments, the amount of the label on the displacer agent detected on the support is proportional to the quantity and/or concentration of the analyte in the sample. In embodiments where the displacer agent hybridizes to the anchor strand, the displacer agent forms a double-stranded DNA or RNA hybrid with the anchor strand. It will be understood that in such embodi-ments, the displacer agent is not labeled, the label being attached instead to the detection reagent and/or the hook strand, such that label will only be detected on the support in the presence of the analyte.

In some embodiments, where the first label is absent, and detection of the label on the displacer agent is used to detect and/or quantitate the analyte, and the displacer agent acts via a DNA displacement reaction, the displacer agent binds (e.g., hybridizes) to the hook strand. In other embodiments, where the first label is present on the detection reagent or the hook strand and the displacer agent is not labeled, and the displacer agent acts via a DNA displacement reaction, the displacer agent may bind to either the hook strand or the anchor strand.

In some embodiments, the biomolecule complex further comprises a stem strand complementary to the surface-proximate sequence of the anchor strand, where the stem strand and the anchor strand are both single-stranded oligo-nucleotides, and the stem strand is capable of binding to the anchor strand to form a double-stranded oligonucleotide. In some embodiments, by forming a double-stranded oligo-nucleotide with the anchor strand, the stem strand can provide structural support to the anchor strand, e.g., to prevent the complex from collapsing onto the surface of the support, to provide rigidity, to create a spacer between the surface of the support and the complex, or to provide structural stability. In some embodiments, the stem strand can also be attached to a barcode, e.g., a fluorescent or luminescent dye, and used to attach a barcode label to the support. In general, the stem strand is attached to the anchor strand, e.g., by hybridization, and not covalently bound directly to the support.

In some embodiments where the biomolecule complex comprises a stem strand bound to the anchor to form a DNA hybrid proximate to the surface of the support, the anchor strand is attached to a label (instead of the detection reagent, the hook strand, or the displacer agent, which are all unlabeled). In these embodiments, the anchor strand is attached to a label that is inactive or undetectable when the anchor strand is hybridized to the stem strand; the anchor strand is also linked directly to the detection reagent. Upon cleavage of the DNA hybrid at a site between the label and the support, the label is activated or becomes detectable. The detection reagent will be released from the support in the absence of the analyte, so that signal is only detected in the presence of analyte and after cleavage (i.e., after release of the detection reagent).

In some embodiments, the relative density of the anchor strand and the capture reagent on the support can be adjusted to control the effective affinity of the assay. In some embodi-ments, the length of the hook strand can be adjusted to control the effective affinity of the assay.

In some embodiments, the valency of the conjugation between the detection reagent and the hook strand is selected to minimize cross-reactivity, to optimize performance in a multiplexed assay. In one embodiment, the conjugation between the detection reagent and the hook strand is mon-ovalent. In other embodiments, the conjugation between the detection reagent and the hook strand is 1:2, 1:3, 1:4, 1:5, 1:6, 1:7 or 1:8, or less than 1:6, less than 1:8, or less than 1:10. In other embodiments, at least 90% of the detection reagent is linked to the support via only one hook strand.

In some embodiments where the capture reagent is linked to the anchor strand, the conjugation between the capture reagent and the linker to the anchor strand is monovalent. In some embodiments where the capture reagent is linked to the anchor strand, the conjugation between the capture reagent and the linker to the anchor strand is 1:2, 1:3, 1:4, 1:5, 1:6, 1:7 or 1:8, or less than 1:6, less than 1:8, or less than 1:10. In some embodiments, at least 90% of the capture reagent is linked to the anchor strand via only one capture strand.

In some embodiments, the anchor strand and/or the capture reagent are stochastically distributed on the support.

In some embodiments, the length and/or the flexibility of the hook strand can be selected so as to allow or optimize binding of the detection reagent to the analyte in the presence of the capture reagent.

In some embodiments where the link between the hook strand and the anchor strand is a double-stranded DNA hybrid, the melting temperature (Tm) of the double-stranded DNA hybrid is from about 50 to about 80 degrees Celsius.

In some embodiments, the concentration of the detection reagent after displacement is less than about 10 picomolar, to avoid re-binding of detection reagents to off-target reagents or analytes after the displacement or release has occurred.

In further embodiments, the biomolecule complex comprises two detection reagents, allowing a stronger signal to be generated since two copies of the label are present when the analyte is bound. In these embodiments, the biomolecule complex further comprises a second anchor strand linked to the support; a second detection reagent linked to a second hook strand, wherein the second hook strand is linked to the second anchor strand, and wherein at least one of the second detection reagent and the second hook strand is optionally attached to a third label; wherein the capture reagent, the detection reagent and the second detection reagent can simultaneously bind to the analyte, if present in the sample, forming a quaternary complex. Release of the second hook strand from the second anchor strand can release the second detection reagent from the support in the absence of the analyte and can activate the third label.

In some embodiments, the second detection reagent is attached to the third label. In some embodiments, the second hook strand is attached to the third label. The third label may be any suitable label, such as without limitation a fluorophore, a specific DNA sequence, or a biotin moiety.

In some embodiments where the third label is attached to the second detection reagent and/or the second hook strand and is inactive or undetectable, the third label can be activated or detected only when the second hook strand is released from the second anchor strand and the analyte is present.

In some embodiments, the biomolecule complex further comprises a second displacer agent capable of releasing the second hook strand from the second anchor strand, such that the second detection agent is released from the support in the absence of the analyte. The second displacer agent, like the displacer agent, can release the second hook strand from the second anchor strand by enzymatic reaction, by cleavage, or by oligonucleotide displacement reaction. The second displacer agent can also be detectably labeled, like the displacer agent, in which case the second detection reagent and the second hook strand are generally not labelled (i.e., the third label is absent). The second displacer agent may be the same or different from the displacer agent. In some embodiments, the second displacer agent and the displacer agent are the same, such that one agent can release both the second hook strand and the hook strand from their respective anchor strands.

In one embodiment, there is provided a biomolecule complex for the detection of an analyte in a sample, comprising an anchor strand linked to a support; a capture reagent, wherein the capture reagent is linked to the support; and a detection reagent linked to a hook strand, wherein the hook strand is linked to the anchor strand and wherein the detection reagent is also labeled; wherein the capture reagent and the detection reagent can simultaneously bind to the analyte, if present in the sample, forming a tertiary complex, and the link between the hook strand and the anchor strand can be broken, releasing the detection reagent from the support in the absence of the analyte.

In another embodiment, there is provided a biomolecule complex for the detection of an analyte in a sample, comprising an anchor strand linked to a support, a capture reagent, wherein the capture reagent is linked to a capture strand, wherein the capture strand is linked to the anchor strand; and a detection reagent linked to a hook strand, wherein the hook strand is linked to the anchor strand and wherein the detection reagent is also labeled; wherein the capture reagent and the detection reagent can simultaneously bind to the analyte, if present in the sample, forming a tertiary complex; the link between the hook strand and the anchor strand can be broken, releasing the detection reagent from the support in the absence of the analyte.

In a further embodiment, there is provided a biomolecule complex for the detection of an analyte in a sample, comprising an anchor strand linked to a support, a capture reagent linked to the support; a detection reagent, wherein the detection reagent is linked to a hook strand, wherein the hook strand is linked to the anchor strand; and a displacer agent capable of breaking the link between the anchor strand and the hook strand by binding to the hook strand, leading to the release of the detection reagent and hook strand from the support in the absence of the analyte, the displacer being labeled; wherein the capture reagent and the detection reagent can simultaneously bind to the analyte, if present in the sample, forming a tertiary complex.

In a further embodiment, there is provided a biomolecule complex for the detection of an analyte in a sample, comprising an anchor strand linked to a support, a capture reagent linked to a capture strand, wherein the capture strand is linked to the anchor strand; a detection reagent linked to a hook strand, wherein the hook strand is linked to the anchor strand; and a displacer agent capable of breaking the link between the anchor strand and the hook strand by binding to the hook strand, leading to the release of the detection reagent and the hook strand from the support in the absence of the analyte, the displacer agent being labeled; wherein the capture reagent and the detection reagent can simultaneously bind to the analyte, if present in the sample, forming a tertiary complex.

In another embodiment, there is provided a biomolecule complex for the detection of an analyte in a sample, comprising an anchor strand linked to a support, a capture reagent linked to the support; a detection reagent linked to a hook strand, wherein the hook strand is linked to the anchor strand and comprises an inactivated label; and a displacer agent capable of breaking the link between the anchor strand and the hook strand, leading to the release of the detection reagent and the hook strand from the support in the absence of the analyte; wherein the capture reagent and the detection reagent can simultaneously bind to the analyte, if present in the sample, forming a tertiary complex, and wherein breaking the link between the anchor strand and the hook strand activates the label on the hook strand.

In another embodiment, there is provided a biomolecule complex for the detection of an analyte in a sample, comprising an anchor strand linked to a support, a capture reagent linked to a capture strand, wherein the capture strand is linked to the anchor strand; a detection reagent linked to a hook strand, wherein the hook strand is linked to the anchor strand, the hook strand comprising an inactivated label; and a displacer agent capable of breaking the link between the anchor strand and the hook strand by binding to the anchor strand, leading to the release of the detection reagent and the hook strand from the support in the absence of the analyte; wherein the capture reagent and the detection reagent can simultaneously bind to the analyte, if present in the sample, forming a tertiary complex, and wherein breaking the link between the anchor strand and the hook strand activates the label on the hook strand.

In another embodiment, there is provided a biomolecule complex for the detection of an analyte in a sample, comprising an anchor strand linked to a support, a capture reagent linked to a capture strand, wherein the capture strand is linked to the anchor strand; a detection reagent linked to a hook strand, wherein the hook strand is linked to the anchor strand, the hook strand comprising an inactivated label; and a displacer agent capable of breaking the link between the anchor strand and the hook strand, leading to the release of the detection reagent and the hook strand from the support only in the absence of the analyte; wherein the capture reagent and the detection reagent are the same, and wherein the analyte has repeating epitopes, and the capture reagent and the detection reagent can simultaneously bind to the analyte, if present in the sample, forming a tertiary complex, wherein breaking the link between the anchor strand and the hook strand activates the label on the hook strand.

In a further embodiment, there is provided a biomolecule complex for the detection of an analyte in a sample, comprising an anchor strand linked to a support, a capture reagent linked to a capture strand, wherein the capture strand is linked to the anchor strand; a detection reagent linked to a hook strand, wherein the hook strand is linked to the anchor strand; and a displacer agent capable of breaking the link between the anchor strand and the hook strand by binding to the hook strand, leading to the release of the detection reagent and the hook strand from the support only in the absence of the analyte, wherein the displacer agent is labeled; wherein the capture reagent and the detection reagent are the same, and wherein the analyte has repeating epitopes, and the capture reagent and the detection reagent can simultaneously bind to the analyte, if present in the sample, forming a tertiary complex.

In another embodiment, there is provided a biomolecule complex for the detection of an analyte in a sample, comprising a first anchor strand linked to a support, a second anchor strand linked to the support, and a capture reagent linked to the support; a first detection reagent linked to a first hook strand, wherein the first hook strand is linked to the first anchor strand, the first hook strand comprising an inactivated first label; a second detection reagent linked to a second hook strand, wherein the second hook strand is linked to the second anchor strand, the second hook strand comprising an inactivated second label; a first displacer agent capable of breaking the link between the first anchor strand and the first hook strand, leading to the release of the first detection reagent and the first hook strand from the support in the absence of the analyte; and a second displacer agent capable of breaking the link between the second anchor strand and the second hook strand, leading to the release of the second detection reagent and the second hook strand from the support only in the absence of the analyte, wherein the capture reagent, the first detection reagent, and the second detection reagent can simultaneously bind to the analyte, if present in the sample, forming a quaternary complex, wherein breaking the link between the anchor strand and the first hook strand activates the first label on the first hook strand, wherein breaking the link between the anchor strand and the second hook strand activates the second label on the second hook strand.

In another embodiment, there is provided a biomolecule complex for the detection of an analyte in a sample, comprising a first anchor strand linked to a support, a second anchor strand linked to the support, and a capture reagent linked to the support; a first detection reagent linked to a first hook strand, wherein the first hook strand is linked to the first anchor strand; a second detection reagent linked to a second hook strand, wherein the second hook strand is linked to the second anchor strand; a first displacer agent capable of breaking the link between the first anchor strand and the first hook strand by binding to the first hook strand, leading to the release of the first detection reagent and the first hook strand from the support in the absence of the analyte, wherein the first displacer agent is labeled; and a second displacer agent capable of breaking the link between the second anchor strand and the second hook strand by binding to the second hook strand, leading to the release of the second detection reagent and the second hook strand from the support only in the absence of the analyte, wherein the first displacer agent is labeled; wherein the capture reagent, the first detection reagent, and the second detection reagent can simultaneously bind to the analyte, if present in the sample, forming a quaternary complex.

In some embodiments, the support is a microparticle, the surface of a well plate, the surface of a glass slide, or a hydrogel matrix.

In some embodiments, the capture reagent and the detection reagent are antibodies. In some embodiments, the analyte is an antigen. In some embodiments, the analyte is a multi-protein complex. In some embodiments, the analyte is an exosome.

In other embodiments, the capture reagent and the detection reagent are antigens, and the analyte is an antibody.

In some embodiments, the capture reagent is linked to the support via a covalent bond or via a biotin-streptavidin bond. In some embodiments, the capture reagent is linked to the support via a DNA oligonucleotide linker or via a polymer linker such as a PEG linker. In some embodiments, the detection reagents are linked to the support via a polymer linker such as a PEG linker or via a DNA oligonucleotide linker.

In one embodiment, the hook strand, the anchor strand, and displacer agent are DNA oligonucleotides.

In a further embodiment, the link between the hook strand and the anchor strand is a double-stranded DNA hybrid.

In an embodiment, the link between the anchor strand and the support is a covalent bond or a biotin-streptavidin bond. In another embodiment, the anchor strand is attached to the support via a chemical interaction. It should be understood that the anchor strand may be attached to the support using any suitable means, such as without limitation a covalent bond, a biotin-streptavidin bond, a DNA oligonucleotide linker, a polymer linker, or another chemical interaction such as hydrogen bonding, a hydrophobic interaction, affinity binding, or a non-covalent interaction.

In a further embodiment, the displacer agent breaks the link between the hook strand and the anchor strands via a DNA strand displacement reaction.

In another embodiment, the displacer agent breaks the link between the hook strand and the anchor strands via an enzymatic reaction.

In an embodiment, the label is a fluorophore. In an embodiment, the label is a specific DNA sequence. In an embodiment, the label is a biotin moiety.

In another embodiment, the detection reagent recognizes the same antigen but not the same epitope as the capture reagent.

In another embodiment, the detection reagent recognizes a different epitope bound on the same antigen as bound by the capture reagent.

In another embodiment, the detection reagent recognizes an identical epitope on the same antigen as bound by the capture reagent.

In another embodiment, the biomolecule complex described herein further comprises a stem strand complementary to the surface-proximate sequence of the anchor strand, the stem strand rendering the anchor oligonucleotide double-stranded.

In an embodiment, the relative density of the anchor strand and the capture reagent is adjusted to control the effective affinity of the assay.

In another embodiment, the length of the detection of the analyte (e.g., the length of the hook strand) is adjusted to control the effective affinity of the detection.

In another embodiment, the conjugation between detection reagent and hook strand is monovalent.

In an embodiment, the anchor strand is stochastically distributed. In another embodiment, the capture reagent is stochastically distributed.

There is also provided a method for detecting an analyte from a sample, comprising providing a support, a capture reagent, an anchor strand, a hook strand, and a detection reagent, wherein the capture reagent is linked to the support, the anchor strand is linked the support and to the hook strand, wherein the hook strand is linked to the detection reagent, wherein the detection reagent is labeled; incubating the sample with the support allowing binding of the capture reagent and the detection reagent to different epitopes on the analyte; breaking the bond between the hook strand and the anchor strand, separating the detection reagent and hook strand from the support in the absence of the analyte bound to the capture reagent and the detection reagent; and quantifying an amount of the bound analyte by analyzing the detection reagent label remaining on the support, wherein the detection reagent label concentration remaining on the support is in proportion to the concentration of the analyte bound.

There is further provided a method for detecting an analyte from a sample, comprising providing a support, an anchor strand, a capture strand, a capture reagent, a hook strand, and a detection reagent, wherein the anchor strand is linked to the support, to the capture strand and the hook strand, the capture strand is linked to the capture reagent, and wherein the hook strand is linked to the detection reagent; incubating the sample with the support allowing binding of the capture reagent and the detection reagent to different epitopes on the analyte; breaking the bond between the hook strand and the anchor strand by separating the detection reagent and the hook strand from the support in the absence of the analyte bound to the capture reagent and the detection reagent; and quantifying an amount of the bound analyte by analyzing the detection reagent label remaining on the support, wherein the detection reagent label concentration remaining on the support is in proportion to the concentration of the analyte bound.

There is further provided a method for detecting an analyte from a sample, comprising providing a support, a capture reagent, an anchor strand, a hook strand, and a detection reagent, wherein the capture reagent is linked to the support, wherein the anchor strand is linked the support and to the hook strand, wherein the hook strand is linked to the detection reagent; incubating the sample with the support allowing binding of the capture reagent and detection reagent to different epitopes on the analyte; incubating with a displacer agent to break the bond between the hook strand and the anchor strand by binding to the hook strand, separating the detection reagent and the hook strand from the support in the absence of the analyte bound to both the capture reagent and the detection reagent, wherein the displacer agent is labeled; quantifying an amount of the bound analyte by analyzing the displacer agent label remaining on the support, wherein the displacer agent label concentration remaining on the support is in proportion to the concentration of the analyte bound.

In another embodiment, there is provided a method for detecting an analyte from a sample, comprising providing a support, an anchor strand, a capture strand, a capture reagent, a hook strand, and a detection reagent, wherein the anchor strand is linked to the support and to the capture strand, wherein the capture strand is linked to the capture reagent, the anchor strand is linked to the hook strand, and wherein the hook strand is linked to the detection reagent; incubating the sample with the support allowing binding of the capture reagent and the detection reagent to different epitopes on the analyte; incubating with a displacer agent to break the bond between the hook strand and the anchor strand by binding to the hook strand, separating the detection reagent and the hook strand from the support in the absence of the analyte bound to both the capture reagent and the detection reagent, wherein the displacer agent is labeled; and quantifying an amount of the bound analyte by analyzing the displacer agent label remaining on the support, wherein the displacer agent label concentration remaining on the support is in proportion the concentration of the analyte bound.

There is further provided a method for detecting an analyte from a sample, comprising providing a support, a capture reagent, an anchor strand, a hook strand, and a detection reagent, wherein the capture reagent is linked to the support, wherein the anchor strand is linked the support and to the hook strand, wherein the hook strand is linked to the detection reagent, wherein the hook strand comprises an inactivated label; incubating the sample with the support allowing binding of the capture reagent and the detection reagent to different epitopes on the same analyte; incubating with a displacer agent to break the bond between the hook strand and the anchor strand, separating the detection reagent and hook strand from the support in the absence of the analyte bound to both the capture reagent and the detection reagent, wherein separating the hook strand from the anchor strand activates the label on the hook strand; and quantifying an amount of the bound analyte by analyzing the hook strand label remaining on the support, wherein the hook strand label concentration remaining on the support is in proportion to the concentration of the analyte bound.

There is further provided a method for detecting an analyte from a sample, comprising providing a support, an anchor strand, a capture strand, a capture reagent, a hook strand, and a detection reagent, wherein the anchor strand is linked to the support, the capture strand and the hook strand, wherein the capture strand is linked to the capture reagent, wherein the hook strand is linked to the detection reagent and comprises an inactivated label; incubating the sample with the support allowing binding of the capture reagent and the detection reagent to different epitopes on the analyte; incubating with a displacer agent to break the bond between the hook strand and the anchor strand by binding to the anchor strand, separating the detection reagent and the hook strand from the support only in the absence of the analyte bound to both the capture reagent and the detection reagent, wherein separating the hook strand from the anchor strand activates the label on the hook strand; and quantifying an amount of the bound analyte by analyzing the hook strand label remaining on the support, wherein the hook strand label concentration remaining on the support is in proportion to the concentration of the analyte bound.

There is also provided a method for detecting an analyte from a sample, comprising providing a support, an anchor strand, a capture strand, a hook strand, a capture reagent and a detection reagent, wherein the anchor strand is linked to the support, to the capture strand and to the hook strand, wherein the capture strand is linked to the capture reagent, wherein the hook strand is linked to the detection reagent, wherein the hook strand comprises an inactivated label, and wherein the capture reagent and the detection reagent are structurally similar; incubating the sample with the support allowing binding of the capture reagent and the detection reagent to different epitopes on the analyte, wherein the epitopes are structurally similar; incubating with a displacer agent to break the bond between the hook strand and the anchor strand, separating the detection reagent and the hook strand from the support in the absence of the analyte bound to both the capture reagent and the detection reagent, wherein separating the hook strand from the anchor strand activates a label on the hook strand; and quantifying an amount of the bound analyte by analyzing the hook strand label remaining on the support, wherein the hook strand label concentration remaining on the support is in proportion to the concentration of the analyte bound.

There is further provided a method for detecting an analyte from a sample, comprising providing a support, an anchor strand, a capture strand, a hook strand, a capture reagent and a detection reagent, wherein the anchor strand is linked to the support, to the capture strand and the hook strand, wherein the capture strand is linked to the capture reagent, wherein the hook strand is linked to the detection reagent, and wherein the capture reagent and the detection reagent are structurally similar; incubating the sample with the support allowing binding of the capture reagent and the detection reagent to different epitopes on the analyte, wherein the epitopes are structurally similar; incubating with a displacer agent to break the bond between the hook strand and the anchor strand by binding to the hook strand, separating the detection reagent and the hook strand from the support in the absence of the analyte bound to both the capture reagent and the detection reagent, wherein the displacer agent is labeled; and quantifying an amount of the bound analyte by analyzing the displacer strand label remaining on the support, wherein the displacer strand label concentration remaining on the support is in proportion the concentration of the analyte bound.

In an embodiment, the capture reagent and the detection reagent are peptides. In an embodiment, the capture reagent is linked to the support via a DNA oligonucleotide linker. In another embodiment, the detection reagent is linked to the support via a PEG linker.

In a further embodiment, the hook strand, anchor strand, and displacer agents are DNA oligonucleotides. In an embodiment, the link between hook strand and the anchor strand is a double-stranded DNA hybrid. In a further embodiment, the link between the anchor strand and the support is a covalent bond. In an embodiment, the link between the anchor strand and the support is a biotin-streptavidin bond.

In an embodiment, the displacer agent breaks the link between the hook strand and the anchor strands via a DNA strand displacement reaction. In an embodiment, the displacer agent breaks the link between the hook strand and the anchor strands via a enzymatic reaction.

In another embodiment, the label is a biotin moiety.

In a further embodiment, the anchor strand is linked to the microparticles via a chemical interaction.

In another embodiment, the detection reagent recognizes the same antigen but not the same epitope as the capture reagent. In a further embodiment, the detection reagent recognizes a different antigen bound to the same antigen as bound by the capture reagent. In an embodiment, the detection reagent recognizes an identical epitope on a different location of the same antigen as bound by the capture reagent.

In an embodiment, the biomolecule complex described herein further comprises a stem strand complementary to the surface-proximate sequence of the anchor strand, rendering the anchor oligonucleotide double-stranded.

In an embodiment, the relative density of the anchor strands and the capture reagent are adjusted to control the effective affinity of the assay.

In an embodiment, the length of the detection of the analyte (e.g., the hook strand) is adjusted to control the effective affinity of the detection.

In an embodiment, the conjugation between the detection reagent and the hook strand is monovalent.

In another embodiment, the anchor strand is stochastically distributed.

In a further embodiment, the capture reagent is stochastically distributed.

There is also provided a multitude of complex detection systems for the detection of multiple analytes in a sample, comprising a multitude of supports; a multitude of capture reagents, wherein each capture reagent is bound to its respective support; a multitude of detection reagents, wherein each detection reagent is bound to its respective support via a linker, wherein the detection reagents are labeled; wherein on each support, the capture reagent and detection reagents can simultaneously bind to the support-specific analyte, if present in the sample, forming a tertiary complex; the linker between the detection reagents and their respective supports can be broken, releasing the detection reagent from the support in the absence of the analyte.

There is further provided a multitude of complex detection systems for the detection of multiple analytes in a sample, comprising a multitude of supports; a multitude of capture reagents, wherein each capture reagent is bound to its respective support; a multitude of detection reagents, wherein each detection reagent is bound to its respective support via a support-specific hook strand, wherein each hook strand comprises a support-specific inactivated label; a displacer agent, wherein the displacer agent is capable of breaking the bond between the multitude of hook strands and the multitude of supports, separating the detection reagents from their respective supports; wherein on each support, the capture reagent and detection reagents can simultaneously bind to the support-specific analyte, if present in the sample, forming a tertiary complex; wherein breaking the bond between the support and the hook strands activates the support-specific labels on the hook strands.

There is also provided a multitude of complex detection systems for the detection of multiple analytes in a sample, comprising a multitude of supports; a multitude of capture reagents, wherein each capture reagent is bound to its respective support; a multitude of detection reagents, wherein each detection reagent is bound to its respective support via a support-specific hook strand; a displacer agent, wherein the displacer agent is capable of breaking the bond between the multitude of hook strands and the multitude of supports, wherein upon breaking the bond between the hook strand and the support the displacer agent binds to the hook strand, wherein the displacer agent is labeled; wherein on each support, the capture reagent and detection reagents can simultaneously bind to the support-specific analyte, if present in the sample, forming a tertiary complex.

In an embodiment, there is also provided a multitude of complex detection systems for the detection of multiple analytes in a sample, comprising a multitude of supports; a multitude of capture reagents, wherein each capture reagent is bound to its respective support; a multitude of detection reagents, wherein every detection reagent is linked to its respective support, wherein each detection reagent comprises an inactivated label, wherein the link between the detection reagents and their respective supports can be broken; wherein on each support, the capture reagent and detection reagents can simultaneously bind to the support-specific analyte, if present in the sample, forming a tertiary complex, whereupon breaking the link between the detection reagents and their respective supports, the detection reagent label is activated.

There is additionally provided a method for detecting an analyte from a sample, comprising providing a support, an anchor strand, a capture strand, a hook strand, a capture reagent and a detection reagent, wherein the anchor strand is linked to the support, wherein the anchor strand is also linked to the capture strand, wherein the capture strand is linked to the capture reagent, wherein the anchor strand is also linked to the hook strand, wherein the hook strand is linked to the detection reagent; incubating the sample with the support, under a condition to allow binding of the capture and detection reagents to different epitopes on the same analyte; incubating with a displacer agent to break the bond between the hook and anchor strands by binding to the hook strand, separating the detection reagent and hook strand from the support only in the absence of the analyte bound to both the capture and detection reagents, wherein the displacer agent is labeled; quantifying an amount of the bound analyte by analyzing the displacer strand label remaining on the support, wherein the displacer strand label concentration remaining on the support is in proportion to changes in the concentration of the analyte bound.

There is further provided a method for detecting an analyte from a sample, comprising providing a support, an anchor strand, a capture reagent, a hook strand, and a detection reagent, wherein the anchor strand is linked to the support, wherein the capture reagent is linked to the support, wherein the anchor strand, wherein the hook strand is linked to the support, wherein the hook strand is linked to the detection reagent; incubating the sample with the support, under a condition to allow binding of the capture and detection reagents to different epitopes on the same analyte; breaking the bond between the hook strand and the support, separating the detection reagent and hook strand from the support only in the absence of the analyte bound to both the capture and detection reagents; incubating with a bridge strand, wherein the bridge strand links the anchor strand to hook strand, wherein the bridge strand is labeled quantifying an amount of the bound analyte by analyzing the bridge strand label remaining on the support, wherein the bridge strand label concentration remaining on the support is in proportion to changes in the concentration of the analyte bound.

In some embodiments, the hook strand is labelled via inclusion of a label sequence, i.e., a unique DNA sequence that can be detected. In some such embodiments, the hook strand further comprises a re-bind sequence; after release of the hook strand from the anchor strand using a displacer agent oligonucleotide that binds to the anchor strand, a bridge strand is added, where the bridge strand can bind to both the re-bind sequence on the hook strand and the anchor strand, thereby reconnecting the hook strand indirectly to the anchor strand. In such embodiments, after the label attached to the hook strand is activated or made detectable by release from the anchor strand, the hook strand with the active/detectable label is re-attached to the support.

In one embodiment, there is provided a biomolecule complex for the detection and/or quantitation of an analyte in a sample, comprising: a) an anchor strand attached to a support; b) a capture reagent attached to the support; c) a detection reagent linked to a hook strand, the hook strand being releasably attached to the anchor strand, the hook strand and the anchor strand being linked together by a double-stranded DNA hybrid; and d) a displacer agent comprising a DNA oligonucleotide complementary to at least a portion of the hook strand and capable of hybridizing to the hook strand, thereby releasing the hook strand from the anchor strand via a DNA displacement reaction, the displacer agent being detectably labeled; wherein: the capture reagent and the detection reagent can simultaneously bind to the analyte, if present in the sample, forming a tertiary complex; and release of the hook strand from the anchor strand by the displacer agent can release the detection reagent from the support in the absence of the analyte. In an embodiment, the capture reagent and the detection reagent are antibodies, the analyte is an antigen or a protein, and the support is a barcoded microparticle.

In a second aspect, there is provided a multiplex sandwich assay system for the simultaneous detection and/or quantitation of two or more analytes in a sample, the system comprising two or more biomolecule complexes as described herein, wherein each biomolecule complex is for the detection and/or quantitation of a different analyte in the sample.

In some embodiments, the two or more biomolecule complexes are attached to the same support. For example, the support may be a planar surface, the surface of a multi-well plate, the surface of a glass slide, a hydrogel matrix, a microparticle, etc. In such embodiments, each biomolecule complex is positioned at a separate place on the support, allowing each labeled complex (and hence each analyte) to be identified by its position.

In some embodiments, the two or more biomolecule complexes are attached to different supports, e.g., different barcoded microparticles. For example, a first biomolecule complex may be attached to a first bead which is barcoded, e.g., attached to a first fluorescent or luminescent dye or mixture of dyes, and a second biomolecule complex may be attached to a second bead which is also barcoded, e.g., attached to a second fluorescent or luminescent dye or mixture of dyes. After the first and second complexes have been assembled on their respective beads, they can be mixed and contacted with the sample together, allowing for simultaneous detection of the two different analytes in the sample. The barcoding on the beads allows each labelled complex (and hence each analyte) to be identified.

In some embodiments, one or more of the two or more biomolecule complexes comprises a second anchor strand, a second detection reagent linked to a second hook strand, etc., such that a quaternary complex is formed between the capture reagent, the two detection reagents and the analyte.

In some embodiments, the two or more biomolecule complexes all lack the optional first label on the detection reagent or the hook strand, the label being provided only on the displacer agent. In some embodiments, the same labeled displacer agent is used to release the respective hook strand from the respective anchor strand for each biomolecule complex, each biomolecule complex (and its respective analyte) being identified by its position on the surface or by barcoding of the surface, particularly where the surface is a microparticle. In other embodiments, a different displacer agent with a different label may be used for each biomolecule complex.

In some embodiments, the two or more biomolecule complexes may each detect and/or quantitate the same analyte, wherein each of the biomolecule complexes has a different effective affinity for the analyte. For example, the effective affinity of the biomolecule complex for the analyte can be selected by adjusting the length of the hook strand and/or the anchor strand and/or adjusting the surface densities of the capture reagent and/or the detection reagent. In this way, an analyte may be assayed over a large range of concentrations.

wherein the length of the hook strand and/or the anchor strand can be adjusted to control the effective affinity of the assay; and/or wherein the surface densities of the capture reagent and/or the detection reagent can be adjusted to control the effective affinity of the assay It should be understood that the number of analytes that may be detected and/or quantitated at the same time in a multiplex sandwich assay system is not particularly limited. In some embodiments, a multiplex sandwich assay system may be used for the simultaneous detection and/or quantitation of five or more analytes, ten or more analytes, 15 or more analytes, 20 or more analytes, 30 or more analytes, 40 or more analytes, 50 or more analytes, 75 or more analytes, or 100 or more analytes in a sample, the system comprising a respective biomolecule complex specific for each respective analyte. The multiplex sandwich assay system is thus easily scalable for large-scale multiplexing.

In a third aspect, there is provided a method for detecting and/or quantitating an analyte in a sample, using a biomolecule complex as described herein.

In some embodiments, there are provided methods for simultaneous detection and/or quantitation of two or more analytes in a sample, using two or more biomolecule complexes as described herein, wherein each biomolecule complex is for the detection and/or quantitation of a different analyte in the sample. In some embodiments, there are provided methods for the simultaneous detection and/or quantitation of two or more analytes in a sample using a multiplex sandwich assay system as described herein, the system comprising two or more biomolecule complexes as described herein, wherein each biomolecule complex is for the detection and/or quantitation of a different analyte in the sample. It should be understood that methods provided herein may be used for the simultaneous detection and/or quantitation of a large number of analytes in a sample, the methods being scalable to allow large-scale multiplexing.

In an embodiment, there is provided a method for detecting and/or quantitating an analyte in a sample, the method comprising: a) providing a support, a capture reagent attached to the support, an anchor strand attached to the support, and a detection reagent optionally linked to a hook strand, wherein the detection reagent or the hook strand is releasably linked to the anchor strand, and wherein at least one of the detection reagent and the hook strand is optionally attached to a first label, the first label being inactive or undetectable; b) contacting the support with the sample under conditions that allow simultaneous binding of the capture reagent and the detection reagent to the analyte, to form a tertiary complex; and c) adding a displacer agent optionally attached to a second label, wherein the displacer agent releases the detection reagent or the hook strand from the anchor strand, such that the detection reagent optionally linked to the hook strand is released from the support in the absence of the analyte, and wherein the release of the detection strand or the hook strand from the anchor stand activates the first label or makes the first label detectable.

In some embodiments, the method further comprises the following step: d) determining the presence and/or the amount of the first label and/or the second label on the support, wherein the presence of the first and/or the second label on the support indicates the presence of the analyte in the sample, and the amount of the first and/or the second label is proportional to the quantity and/or concentration of the analyte in the sample.

In some embodiments, the method further comprises a step of washing the support to remove any unbound reagents or materials after step (c).

In some embodiments, the method further comprises a step of storing the support after step (c).

In some embodiments of the methods provided herein, the support further comprises a second anchor strand attached to the support, a second capture reagent attached to the support, and a second detection reagent optionally linked to a second hook strand, wherein the second detection reagent or the second hook strand is linked to the second anchor strand, and wherein at least one of the second detection reagent and the second hood strand is optionally attached to a third label, the third label being inactive or undetectable, wherein the second capture reagent and the second detection reagent can bind simultaneously to a second analyte in the sample, to form a second tertiary complex; wherein the displacer agent also releases the second detection reagent or the second hook strand from the second anchor strand, such that the second detection reagent optionally linked to the second hook strand is released from the support in the absence of the second analyte, and wherein the release of the second detection reagent or the second hook strand from the second anchor stand activates the third label or makes the third label detectable; wherein the presence and/or the amount of the third label on the support indicates the presence of the second analyte in the sample, and the amount of the third label on the support is proportional to the quantity and/or concentration of the second analyte in the sample; such that the first analyte and the second analyte can be simultaneously detected and/or quantitated in the sample.

In some embodiments, the second anchor strand and the second capture reagent are positioned at a first location and a second location respectively on the support. In other embodiments, the second anchor strand and the second capture reagent are attached to a second support. The support and/or the second support may be, for example, a microparticle such as a polystyrene bead. In an embodiment, the first support is a first barcoded bead attached to a first fluorescent or luminescent dye, and the second support is a second barcoded bead attached to a second fluorescent or luminescent dye, allowing identification of the respective beads when the respective fluorescent or luminescent dyes are detected.

In some embodiments, the first support and the second support are mixed together before being contacted with the sample. For example, the first support and the second support may be contacted with the sample simultaneously. The sample may be a biological sample, such as without limitation a bodily fluid, an extract, a solution containing proteins and/or DNA, a cell extract, a cell lysate, or a tissue lysate. Non-limiting examples of bodily fluids include urine, saliva, blood, serum, plasma, cerebrospinal fluid, tears, semen, and sweat.

In some embodiments, the method uses a hook strand that is labelled via inclusion of a label sequence, i.e., a unique DNA sequence that can be detected. In some such embodiments, the hook strand further comprises a re-bind sequence; after release of the hook strand from the anchor strand using a displacer agent oligonucleotide that binds to the anchor strand, and optional washing, a bridge strand is added, wherein the bridge strand binds to both the re-bind sequence on the hook strand and the anchor strand, thereby reconnecting the hook strand indirectly to the anchor strand. In such embodiments, after the label attached to the hook strand is activated or made detectable by release from the anchor strand, the hook strand with the active/detectable label is re-attached to the support.

In one embodiment, there is provided a method for the detection and/or quantitation of an analyte in a sample, the method comprising: a) providing a support, a capture reagent attached to the support, an anchor strand attached to the support, and a detection reagent linked to a hook strand, wherein the hook strand is releasably linked to the anchor strand by a double-stranded DNA hybrid; b) contacting support with the sample under conditions that allow simultaneous binding of the capture reagent and the detection reagent to the analyte, to form a tertiary complex; and c) adding a displacer agent attached to a detectable label, wherein the displacer agent is a DNA oligonucleotide complementary to at least a portion of the hook strand and capable of hybridizing to the hook strand, wherein the displacer agent releases the hook strand from the anchor strand via a DNA displacement reaction, such that the detection reagent is released from the support in the absence of the analyte; and d) optionally determining the presence and/or the amount of the detectable label on the support, wherein the presence of the label on the support indicates the presence of the analyte in the sample, and the amount of the label is proportional to the quantity and/or concentration of the analyte in the sample. In some embodiments, the capture reagent and the detection reagent are antibodies, the analyte is an antigen or protein, and the support is a barcoded microparticle.

In a fourth aspect, there is provided a method for preparing a multiplex sandwich assay system, the method comprising: (a) providing a first container comprising a first microparticle, the first microparticle being barcoded via attachment to a first fluorescent or luminescent dye or mixture of dyes; (b) attaching the first microparticle to a first capture reagent and a first detection reagent; (c) optionally, storing the first microparticle; (d) providing a second container comprising a second microparticle, the second microparticle being barcoded via attachment to a second fluorescent or luminescent dye or mixture of dyes; (e) attaching the second microparticle to a second capture reagent and a second detection reagent; (f) optionally, storing the second microparticle; and (g) mixing the first microparticle and the second microparticle together for use in the multiplex sandwich assay system; wherein the first capture reagent and the first detection reagent are not mixed with the second capture reagent and the second detection reagent prior to attachment to their respective microparticle.

In some embodiments, the respective capture reagent and the respective detection reagent are attached to their respective microparticle at the same time. In other embodiments, the respective capture reagent and the respective detection reagent are attached to their respective microparticle in a two-step reaction, where either the capture reagent or the detection reagent is attached to the microparticle first, followed by subsequent attachment of the other reagent.

In some embodiments, the method further comprises the step of washing the first microparticle and the second microparticle to remove unattached reagents, before mixing them together in step (g). In some embodiments, the method further comprises one or more additional washing step, each step of attaching a capture reagent and/or a detection reagent being followed by a washing step to remove unattached and/or non-specifically attached reagents from the microparticle.

In some embodiments, the microparticle is a bead, e.g., a polystyrene bead. In some embodiments, the microparticle in step (a) is not barcoded, and the method further comprises a step of barcoding the microparticle (e.g., attaching a barcode fluorescent or luminescent dye(s) to the microparticle) before step (g), i.e., before mixing a first microparticle and a second microparticle together.

In some embodiments, the first capture reagent, the first detection reagent, the second capture reagent, and the second detection reagent are antibodies.

In an embodiment, there is provided a method of preparing the multiplex sandwich assay system as described herein, the method comprising: (a) providing a support, the support being a planar surface, the surface of a multi-well plate, the surface of a glass plate, or a hydrogel; (b) attaching a first capture reagent to the support at a first position; (c) washing the support to remove unattached first capture reagent; (d) attaching a second capture reagent to the support at a second position; (e) washing the support to remove unattached second capture reagent; (f) attaching a first detection reagent to the support via a first anchor strand attached to the support at the first position; (g) washing the support to remove unattached first detection reagent; (h) attaching a second detection reagent to the support via a second anchor strand attached to the support at the second position; and (i) washing the support to remove unattached second detection reagent; such that whenever the first capture, second capture, first detection, and/or second detection reagents are mixed together, no more than one reagent at a time is not attached to the support.

In some embodiments, methods of preparation of a multiplex sandwich assay system as described herein are advantageous in minimizing cross-reactivity, since the different reagents (capture reagents, detection reagents) are not mixed together in solution before being attached to the support and/or assembled in a biomolecule complex. In this way, non-specific binding of reagents to each other is avoided or at least reduced, in order to minimize cross-reactivity. Undesired background signal or "noise" may also be avoided or at least reduced. In some embodiments, methods are also scalable, allowing rapid and/or cost-effective preparation of multiplex sandwich assay systems. In some embodiments, much less capture and/or detection reagent is needed than for conventional assay systems, which can lead to substantial cost savings for expensive antibody reagents and the like. In some embodiments, less than a nanoliter of an antibody reagent may be needed to prepare a biomolecule complex, for example.

In an aspect, disclosed is a colocalization-by-linkage (CLA) composition for the detection or quantification of an analyte in a sample, the colocalization-by-linkage composition comprising: (a) CLA structure that comprises: (i) a support; (ii) a capture agent attached to the support; (iii) a detection agent anchor polynucleotide attached to the support, wherein the anchor polynucleotide comprises an anchor sequence; and (iv) a detection agent linked to a hook polynucleotide and an anchor-binding sequence complementary to at least a portion of the anchor sequence, wherein the detection agent is releasably bound to the detection agent anchor polynucleotide; (b) a detectably-labeled displacement agent capable of releasing the detection agent from the detection reagent anchor polynucleotide; wherein the capture agent and the detection agent can simultaneously bind the analyte. In some embodiments, the hook polynucleotide comprises a structural property that can be altered and wherein alteration of the structural property alters the binding of the detection agent to the analyte. In some embodiments, the structural property is flexibility of the hook polynucleotide. In some embodiments, the colocalization-by-linkage composition further comprises a stiffening polynucleotide complementary to at least a portion of the hook polynucleotide and wherein binding of the additional polynucleotide reduces flexibility of the hook polynucleotide. In some embodiments, the hook polynucleotide comprises a stem-loop structure. In some embodiments, the stem-loop structure is reversibly formable. In some embodiments, the stem-loop structure is transiently formable. The hook polynucleotide further comprises a polynucleotide sequence that results in a desired propensity to form a stem-loop structure.

In some embodiments, the colocalization-by-linkage composition comprises an additional looping polynucleotide comprising a sequence complementary to a first and a second segment of the hook polynucleotide, wherein a third segment of the hook polynucleotide is located in between the first and the second segment. In some embodiments, binding of the looping polynucleotide to the hook polynucleotide forms cause the hook polynucleotide to form a loop structure. In some embodiments, formation of the loop structure reduces the binding of the detection agent to the analyte. In some embodiments, the colocalization-by-linkage composition, further comprising a hindering polynucleotide that is complementary to at least a portion of the hook strand and wherein binding of the additional polynucleotide sterically hinders the ability of the detection agent to bind the analyte.

In some embodiments, the displacement agent is a detectably-labeled polynucleotide molecule comprising a polynucleotide sequence complementary to at least a portion of the hook polynucleotide. In some embodiments, the detectably-labeled polynucleotide molecule comprises a dye conjugated to a polynucleotide. In some embodiments, the polymer dye is Brilliant Violet 421. In some embodiments, the polymer dye is Super Bright 436.

In some embodiments, the capture agent is attached to the support by a polynucleic acid molecule. In some embodiments, the support is a bead. In some embodiments, the capture agent and/or the detection agent comprise an antibody molecule.

In an aspect, further disclosed is a method for detecting or quantifying an analyte in a sample; the method comprising:

a. contacting the sample with the structure;
b. adding the detectably-labeled displacement agent and releasing the detection agent from the detection agent anchor polynucleotide; and
c. detecting the presence or absence of the detectably-labeled displacement agent.

In some embodiments, the method comprises one or more wash steps prior to (b). In some embodiments, the method further comprises one or more wash steps prior to (c). In some embodiments, the method further comprises one or more wash steps prior to (b) and (c). In some embodiments, the capture agent comprises a first antibody and the detection agent comprises a second antibody.

In an aspect, disclosed is a method for detecting and quantifying an analyte within a sample, the method comprising:

a) contacting the sample with CLA structure that comprises:
   i. a support,
   ii. a capture agent attached to the support;
   iii. a detection agent anchor polynucleotide attached to the support, wherein the anchor polynucleotide comprises an anchor sequence; and
   iv. a detection agent linked to a hook polynucleotide and an anchor-binding sequence complementary to at least a portion of the anchor sequence, wherein the detection agent is releasably bound to the detection agent anchor polynucleotide;
b) adding a detectably-labeled displacement agent that binds the hook polynucleotide and releases the detection agent and the hook polynucleotide from the detection agent anchor polynucleotide; and
c) detecting the presence or absence of the detectably-labeled displacement agent indicating the presence or absence of the detection agent bound to the analyte.

In some embodiments, the method does not comprise a wash step. In some embodiments, the method comprises a wash step prior to (b) or (c). In some embodiments, the method comprises a wash step prior to (b) and (c).

In an aspect, disclosed is a colocalization-by-linkage composition for the detection or quantification of cross reactivity of antibody pairings in a sample, the colocalization-by-linkage composition comprising:

a) A CLA structure that comprises:
   i. a support;
   ii. a capture antibody attached to the support;
   iii. a detection agent anchor polynucleotide attached to the support, wherein the anchor polynucleotide comprises an anchor sequence; and
   iv. a detection antibody linked to a hook polynucleotide and an anchor-binding sequence complementary to at least a portion of the anchor sequence, wherein the detection agent is releasably bound to the detection agent anchor polynucleotide;
b) a detectably-labeled displacement agent capable of releasing the detection agent from the detection reagent anchor polynucleotide;

wherein the capture agent and the detection agent can simultaneously bind the analyte.

In some embodiments, the capture and the detection antibody are not identical. In some embodiments, the capture and the detection antibody bind different epitopes on an analyte. In some embodiments, a sample comprises a single antigen. In some embodiments, the composition comprises at least two supports wherein a first capture antibody and detection antibody pairing of a first support is different from a second capture antibody and detection antibody pairing of a second support.

In an aspect, further disclosed is a colocalization-by-linkage composition for the detection or quantification of post-translational modifications (PTMs) within in a sample, the colocalization-by-linkage composition comprising:
- a) a CLA structure comprising;
  - i. a support
  - ii. a capture agent attached to the support;
  - iii. a detection agent anchor polynucleotide attached to the support, wherein the anchor polynucleotide comprises an anchor sequence; and
  - iv. a detection agent linked to a hook polynucleotide and an anchor-binding sequence complementary to at least a portion of the anchor sequence, wherein the detection agent is releasably bound to the detection agent anchor polynucleotide;
  - v. a detectably-labeled displacement agent capable of releasing the detection agent from the detection reagent anchor polynucleotide;

wherein the capture agent and the detection agent can simultaneously bind the analyte. In some embodiments, the detection agent recognizes an analyte comprising a post-translational modification. In some embodiments, the capture agent recognizes an analyte comprising a post-translational modification. In some embodiments, the composition further comprises:
- a) a first CLA structure comprising a first detection agent; and
- b) a second CLA structure comprising a second detection agent;

wherein the first agent recognizes an analyte without the post-translational modification and the second agent recognizes the presence of the post-translational modification on the analyte.

In some embodiments, the composition further comprises at least a third CLA structure comprising a third detection agent wherein the third and the second agent recognize different different-posttranslational modifications on the analyte.

In some embodiments, the CLA structure further comprises:
- a) a PTM detection agent anchor polynucleotide attached to the support, wherein the PTM anchor polynucleotide comprises a PTM anchor sequence;
- b) and a PTM detection agent linked to a PTM hook polynucleotide and a PTM anchor-binding sequence complementary to at least a portion of the PTM anchor sequence, wherein the PTM detection agent is releasably bound to the PTM detection agent anchor polynucleotide; and
- c) a PTM detectably-labeled displacement agent capable of releasing the PTM detection agent from the second detection reagent anchor polynucleotide;

wherein the PTM detection agent recognizes the presence of a post-translational modification and at the capture agent and the PTM detection agent can simultaneously bind the analyte.

In some embodiments, the capture agent is attached to the support via a capture anchor polynucleotide. In some embodiments, the capture agent and/or the detection agent is an antibody molecule. In some embodiments, the hook polynucleotide comprises a barcode sequence.

Disclosed herein is a method for detecting and/or quantifying post-translational protein modifications (PTMs) within in a sample, the method comprising:

- a) contacting the sample with the CLA structure;
- b) adding the detectably-labeled displacement agent and releasing the detection agent from the detection agent anchor polynucleotide; and
- c) detecting the presence or absence of the detectably-labeled displacement agent.

In an aspect, disclosed is a composition for increasing the signal lifetime of a colocalization-by-linkage assay, the composition comprising:
- a) a CLA structure comprising
  - i. a support;
  - ii. a capture agent attached to the support;
  - iii. a detection agent anchor polynucleotide attached to the support, wherein the anchor polynucleotide comprises an anchor sequence; and
  - iv. a detection agent linked to a hook polynucleotide and an anchor-binding sequence complementary to at least a portion of the anchor sequence, wherein the detection agent is releasably bound to the detection agent anchor polynucleotide;
- b) a detectably-labeled displacement polynucleotide capable of releasing the detection agent from the detection reagent anchor polynucleotide; and
- c) a bridge polynucleotide capable of hybridizing the hook strand and/or the displacement polynucleotide to the support;

wherein the capture agent and the detection agent can simultaneously bind the analyte. In some embodiments, the hook polynucleotide further comprises a bridge sequence and the bridge polynucleotide comprises a first region complementary to the bridge sequence and second region complementary to the anchor sequence. In some embodiments, the detectably-labeled displacement polynucleotide further comprises a bridge sequence and the bridge polynucleotide comprises a first region complementary to the bridge sequence and second region complementary to the anchor sequence.

In an aspect, disclosed herein is a colocalization-by-linkage composition for the detection or quantification of an analyte in a sample, the colocalization-by-linkage composition comprising:
- d. A CLA structure comprising:
  - i. a support;
  - ii. a capture agent attached to the support;
  - iii. a detection agent anchor polynucleotide attached to the support, wherein the anchor polynucleotide comprises an anchor sequence; and
  - iv. a detection agent linked to a hook polynucleotide and an anchor-binding sequence complementary to at least a portion of the anchor sequence, wherein the detection agent is releasably bound to the detection agent anchor polynucleotide;
- e. a detectably-labeled displacement agent capable of releasing the detection agent from the detection reagent anchor polynucleotide;

wherein the capture agent and the detection agent can simultaneously bind the analyte.

Further disclosed is a method for detecting and quantifying an analyte within a sample, the method comprising:
- a) contacting the sample with a CLA structure that comprises:
  - i. a support;
  - ii. a capture agent attached to the support;
  - iii. a detection agent anchor polynucleotide attached to the support, wherein the anchor polynucleotide comprises an anchor sequence; and
  - iv. a detection agent linked to a hook polynucleotide and an anchor-binding sequence complementary to at least a portion of the anchor sequence, wherein the detection agent is releasably bound to the detection agent anchor polynucleotide;

b) adding a detectably-labeled displacement agent that binds the hook polynucleotide and releases the detection agent and the hook polynucleotide from the detection agent anchor polynucleotide;

c) detecting a signal indicating a presence or absence of the detectably-labeled displacement agent indicating the presence or absence of the detection agent bound to the analyte; and d) normalizing the signal by detecting a control signal generated from normalization microparticles.

In an aspect, disclosed is a barcoded colocalization-by-linkage composition for the detection or quantification of an analyte in a sample, the colocalization-by-linkage composition comprising:

f. a CLA structure comprising;

i. a support comprising;

ii. a capture agent attached to the support;

iii. a detection agent anchor polynucleotide attached to the support, wherein the anchor polynucleotide comprises an anchor sequence; and iv. a detection agent linked to a hook polynucleotide that comprises a detection barcode polynucleotide and an anchor-binding sequence complementary to at least a portion of the anchor sequence, wherein the detection agent is releasably bound to the detection agent anchor polynucleotide; and g. a detectably-labeled displacement agent capable of releasing the detection agent from the detection reagent anchor polynucleotide;

wherein the capture agent and the detection agent can simultaneously bind the analyte; and wherein the detection barcode polynucleotide can be processed to identify the detection antibody In some embodiments, the detection barcode is releasable from the detection agent. In some embodiments, the CLA structure further comprises a releasable barcode, wherein the releasable barcode can be processed with the detection barcode. In some embodiments, the capture agent comprises a capture barcode polynucleotide, wherein the capture barcode can be processed with the detection barcode. In some embodiments, the capture barcode is releasable. In some embodiments, the barcode polynucleotide can be processed by a hybridization reaction. In some embodiments, the barcode polynucleotide can be processed by a sequencing reaction. In some embodiments, the barcode polynucleotide can be processed by an HCR reaction. In some embodiments, the detection barcode can be processed by a PCR reaction. In some embodiments, the detection barcode can be processed by a ligation reaction.

In another aspect, disclosed is a method for detecting and quantifying an analyte within a sample, the method comprising:

a) contacting the sample with CLA structure that comprises:

i. a support, ii. a capture agent attached to the support;

iii. a detection agent anchor polynucleotide attached to the support, wherein the anchor polynucleotide comprises an anchor sequence and a releasable barcode sequence attached to the support; and iv. a detection agent linked to a hook polynucleotide that comprises a detection barcode sequence and an anchor-binding sequence complementary to at least a portion of the anchor sequence, wherein the detection agent is releasably bound to the detection agent anchor polynucleotide;

b) adding a detectably-labeled displacement agent that binds the hook polynucleotide and releases the detection agent and the hook polynucleotide from the detection agent anchor polynucleotide;

c) detecting the presence or absence of the detectably-labeled displacement agent indicating the presence or absence of the detection agent bound to the analyte;

d) ligating the detection barcode and the releasable barcode to generate a CLA barcode; and e) identifying and/or processing the CLA barcode.

In some embodiments, the CLA structure after (c). In some embodiments, the detection barcode is releasable from the detection agent. In some embodiments, the detection barcode identifies the detection agent. In some embodiments, the releasable barcode identifies the capture agent. In some embodiments, the releasable barcode identifies the analyte. In some embodiments, the releasable barcode identifies the capture agent and the analyte. In some embodiments, identifying the CLA barcode is performed by a sequencing reaction. In some embodiments, the identifying CLA barcode is performed by a hybridization reaction. In some embodiments, identifying the CLA barcode is performed by a PCR reaction. In some embodiments, identifying the CLA barcode is performed by an HCR reaction.

In another aspect, disclosed is a method for amplifying a CLA signal, the method comprising:

a) contacting the sample with CLA structure that comprises:

i. a capture agent attached to the support;

ii. a detection agent anchor polynucleotide attached to the support, wherein the anchor polynucleotide comprises an anchor sequence and a releasable barcode sequence attached to the support; and iii. a detection agent linked to a hook polynucleotide that comprises a detection barcode sequence and an anchor-binding sequence complementary to at least a portion of the anchor sequence, wherein the detection agent is releasably bound to the detection agent anchor polynucleotide;

b) adding a detectably-labeled displacement agent that comprises an HCR imitating label and binds the hook polynucleotide and releases the detection agent and the hook polynucleotide from the detection agent anchor polynucleotide; and c) adding a labeled HCR hairpin to the product of (b);

d) detecting the presence or absence of the detectably-labeled displacement agent indicating the presence or absence of the detection agent bound to the analyte.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

For a better understanding of the invention and to show more clearly how it may be carried into effect, reference will now be made by way of example to the accompanying drawings, which illustrate aspects and features according to embodiments of the present invention, and in which:

FIG. 18 discloses SEQ ID NOS 2-13, 15, 14, 10, 10, 2, 2, and 4, respectively, in order of appearance.

DETAILED DESCRIPTION

Figure 1:
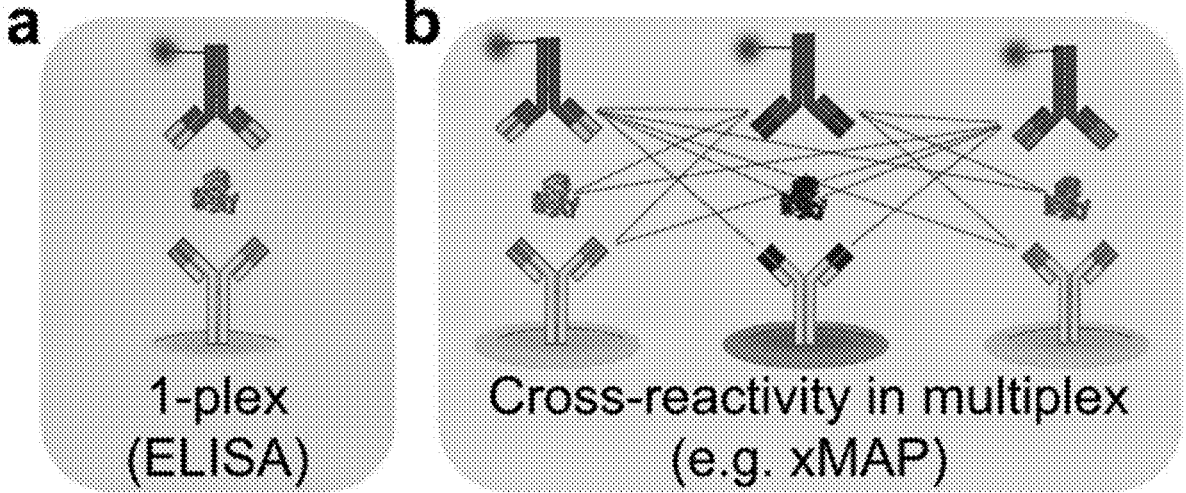
FIG. 1 is a schematic diagram that illustrates in (a) a typical ELISA reaction where only one antibody pair is used (1-plex or singleplex assay); and in (b) cross-reactivity in multiplex analysis produced by non-specific binding events which occur between target biomolecules and mixed AB pairs (depicted as antibody pairs in the figure).

There are provided systems and methods for detecting and/or quantifying one or more analyte using a colocalization-by-linkage assay, as described herein. In particular, there are provided systems and methods having sufficiently low background signal, sufficiently low cross-reactivity between reagents, and/or sufficiently high sensitivity to allow detection and/or quantitation of multiple biomolecules simultaneously in a sample. There are also provided multiplex sandwich assays that are rapid, sensitive, cost-effective, and/or scalable, and methods for their preparation.

It should be understood that this disclosure is not limited to specific devices, systems, methods, or uses or process steps, and as such they may vary.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used herein, the term "about" in the context of a given value or range refers to a value or range that is within 20%, preferably within 10%, and more preferably within 5% of the given value or range.

As used herein, the term "and/or" is to be taken as specific disclosure of each of the two specified features or components with or without the other. For example "A and/or B" is to be taken as specific disclosure of each of (i) A, (ii) B and (iii) A and B, just as if each were set out individually herein.

As used herein, the term "support" refers to an immobilizing structure, surface or substrate, such as without limitation a microparticle, a nanoparticle, a well in a plate, a porous polymer, or a hydrogel. It should be understood that the support is not meant to be particularly limited, and any solid, semi-solid, gel or gel-like structure may be used. For example, a support may be an array, a bead (such as without limitation a polystyrene bead), the surface of a multi-well plate (such as a 96-well plate, a 384-well plate, etc.), the surface of a glass slide, a hydrogel matrix, a microfluidic chip, a lateral flow strip, a glass surface, a plastic surface, a silicon surface, a ceramic surface, and the like. In one embodiment, the support is a bead or microparticle or nanoparticle, typically micron-sized or nano-sized, such as without limitation a polystyrene bead, a magnetic bead, a paramagnetic bead, a plastic bead, etc. In another embodiment, the support is a planar microarray. In an embodiment, the support is a nanoparticle. In an embodiment, the support is a microparticle.

In some embodiments, the bead may contain molecular precursors (e.g., monomers or polymers), which may form a polymer network via polymerization of the precursors. In some embodiments, a precursor may be an already polymerized species capable of undergoing further polymerization via, for example, a chemical cross-linkage. In some embodiments, a precursor comprises one or more of an acrylamide or a methacrylamide monomer, oligomer, or polymer. In some embodiments, the bead may comprise prepolymers, which are oligomers capable of further polymerization. For example, polyurethane beads may be prepared using pre-polymers. In some embodiments, the bead may contain individual polymers that may be further polymerized together. In some embodiments, beads may be generated via polymerization of different precursors, such that they comprise mixed polymers, co-polymers, and/or block co-polymers.

A bead may comprise natural and/or synthetic materials. For example, a polymer can be a natural polymer or a synthetic polymer. In some embodiments, a bead comprises both natural and synthetic polymers. Examples of natural polymers include proteins and sugars such as deoxyribonucleic acid, rubber, cellulose, starch (e.g., amylose, amylopectin), proteins, enzymes, polysaccharides, silks, polyhydroxyalkanoates, chitosan, dextran, collagen, carrageenan, ispaghula, acacia, agar, gelatin, shellac, sterculia gum, xanthan gum, Corn sugar gum, guar gum, gum karaya, agarose, alginic acid, alginate, or natural polymers thereof. Examples of synthetic polymers include acrylics, nylons, silicones, spandex, viscose rayon, polycarboxylic acids, polyvinyl acetate, polyacrylamide, polyacrylate, polyethylene glycol, polyurethanes, polylactic acid, silica, polystyrene, polyacrylonitrile, polybutadiene, polycarbonate, polyethylene, polyethylene terephthalate, poly(chlorotrifluoroethylene), poly(ethylene oxide), poly(ethylene terephthalate), polyethylene, polyisobutylene, poly(methyl methacrylate), poly(oxymethylene), polyformaldehyde, polypropylene, polystyrene, poly(tetrafluoroethylene), poly(vinyl acetate), poly(vinyl alcohol), poly(vinyl chloride), poly(vinylidene dichloride), poly(vinylidene difluoride), poly(vinyl fluoride) and combinations (e.g., co-polymers) thereof. Beads may also be formed from materials other than polymers, including lipids, micelles, ceramics, glass-ceramics, material composites, metals, other inorganic materials, and others.

As will be appreciated, polynucleotides and/or barcodes that are releasably, cleavably or reversibly attached to the beads described herein include polynucleotides and/or barcodes that are released or releasable through cleavage of a linkage between the polynucleotide and/or barcode molecule and the bead allowing the polynucleotides or barcodes to be accessed or accessible by other reagents, or both.

In addition to thermally cleavable bonds, disulfide bonds and UV sensitive bonds, other non-limiting examples of labile bonds that may be coupled to a precursor or bead include an ester linkage (e.g., cleavable with an acid, a base, or hydroxylamine), a vicinal diol linkage (e.g., cleavable via sodium periodate), a Diels-Alder linkage (e.g., cleavable via heat), a sulfone linkage (e.g., cleavable via a base), a silyl ether linkage (e.g., cleavable via an acid), a glycosidic linkage (e.g., cleavable via an amylase), a peptide linkage (e.g., cleavable via a protease), or a phosphodiester linkage (e.g., cleavable via a nuclease (e.g., DNAase)).

Beads may be of uniform size or heterogeneous size. In some embodiments, the diameter of a bead may be about 1 μm, 5 μm, 10 μm, 20 μm, 30 μm, 40 μm, 50 μm, 60 μm, 70 μm, 80 μm, 90 μm, 100 μm, 250 μm, 500 μm, or 1 mm. In some cases, a bead may have a diameter of at least about 1 μm, 5 μm, 10 μm, 20 μm, 30 μm, 40 μm, 50 μm, 60 μm, 70 μm, 80 μm, 90 μm, 100 μm, 250 μm, 500 μm, 1 mm, or more. In some cases, a bead may have a diameter of less than about 1 μm, 5 μm, 10 μm, 20 μm, 30 μm, 40 μm, 50 μm, 60 μm, 70 μm, 80 μm, 90 μm, 100 μm, 250 μm, 500 μm, or 1 mm. In some cases, a bead may have a diameter in the range of about 40-75 μm, 30-75 μm, 20-75 μm, 40-85 μm, 40-95 μm, 20-100 μm, 10-100 μm, 1-100 μm, 20-250 μm, or 20-500 μm.

In certain aspects, beads are provided as a population or plurality of beads having a relatively monodisperse size distribution. Where it may be desirable to provide relatively consistent amounts of reagents within partitions, maintaining relatively consistent bead characteristics, such as size, can contribute to the overall consistency.

As used herein, the term "analyte" refers to a targeted biomolecule or biological cell of interest which is being identified, detected, measured and/or quantified. An analyte may be any biomolecule or biological cell which can be detected using the systems and methods provided herein, such as without limitation proteins, nucleic acids (DNAs, RNAs, etc.), antibodies, antigens, proteins, cells, chemicals, biomarkers, enzymes, polypeptides, amino acids, polymers, carbohydrates, multi-protein complexes, exosomes, oligonucleotides, low molecular weight compounds, and the like. Non-limiting examples of analytes include antibodies, antibody fragments (e.g., scFv, Fab, etc.), aptamers, modified aptamers, somamers, affimers, antigens, proteins, polypeptides, multi-protein complexes, exosomes, oligonucleotides, and low molecular weight compounds.

As used herein, a "sample" refers to any fluid or liquid sample which is being analyzed in order to detect and/or quantify an analyte. In some embodiments, a sample is a biological sample. Examples of samples include without limitation a bodily fluid, an extract, a solution containing proteins and/or DNA, a cell extract, a cell lysate, or a tissue lysate. Non-limiting examples of bodily fluids include urine, saliva, blood, serum, plasma, cerebrospinal fluid, tears, semen, sweat, pleural effusion, liquified fecal matter, and lacrimal gland secretion.

The term "barcode," as used herein, generally refers to a label, or identifier, that can be part of an analyte to convey information about the analyte. A barcode can be a tag attached to an analyte (e.g., nucleic acid molecule) or a combination of the tag in addition to an endogenous characteristic of the analyte (e.g., size of the analyte or end sequence(s)). The barcode may be unique. Barcodes can have a variety of different formats, for example, barcodes can include: polynucleotide barcodes; random nucleic acid and/or amino acid sequences; and synthetic nucleic acid and/or amino acid sequences. A barcode can be attached to an analyte in a reversible or irreversible manner. The barcode can be added to, for example, a fragment of a deoxyribonucleic acid (DNA) or ribonucleic acid (RNA) sample before, during, and/or after sequencing of the sample. Barcodes can allow for identification and/or quantification of individual sequencing-reads in real time. In some examples, the barcode is generated in a combinatorial manner. Any polynucleotide sequence can comprise a barcode sequence and be used with methods, devices and systems of the present disclosure. The nucleic acid barcode sequences can include from 6 to about 20 or more nucleotides within the sequence of the oligonucleotides. In some embodiments, the length of a barcode sequence may be 6, 7, 8, 9, 10, 11, 12, 13, 14, 15, 16, 17, 18, 19, 20 nucleotides or longer. In some embodiments, the length of a barcode sequence may be at least 6, 7, 8, 9, 10, 11, 12, 13, 14, 15, 16, 17, 18, 19, 20 nucleotides or longer. In some embodiments, the length of a barcode sequence may be at most 6, 7, 8, 9, 10, 11, 12, 13, 14, 15, 16, 17, 18, 19, 20 nucleotides or shorter. These nucleotides may be completely contiguous, i.e., in a single stretch of adjacent nucleotides, or they may be separated into two or more separate subsequences that are separated by 1 or more nucleotides. In some embodiments, separated barcode subsequences can be from about 4 to about 16 nucleotides in length. In some embodiments, the barcode subsequence may be 4, 5, 6, 7, 8, 9, 10, 11, 12, 13, 14, 15, 16 nucleotides or longer. In some embodiments, the barcode subsequence may be at least 4, 5, 6, 7, 8, 9, 10, 11, 12, 13, 14, 15, 16 nucleotides or longer. In some embodiments, the barcode subsequence may be at most 4, 5, 6, 7, 8, 9, 10, 11, 12, 13, 14, 15, 16 nucleotides or shorter.

As used herein, the term "encoded microparticle" refers to a micron-sized microparticle that is encoded spectrally according to either the target analyte or the specific test that is to be performed in the assay.

As used herein, the term "non-specific binding" refers to an unintended reaction between reagents and/or molecules within the sample, including but not limited to reaction between non-cognate antibodies and protein sticking through hydrophobic interactions.

As used herein, the terms "affinity binder" (AB), "binder", and "reactant" are used interchangeably to mean any molecule capable of specifically recognizing a target analyte, e.g., via a non-covalent interaction. Examples of affinity binders (ABs) include without limitation immunoglobulin-G (IgG) antibodies (e.g., whole molecules or Fab fragments), aptamers, affimers, nanobodies, ankyrins, and single-chain variable fragments (scFvs).

As used herein, the term "sandwich assay" is used to mean an analyte-targeting assay wherein two ABs simultaneously bind the target analyte of interest and can be used to detect and/or quantify it.

As used herein, the terms "multiplex sandwich assay", "multiplexed sandwich assay" and "MSA" are used interchangeably to mean a sandwich assay that targets multiple (e.g., two or more) analytes from the same sample and/or assay volume at the same time, multiple AB pairs being used in the assay system at the same time.

As used herein, the term "cross-reactivity" is used to mean a particular case of non-specific binding or non-specific reaction in a multiplexed sandwich assay, wherein an unintended complex is formed that includes non-cognate affinity binders, e.g., as shown in FIG. 1.

As used herein, the terms "capture affinity binder", "cAB", "capture AB", "capture binder" and "capture reagent" are used interchangeably to refer to an AB that is attached to a support in a biomolecule complex and is not released from it. A capture AB may be attached directly to a support (e.g., via a covalent bond, a biotin-streptavidin bond, a DNA oligonucleotide linker, or a polymer linker) or indirectly (e.g., via linkage to an anchor strand, e.g., by conjugation or through a linker such as a capture strand). Non-limiting examples of capture reagents include antibodies, antibody fragments (e.g., scFv, Fab, etc.), aptamers, modified aptamers (such as slow off-rate modified aptamers or somamers), affimers, antigens, proteins, polypeptides, multi-protein complexes, exosomes, oligonucleotides, and low molecular weight compounds.

The term "capture strand" refers to a linker (e.g., an oligonucleotide, a polymer, etc.) that links a capture reagent to an anchor strand (and hence the support to which the anchor strand is attached).

As used herein, the terms "detection affinity binder", "dAB", "detection AB", "detection binder" and "detection reagent" are used interchangeably to refer to an AB in a biomolecule complex that is releasably attached to a support. The dAB is generally used for signal transduction and assay signalling. In some embodiments of methods and systems provided herein, for example, the fraction of dAB unbound to an analyte is released from the support such that no signal is produced in the absence of bound analyte. In some embodiments, the dAB is bound to a label or means for signal transduction and assay signalling. Non-limiting examples of detection reagents include antibodies, antibody fragments (e.g., scFv, Fab, etc.), aptamers, modified aptamers, somamers, affimers, antigens, proteins, polypeptides, multi-protein complexes, exosomes, oligonucleotides, and low molecular weight compounds.

As used herein, the term "anchor strand" refers to a linker that attaches to an immobile point on a support. Non-limiting examples of anchor strands include polymers, such as polyethylene glycol (PEG), oligonucleotides (such as a single-stranded DNA oligonucleotide, a single-stranded RNA oligonucleotide, or a double-stranded DNA or RNA oligonucleotide, or a DNA-RNA hybrid), and oligosaccharides.

In some cases, an anchor strand can be greater than about 5 nucleotides in length, greater than about 10 nucleotides in length, greater than about 20, 30, 40, 50, 60, 70, 80, 90, 100, 120, 150 or even 200 nucleotides in length. In some cases, an anchor strand may be less than about 250 nucleotides in length, less than about 200, 180, 150, 120 100, 90, 80, 70, 60, 50, 40, or even 30 nucleotides in length As used herein, the term "hook strand" refers to a linker that links a detection AB to an anchor strand and hence attaches it to a support. The hook strand is typically attached releasably to the anchor strand, e.g., in such a way that the attachment can be released. Generally, when the attachment between the hook strand and the anchor strand is released, the fraction of detection AB linked to the hook strand that is not bound to a target analyte will be released from the anchor strand, and therefore also released from the support, such that no signal from the detection AB can be detected on the support in the absence of the target analyte. In this way, signal on the support is only detected when the target analyte is present and bound by the detection AB and the capture AB.

In some cases, a hook strand can be greater than about 5 nucleotides in length, greater than about 10 nucleotides in length, greater than about 20, 30, 40, 50, 60, 70, 80, 90, 100, 120, 150 or even 200 nucleotides in length. In some cases, a hook strand may be less than about 250 nucleotides in length, less than about 200, 180, 150, 120 100, 90, 80, 70, 60, 50, 40, or even 30 nucleotides in length In some embodiments, where a label is on the hook strand and/or the detection reagent and is only activated or detectable after the release of the hook strand and/or the detection reagent from the anchor strand, the signal is "release-dependent", as it will only be detectable after the release of the hook strand and/or the detection reagent from the anchor strand. Similarly, in some embodiments, where the label is on a displacer agent hybridizing to the hook strand, the signal is "displacement-dependent".

As used herein, the term "displacer agent" refers to an agent that directly or indirectly causes or initiates release of the releasable linkage between the anchor strand and the hook strand, thereby releasing the hook strand (and the detection AB linked thereto) from the support. The mechanism used by the displacer agent is not particularly limited. For example, the displacer agent may directly or indirectly cause or initiate cleavage, displacement, or unbinding of the linkage between the anchor strand and the hook strand; other mechanisms are possible and are also contemplated. In some embodiments, the hook strand is displaced from the anchor strand using a DNA oligonucleotide that hybridizes to the hook strand and/or the anchor strand. Examples of displacer agents include but are not limited to a displacement DNA oligonucleotide, a source of mono- or poly-chromatic light, a restriction enzyme, and a reducing agent such as dithiothreitol (DTT). In some embodiments, where photocleavable DNA segments are used, the displacer agent may be a light which effects release via a photocleavage reaction. In some embodiments, the displacer agent is labeled, e.g., with a dye, a fluorophore, a specific DNA sequence, an enzyme, a biotin moiety, and the like. When the displacer agent is labeled, it can serve the dual-function of releasing the hook strand and labelling it simultaneously.

As used herein, the term "label" refers to any molecule or a portion of a molecule that generates a signal, can be targeted with a signal-generating molecule, or is otherwise detectable. Examples of labels include but are not limited to biotin, fluorophores, enzymes, enzyme substrates, and specific DNA sequences. An "inactive" or "undetectable" label refers to a label which is not active, is masked, or is otherwise undetectable, e.g., not capable of generating a detectable signal, such as without limitation a quenched fluorescent dye.

It should be understood that systems and methods provided herein can be used in virtually any type of sandwich assay wherein two sets of ABs are used. However, for simplicity, specific embodiments of the present invention are presented herein using whole-molecule Immunoglobulin-G antibodies (IgG) as ABs, which represents one of many possible embodiments. It should be understood that antibodies are not limited to whole-molecule IgG and that many different antibodies, antibody fragments, etc. can be used. Further, ABs are not limited to antibodies. Similarly, many different types of sandwich assays other than the specific ones described herein can be used.

Figure 4:
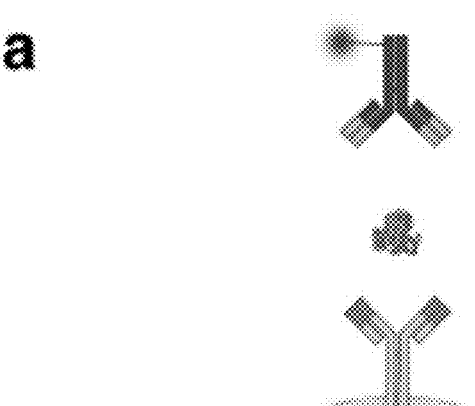
FIG. 4 shows a schematic diagram that illustrates in (a) a typical ELISA reaction where only one antibody pair is used (1-plex or singleplex assay); and in (b) cross-reactivity in multiplex analysis produced by non-specific binding events which occur between target biomolecules and mixed AB pairs (depicted as antibody pairs in the figure). (c) shows a CLA system in which cross-reactivity is prevented by colocalizing antibody pairs on individual beads using DNA linkages.
Figure 4:
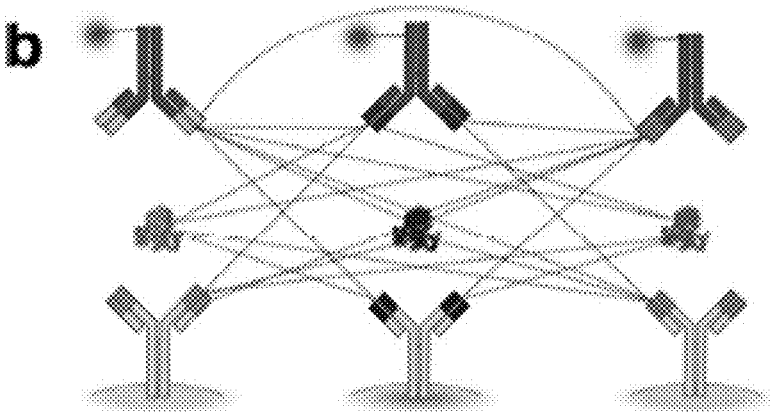
Figure 4:
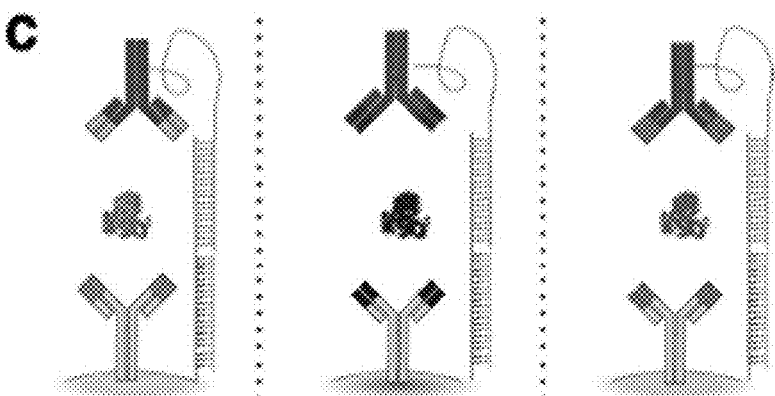

In some embodiments, there is provided a dual-AB or sandwich assay that can avoid cross-reactivity by colocalizing two ABs (a capture AB and a detection AB) on a support prior to exposure to a biological sample containing an analyte of interest. Colocalization on the support does not permit any mixing of different AB pairs prior to exposure to the analyte, and can thus reduce or eliminate cross-reactivity between reagents and/or background (such as that shown in FIG. 1 or FIG. 4). In an embodiment, there is provided a support attached to a mixture of capture and detection ABs, where each set of capture and detection ABs is capable of binding with an analyte of interest, with the detection AB attached to the support, optionally via a releasable linker. In an embodiment, there is provided a support attached to a mixture of capture and detection ABs, wherein each analyte is capable of binding simultaneously to both a capture AB and a detection AB, and wherein the detection AB is releasably attached to the support, optionally via a releasable hook strand. Upon release of the detection reagent and/or the hook strand, the corresponding detection AB remains on the support only if bound to the analyte in a tertiary complex with a capture AB.

It should be understood that "linkers" and "strands" used in methods and systems provided herein are not particularly limited. Non-limiting examples of linkers and strands include DNA oligonucleotides (also referred to as DNA oligos), polymers, polysaccharides, and the like. DNA linkages can be covalent, such as conjugation between a hook strand oligo and a detection AB, or non-covalent, such as hybridization or base-stacking between two complementary DNA sequences. To allow formation of a capture AB-antigen-detection AB tertiary complex, the hook strand is designed to have a flexible, single-stranded portion. Displacement of a DNA linkage can be performed using several methods including but not limited to a toe-hold mediated DNA displacement reaction, enzymatic cleavage, and photo-activated cleavage. Specific DNA sequences can also be used as labels, which can be either directly targeted using a complementary sequence that is fluorescently labeled, can be used as amplification triggers or primers through a hybridization-chain reaction or a polymerase-chain reaction, and can be read-out via sequencing.

It should be understood that "oligonucleotides" (also referred to as "oligos") used in methods and systems provided herein are not particularly limited. For example, oligos can be modified using fluorescent dyes on 5' or 3' termini, modified with a photocleavable phosphodiester back-bone, conjugated to a protein, a biotin, or an enzyme, etc.

These embodiments may also be referred to herein as a "Colocalization-by-Linkage Assay" or "CLA". In some embodiments of CLA, the detection AB is labeled (i.e., attached to a label). In some embodiments of CLA, the hook strand linking the detection AB to the anchor strand is labeled (i.e., attached to a label). Generally the label attached to the detection AB or the hook strand is inactive or undetectable, such that the label can be detected after release of the detection AB from the support (i.e., after the hook strand is released from the anchor strand). Signal detection from the label is thus release-dependent (also referred to, in some embodiments, as "displacement-dependent"). In this way, only detection ABs bound to the analyte in a tertiary complex with a capture AB and released from the anchor strand will be detected, as unbound detection AB will be released from the support (and can be removed e.g., by washing). Background signal may also be reduced since the label is inactive or undetectable prior to release, or if a given hook strand is not released (i.e., due to the release-dependent or displacement-dependent nature of the signal). In some embodiments, therefore, methods and systems provided herein may be referred to as "release-dependent transduction" (or "RDT") or "displacement-dependent detection", to reflect the release-dependent (or displacement-dependent) signal transduction.

Conventional sandwich assays generally rely on the presence of detection ABs to transduce a signal and detect the presence of an analyte. Similarly, in certain embodiments of systems and methods presented herein, the detection AB and/or the hook strand can act as signal transducers. However, in contrast to conventional assays, in systems and methods provided herein the detection AB and/or the hook strand optionally linked thereto can remain on the support only when a tertiary complex is formed with the analyte and the capture AB. It will be appreciated that, if the detection reagent and/or the hook strand is not successfully or completely released from the anchor strand, then it can remain on the support even in the absence of the analyte. In this case, if the detection AB and/or the hook strand is attached to a label that is active or detectable even when attached to the anchor strand, then any non-released, labeled detection AB and/or hook strand would transduce a signal. In other words, in that case, any labeled and non-released detection reagent and/or hook strand could result in a signal independent of the presence of the analyte, contributing to non-specific background signal, and reducing assay performance and/or sensitivity. It will be appreciated that the background signal in that case will be proportional to the fraction of non-released detection reagents and/or hook strands. It should also be appreciated that near-complete release of complexes from supports may be difficult to achieve due to steric hindrance, sticking, and/or incomplete washing. However, release-dependent transduction (RDT) can minimize or eliminate these problems, as no signal transduction occurs if the release of the detection reagent and/or the hook strand from the anchor strand is not complete, as demonstrated in FIG. 24.

In some embodiments, therefore, systems and methods provided herein include an additional level of redundancy to reduce background signal and/or increase sensitivity by the use of release-dependent transduction (RDT). In RDT, signal transduction occurs only if both of the following conditions are satisfied: (i) formation of a tertiary capture AB-analyte-detection AB complex, and (ii) release of the corresponding detection AB and/or hook strand from the anchor strand. In such cases, a non-released detection AB and/or hook strand will not contribute to the background signal. This signal transduction mechanism, which we herein refer to as "release-dependent transduction (RDT)", can be achieved through various means. For example, some embodiments can include a label on the hook strand, wherein the label is inactive or undetectable until after the release from the anchor strand, such that a non-released (e.g., non-displaced) hook strand and/or detection AB) will not contribute to or transduce the signal.

In some embodiments of RDT, a hook strand is labeled with a fluorescent dye quenched by a quencher on the anchor or another proximal strand, such that release results in unquenching or activation of the fluorescent dye.

In some embodiments of RDT, the detection reagent and the hook strand are not labeled, and instead the displacer agent is labeled. In this case, the displacer agent hybridizes to the hook strand, displacing it from the anchor strand, and simultaneously labeling it. If the detection AB is not bound to analyte and capture AB in a tertiary complex, then the hook strand, the displacer agent, and the label are washed off the support. Since the label is attached to the displacer agent, the label is only present on the support when both conditions are met: (i) release or displacement from the anchor strand has occurred, and (ii) analyte has bound to both capture and detection ABs (shown in FIG. 7, for example).

It will be appreciated that other embodiments of RDT are possible, and the mechanism of RDT is not meant to be particularly limited.

Figure 6:
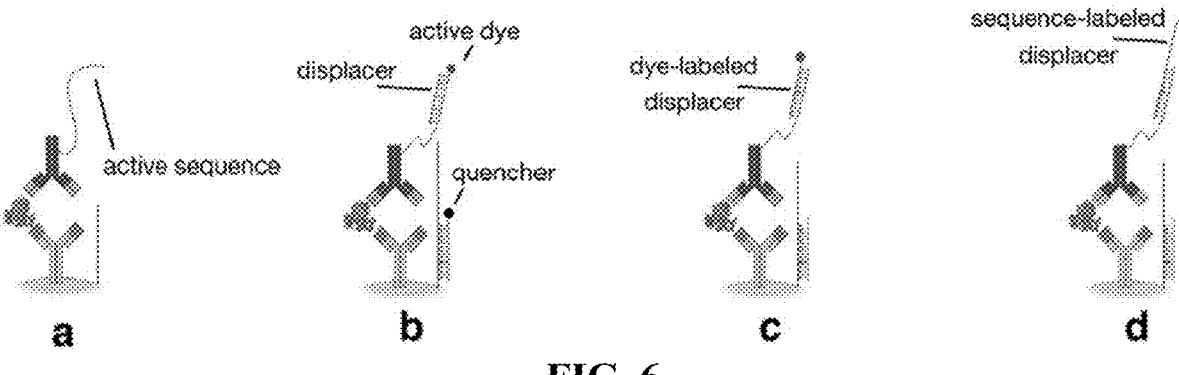
FIG. 6 shows a schematic diagram illustrating exemplary embodiments of detection CLA in the presence of the analyte, after a successful displacement reaction. (a) Label is a specific DNA sequence on the hook strand that can be targeted via DNA hybridization for detection. (b) Displacer agent is used to release hook strand oligo from the anchor strand, resulting in activation of the label attached to the hook strand (in this case, unquenching of a dye after release). (c) Dye-labeled displacer agent binds preferentially to the hook strand oligo, releasing it from the anchor strand, and simultaneously labeling both the hook strand and the bound tertiary complex. (d) Sequence-labeled displacer agent binds preferentially to the hook strand oligo, releasing it from the anchor strand, and simultaneously labeling both the hook strand and the bound tertiary complex.

In some embodiments of RDT, the detection AB or the anchor strand is attached to a label. In some embodiments, the hook strand linking the detection AB to the anchor strand is labeled (i.e., attached to a label). Generally the label attached to the detection AB, the anchor strand, or the hook strand is inactive or undetectable, such that the label can only be detected after release of the detection AB from the support (i.e., after the hook strand is released from the anchor strand, as shown for example in FIG. 6). In this way, the only detection AB-hook oligo complexes that are detected are the ones with a detection AB bound to the analyte in a tertiary complex with a capture AB and a hook strand successfully released from the anchor strand. Otherwise, unbound detection AB will be released from the support (and can be removed e.g., by washing), and all non-released strands are not detected, whether or not the analyte was bound. In this way, background signal from non-released detection ABs and/or hook strands is mitigated, ensuring a low background signal and/or high sensitivity detection.

In other embodiments of RDT, the hook strand contains a label that remains inactive or undetectable until the hook strand is released from the anchor strand. For example, this can be achieved when the hook strand and the anchor strand are DNA oligonucleotides bound together via hybridization, wherein the hook strand contains a DNA sequence label normally hybridized to the anchor strand and hence unavailable for binding, or undetectable. Release of the hook strand oligo from the anchor strand oligo reveals a detectable label on the hook strand. Such release can be achieved e.g., via enzymatic cleavage, DNA displacement, or photocleavage using light.

In some such embodiments, there is provided a release or displacer agent which is an oligonucleotide that displaces the anchor strand-hook strand hybrid by binding to the anchor strand oligo via a toe-hold displacement reaction. In an embodiment, the hook strand and the detection AB are both not labeled, and a labeled displacer agent (e.g., a fluorescently-labeled oligonucleotide) performs RDT through the dual-function of release (displacement) and labeling. In this way, through only labeling the displaced hook strands, a detectable signal/signal transduction only occurs on a support when two conditions are met (displacement of the hook strand and presence of the analyte), akin to an "AND" logical gate (shown in FIG. 7B, for example).

In some embodiments of assays and systems provided herein, one or more set of capture and detection ABs is attached to a support, each set being specific for an analyte of interest. In this way, the capture and the detection AB are pre-assembled and colocalized on the support, prior to exposure to a biological sample containing the analyte of interest. As described above, the detection AB is attached to the support releasably. In some embodiments, the detection AB is attached to the support by a releasable linker (a hook strand) which is linked to an anchor strand attached to the support. The hook strand is generally flexible and allows the detection AB to diffuse freely within the bounds allowed by the lengths of the hook strand and/or the anchor strand. The hook strand and the releasable link are not particularly limited and may vary in size, flexibility, structure, etc., as long as they allow simultaneous binding of the analyte by the detection AB and the capture AB. The capture AB and the detection AB generally bind separate regions of the analyte, although they may bind overlapping sites, as long as they are capable of binding the analyte simultaneously.

In some embodiments, the detection AB is linked to the support using a hook strand which is a DNA oligonucleotide that can bind specifically to the anchor strand attached to the support. After contacting and incubating with the biological sample (i.e., target recognition step), the detection AB is separated from the anchor strand by breaking the linkage between the hook strand and the anchor strand on the surface. This release the fraction of detection AB that has not formed a tertiary capture AB-analyte-detection AB complex. It should be understood that the linkage between the hook strand and the anchor strand may be released or broken in several ways, such as without limitation DNA strand displacement, enzymatic cleavage, photo-activated cleavage, and the like.

The CLA methods and systems described herein is amenable to the multiplexed detection of analytes. In some such embodiments, each set of supports include AB pairs specific to one target protein or analyte, and hence includes all the reagents necessary for capture and detection of the analyte. In some such embodiments, the design and nature of linkages on the supports as well as the displacer agents are homogenous across all targets. For example, in some such embodiments when the anchor, hook, and displacers consist of oligonucleotides of specific sequences, said sequence is homogenous across all target analytes. For further clarity, the displacer agent acts on all supports, regardless of the target analyte.

In some embodiments, the CLA methods and systems described herein can be implemented using hydrogel microparticles. CB and DB may be linked to the hydrogel network, but not necessarily within reach of each other, during sample incubation. After incubation, the displacer agent releases the DBs, allowing at least some of them to diffuse further within the hydrogel matrix and bind to other analytes and form the sandwich complex.

As encompassed herein, many ABs targeting many different analytes can be mixed in the same assay volume (i.e., multiplexing); interaction between different ABs on different supports (or between different ABs on different locations/positions on the same support) are limited by the linkages to the support(s), so that interaction between ABs from different supports/locations is avoided. This is in contrast to conventional multiplexing technologies that can not limit interactions between ABs when all ABs are mixed in solution. Further, with methods and systems described herein, different microparticle populations can be fabricated separately in large batches, each containing a different AB capture-detection pair needed to detect a specific antigen, ensuring that cross-reactivity does not occur during manufacturing.

In some embodiments, multiplexed CLA methods and systems can thus avoid the cross-reactivity scenarios shown in FIG. 1. For example, as will be appreciated by those skilled in the art, the colocalization of cognate capture and detection ABs on their respective supports (e.g., microparticles) will eliminate unwanted interactions such as, for example, binding between non-cognate detection and capture ABs. In addition to those scenarios shown in FIG. 1, those skilled in the art will recognize that, as opposed to conventional multiplexed sandwich assays, analytes that indiscriminately bind, or stick, to off-target supports cannot be detected by their cognate detection AB in methods and systems provided herein, and hence do not contribute to increase the background signal.

In some embodiments, on each support, the local concentrations of the capture and detection ABs can be high, which can serve to concentrate the analytes and increase the sensitivity. On the other hand, the total concentration of each capture and detection AB in the entire assay volume is only dependent on the concentration of target-specific supports (e.g., microparticles, microarray spots) and can be designed to yield low bulk-concentrations of detection ABs upon release. For example, while the local-concentrations can be in the micromolar range, the use of a low number of target-specific microparticles can yield bulk detection AB concentrations too low (<pM) to yield any off-target binding, as shown for example in FIG. 22. The bulk concentrations can be further decreased by increasing the volume during the release step. Thus, in certain embodiments, methods and systems provided herein can further avoid cross-reactivity that occurs after detection AB release, due to the low concentration or amount of detection AB used on the support.

In some embodiments, simultaneous binding of two colocalized binders (capture AB, detection AB) to two different epitopes of the same analyte (that is, increased binding avidity) can result in a much lower effective off-rate ($k_{off}$) in comparison to conventional sandwich assays where capture and detection ABs are added sequentially. After sample introduction and incubation, the supports in methods and systems provided herein can be stringently washed, since the analytes are bound with high avidity. Hence, in some embodiments of methods and systems provided herein, stringent washing can be used to reduce assay background and/or improve sensitivity and/or specificity. In some embodiments, it may be desirable to rapidly execute the assay steps following the release of a hook strand from an anchor strand and up until read-out of the assay signal, since off-binding of analytes can result in a reduced signal which can contribute to reduced sensitivity, although such effects are generally reduced in CLA.

In one embodiment of methods and systems provided herein, a support is an encoded micron-sized microparticle, and capture reagent and the detection reagent are both antibodies, wherein the capture reagent and its cognate detection reagent are colocalized on the surface of the same support using DNA linkages (in other words, the hook strand and the anchor strands are single-stranded DNA oligonucleotides, linked together via a double-stranded DNA hybrid). In some such embodiments, the detection reagent linked to the hook strand and the anchor strand are homogeneously mixed and attached to the surface of the microparticle, wherein the anchor strand is linked to the hook strand through partial hybridization, the hook strand being conjugated to the detection reagent, the hook strand being a flexible and releasable DNA linker. The hybrid between the anchor and hook strands is generally stable during conditions of sample incubation. In some embodiments, the capture reagent is also linked to the microparticle via a DNA linker as well. In some such embodiments, release of the hook strand from the anchor strand can be performed via a toe-hold mediated DNA displacement reaction. In such embodiments, a displacer agent is an oligonucleotide designed to bind to a toe-hold sequence on the hook strand to drive the displacement reaction forward. In some such embodiments, release of the hook strand from the anchor strand can be performed without a displacer agent, e.g., by raising the temperature so that the DNA hybrid "melts" or is unbound.

In an embodiment, a detection AB and/or a hook strand is labeled, e.g., with a dye, a biotin moiety that can be detected using a fluorescently-labeled streptavidin in a subsequent step etc. In certain embodiments, a detection AB can be detected after binding an analyte with a labeled-binder, for example, an IgG can be targeted using a labeled species-specific secondary-IgG. In some embodiments, the detection AB and the hook strand are not labeled, and instead a displacer agent used to release the hook strand from the anchor strand is labeled. In such embodiments, the labeled displacer agent attaches to the hook strand and/or the detection AB after the release of the hooks strand from the anchor strand.

In some embodiments, the label is a specific DNA sequence that can be detected or targeted in a subsequent step(s). For example, a specific DNA sequence can be targeted with a subsequent DNA hybridization step that labels it with a dye. In an embodiment, the specific DNA sequence is detected and amplified through Polymerase Chain Reaction (PCR) or other enzymatic DNA amplification means. Specific DNA sequences can also be cleaved and detected by other means such as sequencing. Embodiments using DNA sequence as a label are not limited and may include the sequence being part of the hook strand (and hence, initially inactive/undetectable), or present on the displacer agent (shown for example in FIGS. 6A, D).

In some embodiments, CLA reagents and systems can be constructed for the purpose of identifying and/or correcting for the sources of well-to-well or batch-to-batch variability. For example, in certain such embodiments where the CLA reagents are assembled on BMPs (ie CLAMP) for a panel of targets to be used in multiplexed immunoassay, additional BMPs with a modified molecular structure (referred to herein as "normalization BMPs") can be fabricated and used in the same assays for the purpose of monitoring the inter-assay variability, normalizing the read-out data and applying correction factors for matrix effects. The normalization BMPs can be used for, but not limited to measuring and normalizing for: (1) assay signal deterioration due to photobleaching, (2) background increase and/or noise associated with the interference of constituents of the sample, whereby hindering the release the released detection reagent (leading to false-positive signals), (3) maximum signal achievable of the CLAMPs with certain density of the capture strands, (4) target-dependent background increase and/or noise associated with the interference of constituents of the sample.

In some embodiments, where the signal strength after the displacement is subject to deterioration (e.g photobleaching), it is important to account for the deterioration of the signal when comparing the signal of CLAMP assays measured at different time points. A normalization BMP can be used to measure and normalize the read-out date, to account for such losses in signal. For this purpose, a normalization BMP can be constructed with a modified CO that is complementary to the DO. In an assay, the DO will hybridize onto the modified CO and will remain on the surface of the normalization BMP, and will be subject to the same level of signal deterioration as the of the DOs involved in the displacement reaction on other BMPs in a CLAMP assay.

In some embodiments whereby CLAMP reagents are assembled on BMPs to be used for measuring a panel of targets in a complex biological samples (e.g. serum, plasma, etc.), a set of normalization BMPs can be fabricated and used in the assays, to normalize the read-out data to account for the background noise imposed by the interference of the constituents of the samples. Two sets of Normalization BMPs for this purpose can be designed, (1) by assembling CLAMP reagents whereby the capture AB is specific to a species that is different from that of the sample, with a hook strand that is not conjugated to any detection AB. (2) by assembling CLAMP reagents whereby the capture AB is specific to a species that is different from that of the sample, with a hook strand that is conjugated to yet another antibody that is specific to a species that is different from that of the sample. In such a design, after the displacement reaction, one would not expect any signal from specific binding events on normalization BMP. However, if significant signal is recorded, it will be the result of the constituents of the samples, interfering with the release of the displaced HO and labeled displacement reagent, resulting in elevated background signal levels. The signal from the normalization beads can be used to normalize the signal from the CLAMP assay BMPs and correct for such an event.

In some embodiments, whereby multiplexed immunoassays with CLAMP reagents assembled on BMPs, a set of normalization BMPs can be fabricated to measure and correct for target dependent background noise elevations. It has been observed CLAMP BMPs for specifically designed for different, may exhibit varying background noise levels. To measure the target dependent noise levels and normalize the signal at a BMP level, normalization BMPs can be designed with mismatched AB pairs.

In some embodiments whereby, CLAMP reagents are assembled on BMPs to be used in multiplexed immunoassays, a set of normalization BMPs can be fabricated without the presence of antibodies in the structure, and used in the assay to measure the maximum achievable target-independent signal of each assay. The normalization BMP also provides a measurement of the efficacy of the displacement reaction of each assay, and can be used as both a control and a means to normalize the data from each assay. In one embodiment, such normalization BMPs can be designed such that one end of the HO is hybridized onto the CO on the surface, with the other end hybridized on an additional modified CO pre-assembled onto the surface. As such, after the displacement reaction, the HO will be released by the DO on one end, yet remains tethered to the surface via the modified CO. This structure simulates a sandwich antibody-antigen complex on regular CLAMP BMPs.

In some embodiments where CLAMP reagents are assembled on BMPs to be used in multiplexed immunoassays, a set of normalization BMPs can be fabricated measure and normalize for the inter-assay variability (or well-to-well variability). In such embodiment, the normalization BMPs are modified specifically capture a molecular binder that is not present in the sample, such as a specific sequence of an oligo that simulates the binding of antigen in the sample. By adding a known concentration of this oligo (referred to herein as the "antigen-oligo"), to every well containing the CLAMP assay, the signal obtained from that normalization bead is expected to be the same in every well. In the case of well-to-well variability, the signal from all the CLAMP BMPs can be normalized with the from the normalization BMP.

In addition to normalizing for inter-assay variability, modified embodiments of the CLAMP structure can be designed to serve as an "internal control" added within every assay or every well. In certain such embodiments, where the CLAMPs reagents are assembled on BMPs, a positive control BMP can be constructed with antibody pairs that are specific to a species that is not of interest in the CLAMP assay. A positive signal from this BMP, in a sample spiked with its respective recombinant protein, indicates that the CLAMP assay in its entirety and irrespective of the target and species.

In some embodiments, there is provided a detection AB linked to a hook strand and attached to a microparticle indirectly via a releasable link to an anchor strand attached thereto. The hook strand is partially complementary to the anchor strand attached to the microparticle. The anchor strand may be attached to the microparticle via for example a streptavidin/biotin interaction or a chemical bond. The detection AB is thus attached to the microparticle. In this embodiment there is further provided a capture AB which is attached to the microparticle surface, and wherein the detection AB recognizes the same antigen as the capture AB and both ABs can bind the antigen simultaneously. In addition, there is provided a displacement oligonucleotide (the displacer agent) that has a sequence that is complementary to the hook strand, overlapping with the sequence of the anchor strand, so that the detection AB is released from the anchor strand and thus released from the microparticle, if no antigen is bound (i.e., if there is no tertiary complex between capture AB-antigen-detection AB). In a further embodiment, there is also provided a fluorescently-labeled secondary antibody that binds to the detection AB remaining on the microparticle after the displacement reaction.

Figure 15:
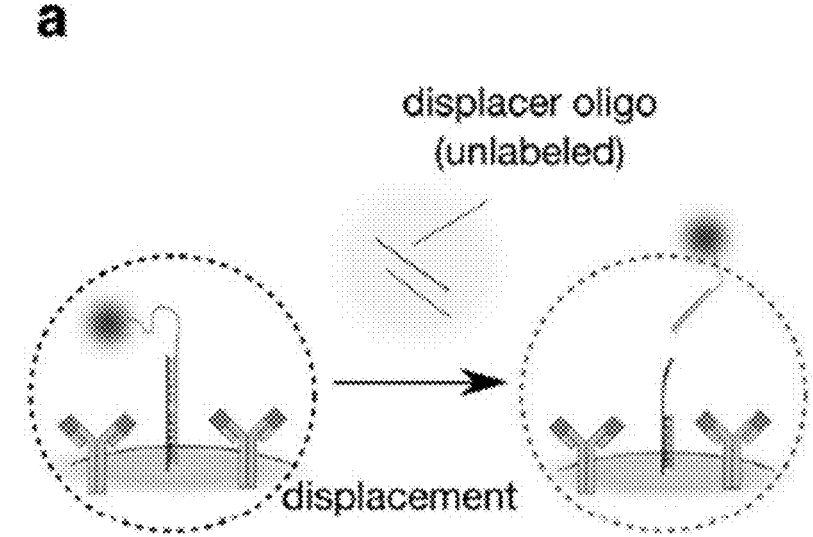
FIG. 15. shows optimization of toe-hold mediated displacement efficiency. (a) Illustration of the displacement reaction, wherein Cy5-labeled HOs are displaced using unlabeled DOs. (b) Release efficiency with respect to increasing NaCl concentration (x-axis) for varying CO starting amounts (blue and red for $n_{CO}$=10 pmols, $n_{CO}$=100 pmols, respectively). No SOs were used in this experiment (i.e. $n_{SO}$=0 pmols). The release efficiency was calculated as $(I_0-I_f)/(I_0-I_B)$ where $I_0$, $I_f$ and $I_B$ are the fluorescence before release, after release, and of the background, respectively. The release efficiency was significantly improved at increased ionic strengths. Increased density of COs led to increased release efficiency, which may be ascribed to reduced fraction of non-specifically bound oligos. (c) Release efficiency with respect to CO density at high salt concentrations (500 mM of NaCl).
Figure 15:
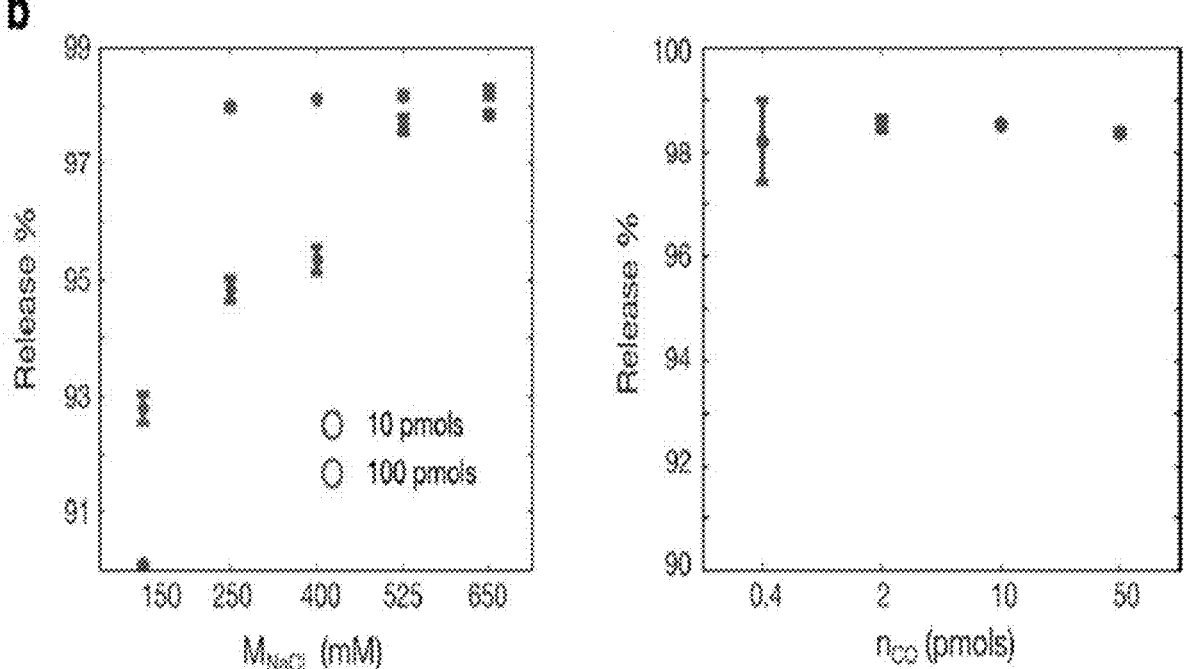
Figure 24:
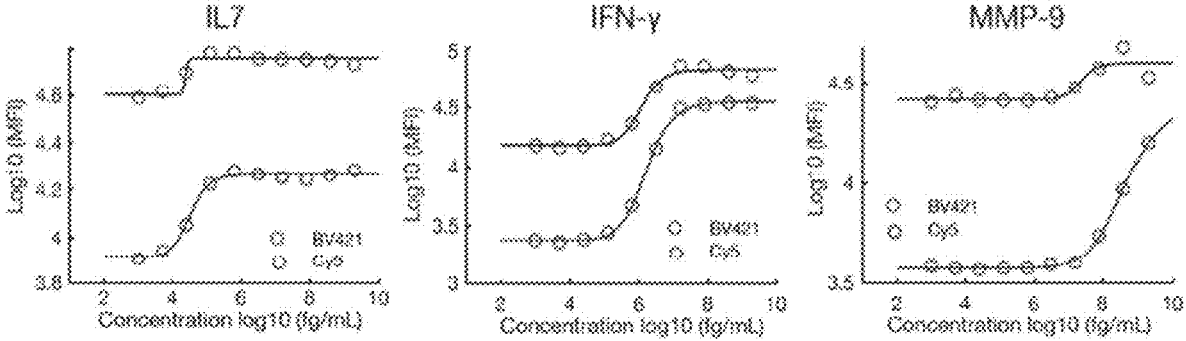
FIG. 24 shows calibration curves obtained using two labelling methods: direct detection of dAbs using BV421-labelled secondary antibody, and displacement-dependent detection using a Cy5-labelled displacer oligo. Calibration curves for IL-7, FN-gamma, and MMP-9 were performed in buffer (PBST) by spiking protein standards in decreased concentrations, and running the assay as described.

It should be noted that, in embodiments where capture and detection ABs are pre-assembled on a support, and detection ABs are labeled with a detectable label, any non-released hook strand-detection AB complexes will result in an analyte-independent signal, which could contribute to the background noise (as shown in FIG. 24). Hence, it will be appreciated that to avoid increasing the background signal, a near-complete anchor strand-hook strand displacement reaction and washing of hook strand-detection AB complexes are necessitated. It will also be appreciated that such near-complete release can be difficult even with optimized conditions (FIG. 15). To reduce such increased background signal resulting from inefficient release of the anchor strand-hook strand link, in some embodiments, the hook strand, anchor strand, or detection ABs are labeled with a label that remains inactive/undetectable until displacement or release of the hook strand from the anchor strand. In another embodiment, the hook strand, anchor strand, or detection ABs are not labeled, and the displacer agent is labeled with a detectable label. In such embodiments, signal transduction at the support only occurs if both of the following conditions are satisfied: (i) formation of a tertiary captureAB-analyte-detectionAB complex, and (ii) displacement of the hook strand-anchor strand hybrid. In these embodiments, a non-displaced hook strand will not contribute to the signal. It should be appreciated that, similarly, embodiments where the label on the detection AB and/or the hook strand is inactive or undetectable until after the release can be advantageous since a non-released (e.g., non-displaced) hook strand (or detection AB) will not contribute to the signal.

Figure 23:
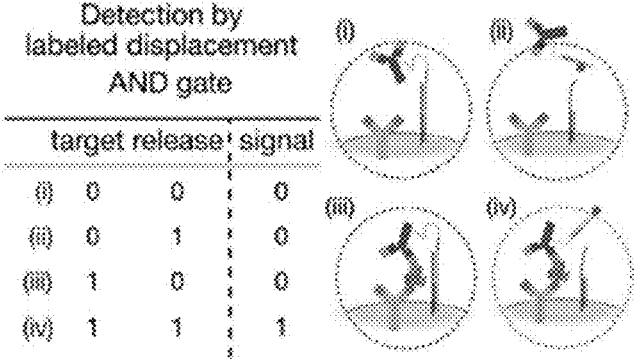
FIG. 23 shows an AND (Boolean) logic gate representation of the detection by labeled-displacement step, where detection at the single-molecule level requires both the capture of target and successful hook strand oligonucleotide (HO) release.

In one embodiment, a labeled displacer agent (e.g., oligonucleotide) can perform the dual-function of release (displacement) and labeling. In this way, through only labeling the displaced hook strands, a detectable signal/signal transduction necessitates two conditions, akin to an "AND" logical gate (FIG. 23). One potential advantage of such embodiments is that they do not require a change in the design of DNA sequences or linkage properties of the detection complex including hook and anchor strands.

In some embodiments, an additional level of redundancy can be achieved by using a hook strand with an inactive or undetectable label which is only activated or detectable upon displacement from the anchor strand. For example, in one embodiment a hook strand is labeled with a dye that is quenched by a dye quencher that can be conjugated to the anchor strand. In another embodiment, displacement can be similarly achieved using a restriction enzyme, followed by signal generation using a labeled-oligo that targets the previously-hybridized (and hence unavailable for binding) portion of the hook strand, thereby only hybridizing to and labeling already displaced hook strands.

In certain embodiments, there is provided a detection AB linked to a microparticle via a hook strand, the hook strand being an oligo, which is linked to the detection AB. The hook strand oligo is partially complementary to an anchor strand, which is also an oligo, linked to the microparticle via e.g., a streptavidin/biotin interaction or a chemical bond, thus attaching the detection AB to the microparticle. There is further provided a capture AB which is linked to the microparticle surface and wherein the detection AB recognizes the same antigen as the capture AB and both ABs can bind the antigen simultaneously. In addition, there may be provided a displacement agent which is an oligonucleotide containing a fluorescent label or a DNA barcode sequence and has a sequence complementary to the hook strand oligonucleotide, overlapping with the sequence of the anchor strand oligonucleotide so that the detection Ab is released from the anchor strand oligo and thus may be released from the microparticle.

It should be understood that, in methods and systems provided herein, the use of colocalization and linkages may necessitate rational topological design to optimize the availability of both ABs (capture AB and detection AB) across a support. In some embodiments, with stochastically distributed capture ABs and/or detection ABs attached to the support, appropriate binding of an analyte may require optimization of two important design parameters: (i) the relative density of the capture and detection ABs, and (ii) the length of the hook strand. These two parameters serve to control the time-averaged distance between capture and detection ABs by considering the gyration radius of the detection AB. In some cases, the distance between capture and detection ABs, and ultimately the effective-affinity at the single-molecule level, may be stochastic and difficult to control. Therefore, in some embodiments it may be desirable to optimize the aforementioned two parameters for optimal assay performance.

Figure 5:
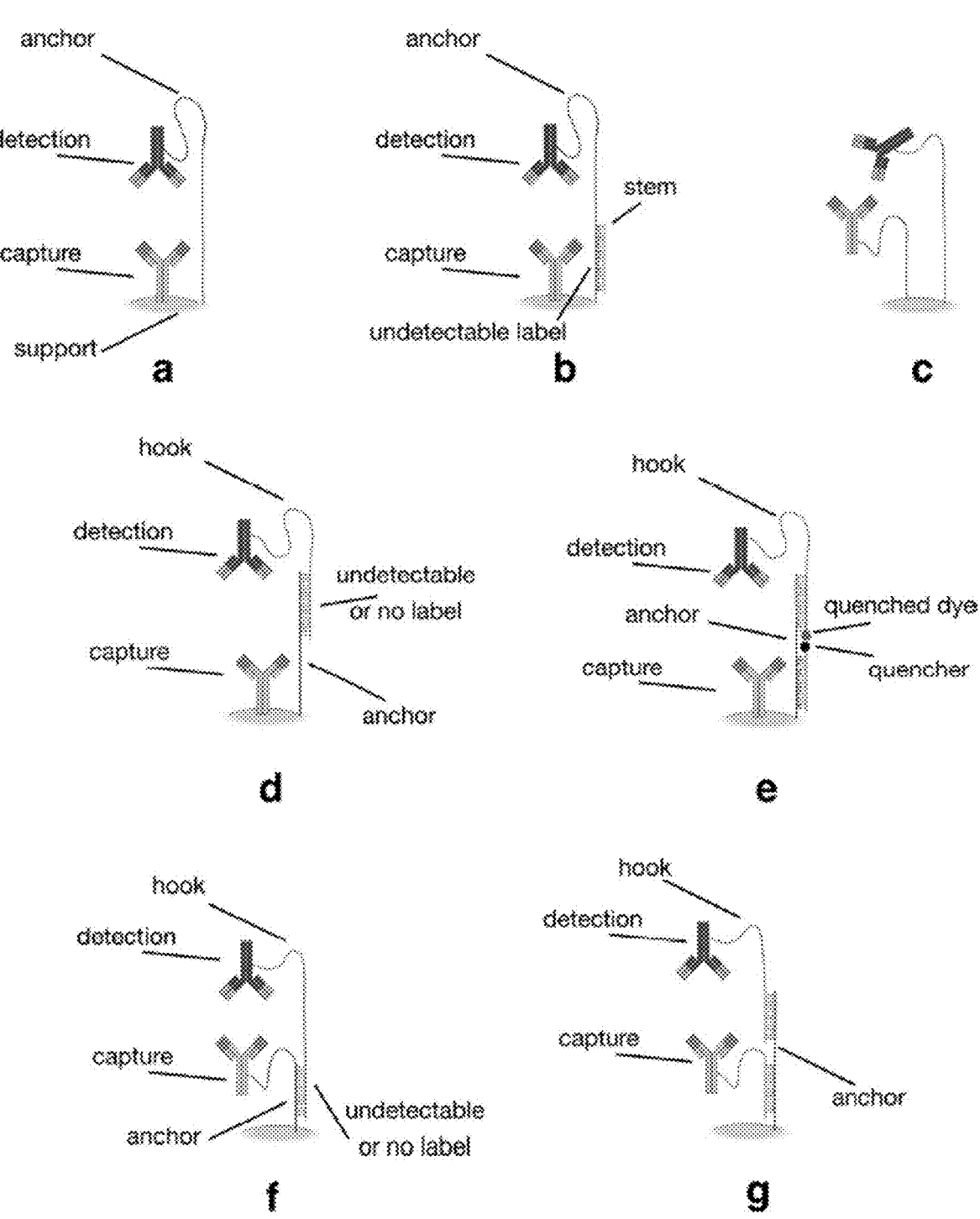
FIG. 5 shows a schematic diagram illustrating exemplary embodiments of CLA complexes prior to contact with a biological sample and displacement, wherein the label is either absent or inactive/undetectable. (a) Detection AB is linked to the support using the anchor strand (i.e., direct linkage to the anchor strand). (b) A stem oligo hybridizes to the anchor strand, which is labeled, and serves to mask the label (e.g., a specific DNA sequence) so that it is undetectable before release. (c) Both capture and detection antibodies are flexibly linked to the support. (d) Detection AB is linked to a hook strand, the hook strand being releasably attached to the anchor strand, optionally including an undetectable label (the label may be attached to the hook strand or to the anchor strand). (e) Detection AB is linked to a hook strand, the hook strand being releasably attached to the anchor strand, and the hook strand is conjugated to a dye that is quenched (before release) by a proximal quencher on a stem oligo that is also bound to the anchor strand. (f) Both capture and detection antibodies are linked to the anchor strand, the capture AB being linked directly to the anchor strand, and the detection AB being attached indirectly via a hook strand oligo that is optionally attached to an undetectable label (i.e., label is undetectable when hook strand is attached to the anchor strand, and becomes detectable after release). (g) Both capture and detection antibodies are linked indirectly to the anchor strand via their respective capture and hook strands.
Figure 21:
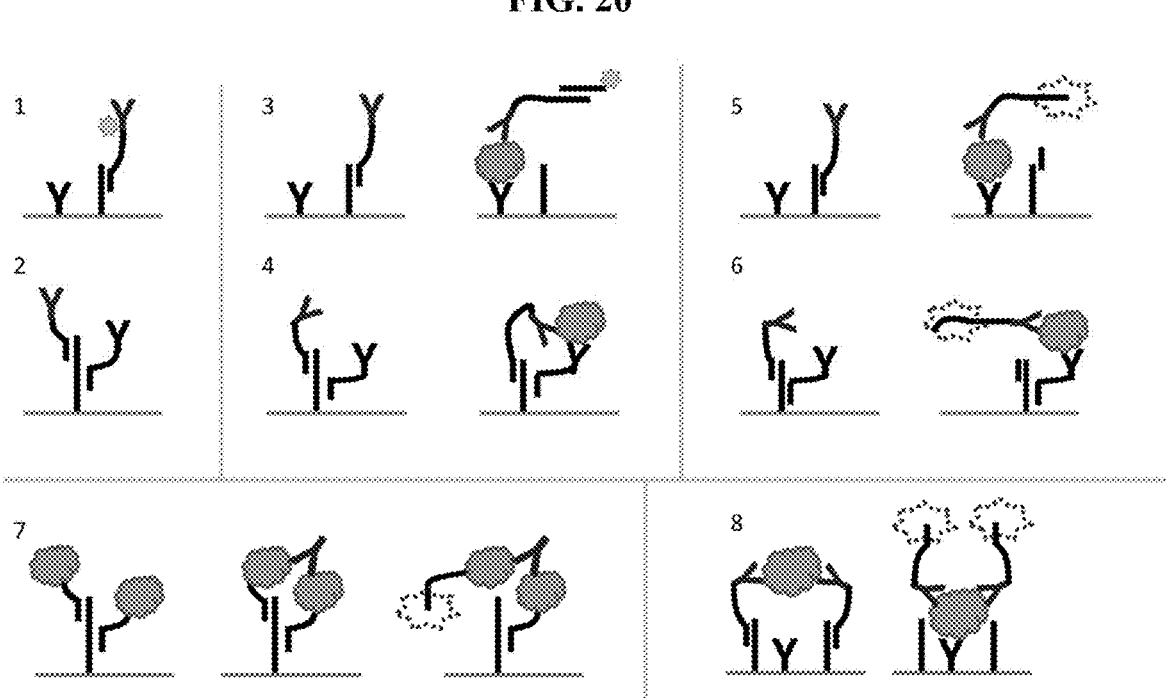
FIG. 21 shows a schematic illustration of several embodiments. (1) shows a CLAMP embodiment where the capture and detection reagents are antibodies and the detection reagent is linked to the anchor strand by a DNA hybrid, and the detection antibody is labelled; (2) shows an embodiment where both capture and detection antibodies are attached to the anchor strand via an oligo linker and a DNA hybrid, and the detection antibody is labelled. (3) shows an embodiment where shows a CLAMP embodiment where the capture and detection reagents are antibodies and the detection reagent is linked to the anchor strand by a DNA hybrid, and there is no label on the detection reagent or the hook strand. A tertiary complex forms in the presence of analyte, and the hook strand is displaced from the anchor strand by a labeled displacer oligo. (4) shows an embodiment where both capture and detection antibodies are attached to the anchor strand via an oligo linker and a DNA hybrid and there is no label on the detection reagent or the hook strand. A tertiary complex forms in the presence of analyte, and the hook strand is displaced from the anchor strand by a labeled displacer oligo. (5) shows the embodiment of (1) but where the label is attached to the hook strand and is masked by the DNA hybrid attaching the hook strand to the anchor strand. A tertiary complex forms in the presence of analyte, and the hook strand is displaced from the anchor strand by a displacer oligo that binds or hybridizes to the anchor strand. The label on the hook strand is activated or unmasked after the displacement reaction. (6) shows the embodiment of (4) but where, as in (5), the label is attached to the hook strand and is masked by the DNA hybrid attaching the hook strand to the anchor strand. A tertiary complex forms in the presence of analyte, and the hook strand is displaced from the anchor strand by a displacer oligo that binds or hybridizes to the anchor strand. The label on the hook strand is activated or unmasked after the displacement reaction. (7) shows an embodiment where the capture and detection reagents are both antigens and are both linked to the anchor strand via an oligo linker that hybridizes to the anchor strand. A complex is formed in the presence of an antibody (the analyte in this embodiment) that binds both antigens. The label is attached to the hook strand and is masked by the DNA hybrid attaching the hook strand to the anchor strand. The label on the hook strand is activated or unmasked after cleavage from the anchor strand. (8) shows an embodiment where the capture reagent is an antibody attached directly to the support and there are two anchor strands. Each of the two anchor strands is linked by a DNA hybrid to a detection antibody. In the presence of analyte a quaternary complex is formed. Each of the two hook strands is labeled, and the hook strand labels are unmasked by release of the link to their respective anchor strands. The two labels may be the same or different.

In another embodiment, the capture AB and the detection AB are both linked to the anchor strand, allowing concomitant control over capture and detection AB densities whilst maintaining colocalization at the nano-scale, potentially allowing more accurate control of assay performance (such as shown in FIGS. 5F-G, and some embodiments in FIG. 21). In such embodiments, the capture and detection ABs are colocalized and their relative density is the same, and can be modulated at the same time. One potential advantage of this embodiment is a homogeneous average-distance between capture and detection ABs for all pairs on a support. A second potential advantage of this embodiment is that the architecture of the capture and detection ABs may be precisely controlled. For example, by decreasing the length of the single-stranded portion of the anchor strand or the hook strand, the stringency of binding may be controlled, providing a deterministic means to control thermodynamics of the assay system. It will be appreciated by those skilled in the art that increasing the stringency of binding can lead to a decrease in effective affinity. In some embodiments, such tuning of the effective affinity can be used, among other applications, to control and extend the dynamic range of the assay.

In some such embodiments where the effective affinity can be tuned by changing the length of the hook strand or the anchor strand (i.e., the linker length), or by tuning the surface densities of capture and detection ABs, multiplexed arrays (such as multiplexed microparticles) can be fabricated that are designed with different effective affinities. This can be useful to extend the dynamic range of a particular assay for a particular analyte. For example, those skilled in the art will appreciate that some proteins are present in blood in concentrations ranging >5 orders of magnitude; for such targets, several assays can be designed, with different barcodes, to be able to quantify such proteins over a larger dynamic range.

In an embodiment, a capture AB is conjugated to a capture oligonucleotide which hybridizes to one sequence domain of the support-linked anchor strand. Another sequence domain of the anchor strand may be hybridized to the hook strand which is linked to the detection AB. All the aforementioned strategies for signal transduction and generation can also be utilized in this embodiment.

In an embodiment, two or more sets of distinguishable (i.e., multiplexed) complexes detecting the same target can be designed to increase the dynamic range of a multiplexed assay, wherein the lengths of the hook strand oligos for the two or more sets, and hence the stringency of the binding, can be controlled. For example, two or more sets of microparticles with different barcodes but targeting the same analyte can be fabricated, wherein the first microparticle set includes a shorter hook strand oligo to reduce flexibility and increase stringency of binding, and wherein the second microparticle set includes a longer hook strand oligo to increase flexibility and reduce stringency of binding, and so on. In this way, the first microparticle set can be designed to quantitate the analyte when it is present at higher concentrations.

The CLA methods, compositions, and systems presented here can be used to extend the dynamic range of one or more assays within a multiplexed pool. Using two or more sets of distinguishable CLAMPs (i.e., multiplexed) designed to quantify the same analyte but target at different concentrations, as described previously. In this way, the first CLAMP set can be designed to quantitate the analyte when it is present at higher concentrations, whereas the second CLAMP set can be designed to quantitate the analyte when it is at lower concentrations, and so on. Combining together the data from two or more CLAMP sensors with distinguishable barcodes enables a wider range detection of the analyte of interest; however, since every target now requires multiple distinguishable barcodes, this approach requires at least double the number of barcodes, which at least doubles the requirements on the number of barcodes needed.

In another embodiment, the CLA methods and systems presented here can be used to extend the dynamic range of an assay without necessitating additional barcodes. In some such embodiments, two or more CLAMP sets are designed to quantify an analyte at different concentrations, but wherein the CLAMP sets possess the same barcode. For example, two target-specific CLAMPs with the same barcodes (i.e. they have the same fluorescent spectra ahead of the assay) that have been designed to capture higher and lower concentration of the target, respectively, can still be used to extend the quantifiable concentration range of the analyte of interest via the detection signal. The combined signal of the two or more sensors will provide, at the very least, a one-to-one correlation with the concentration of the analyte of interest. The combined signal could also treated as a detection signature that directly related to the concentration of the analyte of interest.

It is therefore provided a method to extend the dynamic range of a CLAMP assay, comprising: (1) providing one or more sets of CLAMP constructs, wherein each CLAMP set is designed to detect or quantify the same analyte at different concentrations ranges, and wherein all said CLAMP sets are indistinguishable from each other based on their fluorescent spectra, (2) performing the assay, (3) determining the concentration the protein by analyzing the combined spectra of all said CLAMP sets.

The CLA methods and systems presented here can be used to extend the dynamic range of one or more assays within a multiplexed pool. In some other embodiments, the sample can be divided into two or more dilutions, wherein each of the dilutions can be separately contacted and incubated with the same multiplexed pool of CLAMPs. After washing, the multiplexed pool can be re-combined together and the detection and read-out steps completed as described in this invention. The ability to quantify the concentration based on the detection channel or read-out of every barcode, as described herein, allows extension of the dynamic range.

Accordingly, provided are compositions for extending a dynamic range of a colocalization by linkage assay, comprising first co-localization by linkage assay (CLA) complex and a second CLA complex, wherein the first CLA complex and the second CLA complex are configured to have an overlapping fluorescent spectra, and wherein the first CLA complex is configured to capture a first concentration of analyte and the second CLA complex is configured to capture a second concentration of analyte, wherein the first concentration of analyte and the second concentration of analyte are different.

In some embodiments, the first concentration of analyte is greater than the second concentration of analyte.

In some embodiments, the first concentration of analyte is about 0.25, 0.5, 1.0, 1.5, 2.0, 5.0, 10, or 20 fold greater than the second concentration of analyte. In some embodiments, the first concentration is about 0.25, 0.5, 1.0, 1.5, 2.0, 5.0, 10, or 20 fold greater than the second concentration. In some embodiments, the first concentration is greater by about 0.1 fold to about 50 fold. In some embodiments, the first concentration is greater by about 0.1 fold to about 0.25 fold, about 0.1 fold to about 0.5 fold, about 0.1 fold to about 2 fold, about 0.1 fold to about 5 fold, about 0.1 fold to about 10 fold, about 0.1 fold to about 15 fold, about 0.1 fold to about 20 fold, about 0.1 fold to about 50 fold, about 0.25 fold to about 0.5 fold, about 0.25 fold to about 2 fold, about 0.25 fold to about 5 fold, about 0.25 fold to about 10 fold, about 0.25 fold to about 15 fold, about 0.25 fold to about 20 fold, about 0.25 fold to about 50 fold, about 0.5 fold to about 2 fold, about 0.5 fold to about 5 fold, about 0.5 fold to about 10 fold, about 0.5 fold to about 15 fold, about 0.5 fold to about 20 fold, about 0.5 fold to about 50 fold, about 2 fold to about 5 fold, about 2 fold to about 10 fold, about 2 fold to about 15 fold, about 2 fold to about 20 fold, about 2 fold to about 50 fold, about 5 fold to about 10 fold, about 5 fold to about 15 fold, about 5 fold to about 20 fold, about 5 fold to about 50 fold, about 10 fold to about 15 fold, about 10 fold to about 20 fold, about 10 fold to about 50 fold, about 15 fold to about 20 fold, about 15 fold to about 50 fold, or about 20 fold to about 50 fold. In some embodiments, the first concentration is greater by about 0.1 fold, about 0.25 fold, about 0.5 fold, about 2 fold, about 5 fold, about 10 fold, about 15 fold, about 20 fold, or about 50 fold. In some embodiments, the first concentration is greater by at least about 0.1 fold, about 0.25 fold, about 0.5 fold, about 2 fold, about 5 fold, about 10 fold, about 15 fold, or about 20 fold. In some embodiments, the first concentration is greater by at most about 0.25 fold, about 0.5 fold, about 2 fold, about 5 fold, about 10 fold, about 15 fold, about 20 fold, or about 50 fold.

In some embodiments, the first analyte is different from the second analyte.

In some embodiments, the first CLA complex and second CLA complex use a different capture agent, detection agent, or detection and capture agent. In some embodiments, the the composition provides a first detection signal for the first CLA complex and a second detection signal for the second CLA complex, thereby extending the dynamic range of detection for the first CLA complex and the second CLA complex configured to have the overlapping fluorescent spectra.

In some embodiments, the overlapping florescent spectra are greater than 50%, 60%, 70%, 80%, or 90% overlapping. In some embodiments, the overlapping florescent spectra are greater than 50%, 60%, 70%, 80%, or 90% overlapping. In some embodiments, the overlapping florescent spectra are 100% overlapping. In some embodiments, the florescent spectra peaks or profiles overlap by about 10% to about 100%. In some embodiments, the florescent spectra peaks or profiles overlap by about 10% to about 25%, about 10% to about 50%, about 10% to about 60%, about 10% to about 70%, about 10% to about 80%, about 10% to about 90%, about 10% to about 100%, about 25% to about 50%, about 25% to about 60%, about 25% to about 70%, about 25% to about 80%, about 25% to about 90%, about 25% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, or about 90% to about 100%. In some embodiments, the florescent spectra peaks or profiles overlap by about 10%, about 25%, about 50%, about 60%, about 70%, about 80%, about 90%, or about 100%. In some embodiments, the florescent spectra peaks or profiles overlap by at least about 10%, about 25%, about 50%, about 60%, about 70%, about 80%, or about 90%. In some embodiments, the florescent spectra peaks or profiles overlap by at most about 25%, about 50%, about 60%, about 70%, about 80%, about 90%, or about 100%.

In some embodiments, the wherein the overlapping florescent spectra are 100% overlapping.

Further provided are compositions for extending a dynamic range of a colocalization by linkage assay, comprising first co-localization by linkage assay (CLA) complex and a second CLA complex, wherein the first CLA complex and the second CLA complex are configured to have an overlapping fluorescent spectra, and wherein the first CLA complex is present a first concentration and the second CLA complex is present at second concentration, wherein the first concentration and the second concentration are different.

In some embodiments, the first concentration is greater than the second concentration. In some embodiments, the first concentration is about 0.25, 0.5, 1.0, 1.5, 2.0, 5.0, 10, or 20 fold greater than the second concentration. In some embodiments, the first concentration is greater by about 0.1 fold to about 50 fold. In some embodiments, the first concentration is greater by about 0.1 fold to about 0.25 fold, about 0.1 fold to about 0.5 fold, about 0.1 fold to about 2 fold, about 0.1 fold to about 5 fold, about 0.1 fold to about 10 fold, about 0.1 fold to about 15 fold, about 0.1 fold to about 20 fold, about 0.1 fold to about 50 fold, about 0.25 fold to about 0.5 fold, about 0.25 fold to about 2 fold, about 0.25 fold to about 5 fold, about 0.25 fold to about 10 fold, about 0.25 fold to about 15 fold, about 0.25 fold to about 20 fold, about 0.25 fold to about 50 fold, about 0.5 fold to about 2 fold, about 0.5 fold to about 5 fold, about 0.5 fold to about 10 fold, about 0.5 fold to about 15 fold, about 0.5 fold to about 20 fold, about 0.5 fold to about 50 fold, about 2 fold to about 5 fold, about 2 fold to about 10 fold, about 2 fold to about 15 fold, about 2 fold to about 20 fold, about 2 fold to about 50 fold, about 5 fold to about 10 fold, about 5 fold to about 15 fold, about 5 fold to about 20 fold, about 5 fold to about 50 fold, about 10 fold to about 15 fold, about 10 fold to about 20 fold, about 10 fold to about 50 fold, about 15 fold to about 20 fold, about 15 fold to about 50 fold, or about 20 fold to about 50 fold. In some embodiments, the first concentration is greater by about 0.1 fold, about 0.25 fold, about 0.5 fold, about 2 fold, about 5 fold, about 10 fold, about 15 fold, about 20 fold, or about 50 fold. In some embodiments, the first concentration is greater by at least about 0.1 fold, about 0.25 fold, about 0.5 fold, about 2 fold, about 5 fold, about 10 fold, about 15 fold, or about 20 fold. In some embodiments, the first concentration is greater by at most about 0.25 fold, about 0.5 fold, about 2 fold, about 5 fold, about 10 fold, about 15 fold, about 20 fold, or about 50 fold.

In some embodiments, the first CLA complex and the second complex capture a different analyte. In some embodiments, the first CLA complex and second CLA complex comprise a different capture agent, detection agent, or detection and capture agent. In some embodiments, the composition provides a first detection signal for the first CLA complex and a second detection signal for the second CLA complex, thereby extending the dynamic range of detection for the first CLA complex and the second CLA complex configured to have the overlapping fluorescent spectra. In some embodiments, the overlapping florescent spectra are greater than 50%, 60%, 70%, 80%, or 90% overlapping. In some embodiments, the overlapping florescent spectra are 100% overlapping. In some embodiments, the florescent spectra peaks or profiles overlap by about 10% to about 100%. In some embodiments, the florescent spectra peaks or profiles overlap by about 10% to about 25%, about 10% to about 50%, about 10% to about 60%, about 10% to about 70%, about 10% to about 80%, about 10% to about 90%, about 10% to about 100%, about 25% to about 50%, about 25% to about 60%, about 25% to about 70%, about 25% to about 80%, about 25% to about 90%, about 25% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, or about 90% to about 100%. In some embodiments, the florescent spectra peaks or profiles overlap by about 10%, about 25%, about 50%, about 60%, about 70%, about 80%, about 90%, or about 100%. In some embodiments, the florescent spectra peaks or profiles overlap by at least about 10%, about 25%, about 50%, about 60%, about 70%, about 80%, or about 90%. In some embodiments, the florescent spectra peaks or profiles overlap by at most about 25%, about 50%, about 60%, about 70%, about 80%, about 90%, or about 100%.

Accordingly, also provided are method of analyzing a sample comprising a first and a second analyte, comprising: (a) contacting the sample with a the dynamic range extending composition (e.g. configured to bind different concentrations of analytes or CLA compositions at different compositions); (b) providing detectable displacer agent comprising a fluorescent polymer, configured to couple with the detection agent and release the detection agent from the second anchor element; and (c) detecting the detectable displacer element to determine a first signal identifying the first CLA complex, and a second signal identifying the second CLA complex.

In another embodiment, the flexibility of the hook strand oligo can be controlled by hybridizing short oligos to the single-stranded region, creating sections of rigid double-stranded DNA. The term "flexibility", as an example, can herein be used to define the degree of conformation freedom of a molecule or it can be used to referred to a relative total number of conformations a molecule can adopt. This has the effect of reducing the number of conformations of the hook strand oligo that permit dual binding, thus altering the stringency of binding and decreasing the effective affinity. The stiffening oligos hybridized to the hook strand oligo could be small, on the order of 10 nucleotides, to only slightly increase the stringency of binding. The stiffening oligos could otherwise be long, on the order of 40 nucleotides, or 60 nucleotides, or equal in length to the entirety of the single-stranded region of the hook strand oligo, substantially reducing the conformations permitting dual binding.

In yet another embodiment, the single-stranded region of the hook strand oligo can be designed such that it forms a semi-stable stem-loop. For example, two or more sets of microparticles with different barcodes but targeting the same analyte may be fabricated, wherein the first microparticle set has an unmodified hook strand oligo sequence; and wherein the second microparticle set includes a hook strand oligo that transiently folds and unfolds, wherein the detection AB is unable to bind while the hook strand oligo is in its folded state, changing the effective affinity of the CLAMP for its target. The stability of the stem-loop structure can be modified by altering the number of complementary bases that form the stem, allowing the dynamic range to be tuned.

Alternatively, the hook strand looping oligo may form a transient dimer structure with another short oligo. In such an embodiment, the short oligo might be partially complementary to the hook strand oligo in multiple, non-adjacent places, such that when bound it would create a loop in the hook strand oligo and reduce its effective length. Each region of the short oligo complementary to a part of the hook strand oligo might consist of about 20 nucleotides, or more preferably about 10 nucleotides, such that it would have a melting temperature close to the assay temperature. The short oligo would be added to the sample prior to incubation with the complexes; it could optionally also be incubated with the complexes prior to introduction of the sample. The short oligo would form a dimer with the hook strand oligo, wherein the detection AB is unable to form a ternary complex with an analyte and capture AB while the hook strand oligo is in its looped state, changing the effective affinity of the CLAMP for its target. The stability of the dimer can be modified by altering the number of complementary bases between the short oligo and the hook strand oligo, allowing the dynamic range to be tuned.

In an embodiment, an additional strand may be added to the complex that is very long and flexible such that it increases steric hindrance at the surface, and around the detection antibody. This strand could tangle the detection AB such that it is less likely to bind a target, or it could decrease the ability of a target molecule to approach the surface. In either case, the effective affinity of the complex for a target is reduced.

In an embodiment, the detection AB or the capture AB may be modified to reduce its affinity for the target. For instance, if the AB is an aptamer then a single nucleotide change in a key target-recognition region will decrease its ability to bind a target. Modification of the true binding affinity of one of the ABs would change in the overall binding affinity of the complex, leading to a shift in the dynamic range. In certain embodiments, modification of the inherent affinity of detection or capture AB can occur during conjugation steps. For instance, the inclusion of small molecule crosslinkers such as NHS esters linked to different PEG sizes during conjugation with oligonucleotides can result in small-molecule binding at the paratope of the antibody, decreasing its affinity to its target with increasing amount of NHS esters.

In an embodiment, elements that compete with the target to bind ABs may be introduced. The ABs may have a similar affinity to these elements as compared to their targets, or the affinity may be higher or lower. The competitive elements must not have more than one binding site recognized by the ABs, in order to prevent dual binding and the generation of false-positives. For example, if the ABs are aptamers then an oligonucleotide complementary to the target-recognition region could be added as a competitive element, wherein the complementary oligo would transiently block the analyte from being bound by the aptamer. Alternatively, if the ABs are antibodies then copies of the peptide fragments used to produce them could be added to the sample to the same effect. This would reduce the effective concentration of the analyte measured, and thus permit quantification of the analyte at higher true concentrations.

In an embodiment, local ionic strength on CLAMP can be modified to modify the effective affinity of the AB pair. This may be achieved using means such as, elements with higher charge that result in increased local ionic strength due to double layer effect. Conversely, the local electrostatic field can be decreased through the addition of surface molecules with equal and opposite charge so as to have a neutralizing effect.

Those skilled in the art will recognize that another challenge of multiplexed assays is interference and matrix effects, which can be difficult to control at the analyte-level. One of the advantages of methods and systems provided herein, in some embodiments, is the ability to contact the same biological sample with multitudes of assay configurations within the same assay volume. This flexibility may provide the ability to individually control for matrix effects on specific ABs and assay reagents. For example, certain samples could contain endogenous antibodies and other molecules which could positively or negatively impact the intensity of the assay signal for specific analytes.

In another embodiment, there are provided distinct supports or biomolecule complexes, with every analyte-specific support lacking either one of the capture or detection ABs and acting as an analyte-specific internal standard that controls for matrix effects and other potential modes of failures of the assay. The assay signal of the fully-formed biomolecule complex on the support can then be compared to these single-AB controls. These internal controls can be used as flags for potential false positives.

Figure 13:
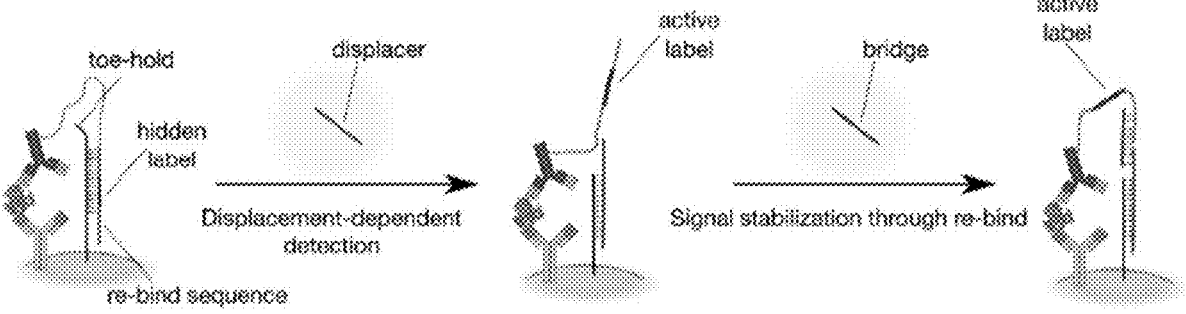
FIG. 13 shows a schematic diagram illustrating an embodiment of CLA used to stabilize signal after displacement, and before detection, using a re-bind mechanism. In this embodiment, the hook strand oligo includes a label sequence, and a re-bind sequence; after displacement with a displacer agent oligo that binds to the anchor strand and optional washing, a bridge strand binds to both the re-bind sequence and the anchor strand, thereby reconnecting the hook strand indirectly to the anchor strand. In this way the hook strand is re-attached to the support, along with the active/detectable label and the detection AB to which it is linked.

Those skilled in the art will recognize that another challenge of assays, particularly when using binders with non-zero or fast off-rate (k-off), is the unbinding of analytes, and hence drop in the assay signal, that can occur in the time between the washing of the biological sample to the read-out of the assay signal. This unbinding is especially problematic for low concentration analytes, and read-out methods that cannot measure the different assays in multiplex (e.g. cytometry). This problem may also be present in the CLA sensor procedure, whereby post-release (e.g., post-displacement), unbinding of the analyte to either the capture AB or the detection AB may result in signal loss. In yet another embodiment, therefore, the CLA methods and systems provided herein can be modified to mitigate this problem of unbinding and time-dependent signal by transducing the assay signal from a reversible reaction (e.g., an AB-analyte) into a stable oligo hybrid to stop further unbinding and is linked to the support enabling storage and read-out at a later time (such as shown in FIG. 13). A potential advantage of this embodiment is minimizing signal loss after assay completion which could help to increase sensitivity. Another potential advantage of this embodiment is the normalization of signal drop across different assays and samples that may be read out over a non-negligible amount of time, enabling better signal reproducibility and improved precision. In some such embodiments, an assay may be conducted similarly to previous embodiments, wherein the assay label is a unique DNA sequence, wherein following washing of released detection AB, a replacement agent can be introduced to re-link the hook strand back onto the anchor strand, thereby conserving the signal on the support. As those skilled in the art can appreciate, another potential advantage for this embodiment is reproducibility of the signal intensity, and, particularly, removing any dependence of the assay signal on time-to-measure and temperature.

In some such embodiments, there is provided a displacer agent which is an oligo that displaces the anchor strand-hook strand hybrid by binding to the anchor strand oligo via a toe-hold displacement reaction, followed by washing of released and unbound hook strand oligo-detection AB complexes, followed by addition of a replacement oligo that enables re-binding of the hook strand oligo to the anchor strand oligo by hybridizing to both oligos.

In some embodiments there is provided a method for the detection and/or quantitation of an analyte in a sample, the method comprising: (a) providing a support, a capture reagent attached to the support, a detection reagent linked to a first linker, wherein the first linker is releasably-attached to a second linker, wherein the second linker is attached to the support, (b) the support with the sample under conditions that allow simultaneous binding of the capture reagent and the detection reagent to the analyte, to form a tertiary complex; and (c) adding a displacer agent, wherein the displacer agent releases the first linker from the second linker by binding preferentially to the second linker, such that the detection reagent and the first linker are released from the support in the absence of the analyte; and (d) adding a bridging agent, wherein the bridging agent binds the first linker on to the support; and (e) optionally determining the presence and/or the amount of the first linker and detection reagent on the support, wherein the presence and/or the amount of the first linker and detection reagent on the support indicates the presence and quantity of the analyte in the sample.

In some embodiments there is provided a method for the detection and/or quantitation of an analyte in a sample, the method comprising: (a) providing a support, a capture reagent attached to the support, a detection reagent linked to a first linker, wherein the first linker is releasably-attached to a second linker, wherein the second linker is attached to the support, wherein the first linker contains an inactive label (b) the support with the sample under conditions that allow simultaneous binding of the capture reagent and the detection reagent to the analyte, to form a tertiary complex; and (c) adding a displacer agent, wherein the displacer agent releases the first linker from the second linker by binding preferentially to the second linker, such that the detection reagent and the first linker are released from the support in the absence of the analyte, and such that the release of the first linker from the second linker activates the label on the first linker; and (d) adding a bridging agent, wherein the bridging agent binds the first linker on to the support; and (e) optionally determining the presence and/or the amount of the first linker on the support, wherein the presence and/or the amount of the label on the first linker on the support indicates the presence and quantity of the analyte in the sample.

In some embodiments, the first and second linker are DNA oligonucleotides with at least some complementary sequence, and the displacer agent is a DNA oligonucleotide that binds to the first linker through toe-hold mediated strand displacement. In some other embodiments, the inactivated linker is a DNA sequence within the first linker that is hybridized to the second linker.

A mammalian organism's immune system produces antibodies which are also known as immunoglobulins. They serve as a defense in response to the introduction of foreign substances, also known as antigens. The immunoglobulins can be divided into five different classes or isotypes. One distinguishes between immunoglobulins of the M, G, A, E and D isotypes. These five immunoglobulin isotypes differ in the composition of the heavy chain which is referred to as the y, a, c and 6 chain, respectively. Each isotype has a different function in the organism. The class M immunoglobulins occur during a first contact with the antigen, the so-called primary immunization. However, the concentration of these immunoglobulins rapidly decreases as the infection progresses. The class G immunoglobulins are firstly slowly formed during a primary immunization and occur in large amounts in a second infection with the same antigen. The class A immunoglobulins are found on the surfaces of the mucous membranes of the organism and are responsible for the local defense processes. The class E immunoglobulins are mainly responsible for allergic reactions. The exact function of the class D immunoglobulins is thus far unknown.

Different methods for identifying and quantifying antibodies are described in the prior art. The detection of a certain class of antigen-specific antibodies in a sample is often performed by binding specific antibodies to a solid phase coated with the specific antigen. The immunoglobulins (Ig), which are specific for the antigen and are now bound to the solid phase, are detected by the binding of antibodies, which are specifically directed against human Ig of a certain class, to the Ig molecules to be detected. The antibodies directed against human Ig are provided with a label by means of which the detection takes place. However, such a test procedure (indirect test format) is only possible if, before the reaction with the class-specific labelled antibodies directed against human Ig, all unspecific, non-bound Ig is removed by washing. Furthermore, washing is rarely efficient, and in certain cases is especially problematic, resulting in high background signals. It is a disadvantage of this process that falsely positive values are obtained due to nonspecific binding of non-specific antibodies contained in the sample. For example, multiplexed autoantibody assays that are used to detect many specific autoantibodies have been severely hindered by specificity. Autoantibodies are typically captured by specific recombinant or native antigens on a solid-support, and are then detected by a species-specific detection antibody (e.g., anti-human Fc IgG). As a result, any non-specific binding of autoantibodies present in sera will be detected and often leads to a false-positive, making this type of assay a single-binder assay (in other words, limited to single-plex form). A further test for the detection and for the quantitative determination of an antibody consists in that antigens against the antibodies to be determined are fixed on a solid phase. Subsequently, there is added thereto a patient's serum, together with a predetermined amount of the antibody to be determined but which carries a label and subsequently the label bound to the solid phase is measured. It is thus a competitive test, the sensitivity of which leaves something to be desired. A further possibility is to bind an anti-Ig antibody to a solid phase and then to react it with the test solution. Subsequently, there is added an antigen specific for the antibodies to be determined, which antigen carries a label. A disadvantage of this method is the limited binding capacity of the solid phase since, apart from the antibody to be determined, other antibodies of the same globulin class are also bound.

The so-called bridge test opens up a possibility for carrying out an antibody detection and overcome the detectably-high non-specific binding problem of the indirect test format. The bridge test concept is described in EP0168689B189A3. In this method, a first binding partner, which is capable of specific binding to the antibody to be determined such as, for example, an antigen, is bound to a solid phase. The antibody to be determined binds to the solid phase-bound antigen. A second specific antigen, which is provided with a label, is also present in the test mixture. The antibody is detected by means of the label attached to the second specific antigen. The bridge test avoids the detectable non-specific signal because detection occurs via specific binding to the antibody paratope, as opposed to the Fc region. However, by avoiding this problem the bridge test is unable to classify the antibody class: if immunoglobulins of different classes but of the same specificity are present in the sample, the test does not distinguish between them. A two-step variation of this approach is described in U.S. Pat. No. 4,945,042A. In both cases, the methods are directed against all Ig specific to one antigen. They are not amenable to isotype-specific detection, and indeed distinguishing and quantifying different classes. Even more importantly, due to the use of a labeled antigen, both methods are not amenable to multiplexing, or the detection of multiple antibodies against multiple antigens. There thus lacks a for the multiplexed and iso-type detection of antibodies, that is, the ability to detect and measure antibodies against different targets while maintaining isotype classification.

Figure 9:
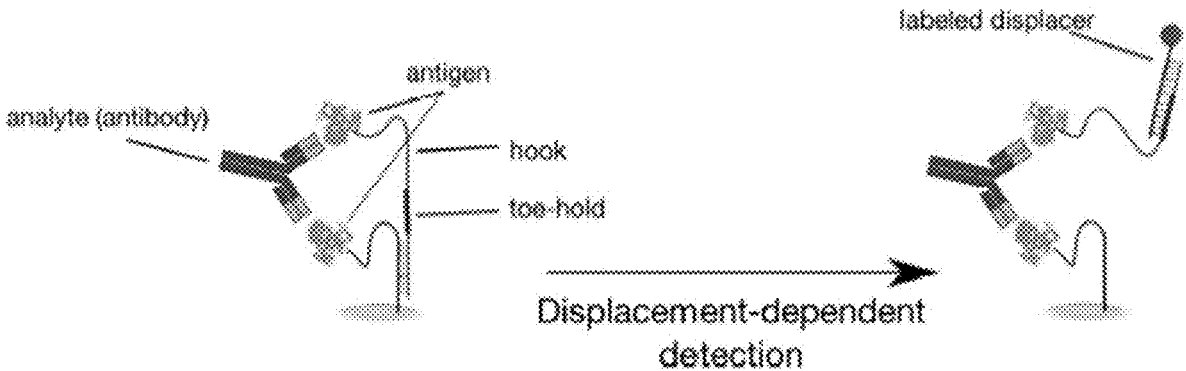
FIG. 9 shows a schematic diagram illustrating an embodiment of CLA with displacement-dependent detection for sandwich antibody detection. Identical antigens (e.g., peptides) are used as both capture and detection ABs, wherein one of the antigens is attached to a hook strand releasably attached to the anchor strand. Toe-hold mediated displacement using a labeled displacer agent (an oligo in this embodiment) performs the dual-function of displacing and labeling the hook strand. Fractions of labeled and released hook strands (shown) remain attached to the support only in the presence of the target antibody.

The colocalization-by-linkage (CLA) sandwich assay allows multiplexed measurement of antibodies while also overcoming the detectable non-specific binding issue and can significantly improve multiplexed serological analyses. Methods and systems provided herein overcome the non-specific detection issue by performing a dual-binder assay that does not rely on species-specific antibodies for detection. In this case, the analyte (here an autoantibody) is recognized and detected by two specific antigens. In such embodiments, recombinant or native antigens can be divided into two fractions, representing capture AB and detection AB, that are conjugated to a capture strand and a hook strand, respectively, wherein the capture strand and the hook strand are both linked to the same anchor strand, wherein the anchor strand is attached to the support (as in FIG. 9). As discussed previously, the flexibility of the hook strand can enable simultaneous binding of the analyte (here an antibody) to the capture AB and the detection AB (here identical proteins that are conjugated to distinct strands with distinct functionalities). Detection of the analyte presence proceeds using the "release-dependent transduction" (RDT) principle described herein, which relies on simultaneously labeling the detection binder and displacing it from the support. This step can be performed using DNA oligonucleotide displacement, among other strategies. which serve in some embodiments to address several sources of background noise and false-positives in multiplexed sandwich assays.

Figure 10:
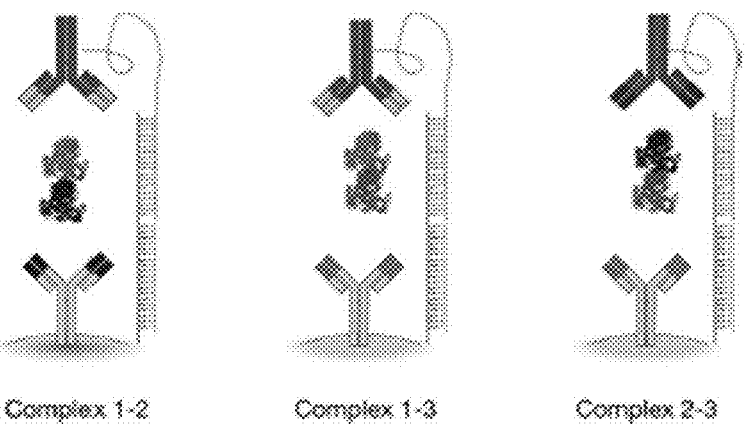
FIG. 10 shows a schematic diagram illustrating an embodiment of CLA used for detection of protein-protein interactions in multiplex, wherein arrays (planar or beads) are assembled with mismatched AB pairs, allowing detection of protein-protein interactions according to the AB pairs.

In particular, in some embodiments multiplexing of protein analyses will be significantly enabled by the methods and systems provided herein. For example, profiling of proteins such as cytokines and other soluble factors has been limited in conventional multiplexing due to reagent-cross reactivity. In some embodiments, methods and systems provided herein can address a major challenge in the multiplexed analyses of protein-protein interactions using ABs. For purposes thereof, AB pairs can be pre-assembled, each AB pair targeting one protein of interest, allowing for the CLA to detect interactions between the pair in question, as shown in FIG. 10. Because of the complete isolation of such multiplexed assays from another, cross-reactivity is reduced significantly, allowing combinatorial measurement of interactions across different protein-protein pairs. The modular approach of the fabrication method of the embodiments presented herein makes the implementation and fabrication of ABs pairs targeting different proteins relatively straightforward. For example, large batch fabrication of CLA on microparticles allows bulk functionalization of microparticles with capture ABs, followed by fractionation and addition of different detection ABs to every fraction.

In some embodiments, methods and systems provided herein can address another major challenge in the multiplexed analyses of post-translational modifications (PTM) using ABs. For example, accurate protein phosphorylation analysis can be used to reveal cellular signaling events not evident from protein expression levels. Current methods and workflows for quantifying the fraction of PTM of a specific protein are severely limited in multiplexing because PTM-specific ABs possess inadequate specificity for the protein itself (that is, a phosphor-specific AB is highly susceptible to the problem of reagent-driven cross-reactivity). As a result, conventional PTM panels are not multiplexed. The multiplexed CLA assay methods and systems provided herein can address this problem by confining the anti-PTM binder to an analyte-specific support (as in FIG. 11).

As may be understood by one skilled in the art, multiplexed detection of protein levels and their corresponding PTM fractions (Eg. proteins 1-10 and their phospho fractions) is impossible using traditional immuno-affinity methods. In particular, anti-phospho AB are not specific to the protein target, which makes a multiplexed ELISA susceptible to the cross-reactivity problem describe herein and amplifies weak antibody interactions with increased multiplexing, drowning-out the specific signals. For additional clarity, if protein 2 non-specifically binds to capture AB 10, the PTM AB will bind to both protein 2 and protein 10, yielding a non-specific signal on the protein 10 PTM assay. The present invention can overcome this problem by allowing specific dual-binding assays to be conducted in parallel without cross-reactivity.

In some embodiments, methods and systems provided herein can be used to measure the expression levels of proteins in multiplex and the fraction of these proteins that are modified by several PTMs (eg. phosphorylation, glycosylation, methylation, and acetylation). the post-translation modification comprises phosphorylation, glycosylation, ubiquitination, nitrosylation, methylation, acetylation, lipidation, or a combination thereof. In certain such embodiments where BMPs are used for multiplexing, several barcodes can be used for one target, wherein each barcode contains antibody pairs that target a variant of the same proteins. For example, barcodes 1-5 could be assembled using antibody pairs each wherein capture AB against STAT3, but wherein detection AB 1-5 target, respectively: anti-STAT3, anti-phosphorylation, anti-acetylation, anti-ubiquitination, anti-methylation. Additionally, barcodes 6-10 could be assembled using antibody pairs each wherein capture AB against p38, but wherein detection AB 1-5 target, respectively: anti-p38, anti-phosphorylation, anti-acety-lation, anti-ubiquitination, anti-methylation.

In certain embodiments, methods and systems provided herein may be used to measure the PTM fraction and total protein on a single-molecule, single-bead, or single-spot level. In such embodiments, the support can be composed of three antibodies, a capture AB and a detection AB to recognize the protein as previously described, and an additional PTM AB also tethered via an additional hook oligo. In such embodiments the additional hook may contain an additional label (such as a dye of different color or wavelength) and results in an additional read-out. When such embodiments are performed on BMPs and read-out via cytometry, each bead will relay information regarding both the concentration of total proteins and PTM, effectively providing a more accurate representation of the PTM fraction.

Embodiments of the present invention can also overcome the imprecision of detecting a set of protein concentrations caused by a fraction of the proteins in the sample being modified by a PTM, having aggregated, bound to autoantibodies or other interacting proteins, or different protein variants in a sample that may or may not be detected by a single antibody pairs. In certain such embodiments, using the methods and systems presented herein, the precision of multiplexed detection of several protein levels can be improved by targeting or sampling all such variants by including assays that target them. For example, in certain such embodiments where BMPs are used for multiplexing, several barcodes can be used for one target, wherein each barcode contains antibody pairs that target a variant, complex, aggregate, or protein-protein interactions that include the protein target.

For example, the present invention can address historical challenges towards detecting different variants of the same protein within the same sample, which can provide additional resolution and improve diagnostic sensitivity and specificity. Traditional multiplexing approaches face significant cross-reactivity challenges due to antibody mixing that limit the ability running multiplexed assays where each target is probed by two different antibodies. The methods and systems presented herein allow designing isolated BMPs containing each bivalent assays, with each assay being isolated from the other while being mixed in the same solution.

In some embodiments, a hook strand is a flexible and releasable linker and is an oligonucleotide, which allows for the formation of a capture AB-analyte-detection AB tertiary complex, such that upon release of one of the unbound hook strand oligos from the support, a signal is generated only in response to recognition of a sandwich capture AB-analyte-detection AB.

In some embodiments, there is provided a detection AB which is an antibody attached to a support, such as a microparticle, via a hook strand which is an oligonucleotide linked to the detection AB. The hook strand oligonucleotide is partially complementary to an anchor strand oligonucleotide attached to the support (e.g., microparticle) via a streptavidin/biotin interaction for example or a chemical bond, thus attaching the detection AB to the support. There is further provided a capture AB which is an antibody attached to the support and wherein the detection AB recognizes the same antigen but not the same epitope as the capture AB. In some embodiments, there is provided a displacer agent which is an oligonucleotide which contains a fluorescent label or a DNA barcode sequence and has a sequence complementary to the hook strand oligonucleotide, overlapping with the sequence of the anchor strand oligonucleotide so that the detection AB is released from the anchor strand oligo and thus may be released from the support in the absence of the target analyte. It should be understood that once the capture AB and the detection AB bind to the analyte, a tertiary capture AB-analyte-detection AB complex is formed on the support (e.g., on the microparticle). After formation of the tertiary complex, unbound detection AB is removed from the support by washing, while the tertiary complexes are retained on the support. The presence of the tertiary complexes on the support afterwards can be detected and/or quantified.

In some embodiments, methods and systems provided herein may be referred to as "colocalization-by-linkages assay on microparticles" or "CLAMP". CLAMP methods and systems described herein may be highly accessible and advantageous for users. For example, by providing microparticles that have pre-assembled AB pairs (pairs of capture and detection ABs), users can rapidly mix-and-match panels at will, perform multiplexed assays rapidly, and read-out the assay results using e.g. any multicolour flow cytometer. CLAMP assays provided herein can thus fit within existing experimental workflows in biology, and in some embodiments can be read out using any multicolor flow cytometer.

It will be appreciated that CLAMP embodiments are uniquely amenable for large, industrial-scale fabrication of multiplexed panels that avoid cross-reactivity. As opposed to planar arrays, CLAMPs can be fabricated separately in large batches, optionally stored, and then mixed prior to the assay. This fabrication method allows CLAMPs to be manufactured independently without interaction between non-cognate ABs, and hence without cross-reactivity during the manufacturing step, a key advantage over other CLA embodiments.

In some embodiments, where the support is a microparticle (MP), certain advantages may be obtained. For example, in some embodiments the ability to rapidly read out a large number of MPs by flow cytometry can afford increased precision and sample throughput In addition, MPs may be functionalized in large batches and then stored, used, and read-out while in solution, which can reduce lot-to-lot variability and enable quantitative analysis (Tighe, P. J., et al., Proteomics—Clinical Applications 9, 406-422, 2015; Jani, I. V., et al., The Lancet 2, 243-250, 2002; Krishhan, V. V., Khan, I. H. & Luciw, P. a. Multiplexed microbead immunoassays by flow cytometry for molecular profiling: Basic concepts; Tighe, P., et al., Utility, reliability and reproducibility of immunoassay multiplex kits. Methods (San Diego, Calif.) 1-7 2013; Fu, Q., et al., Clinical applications 4, 271-84, 2010).

Figure 2:
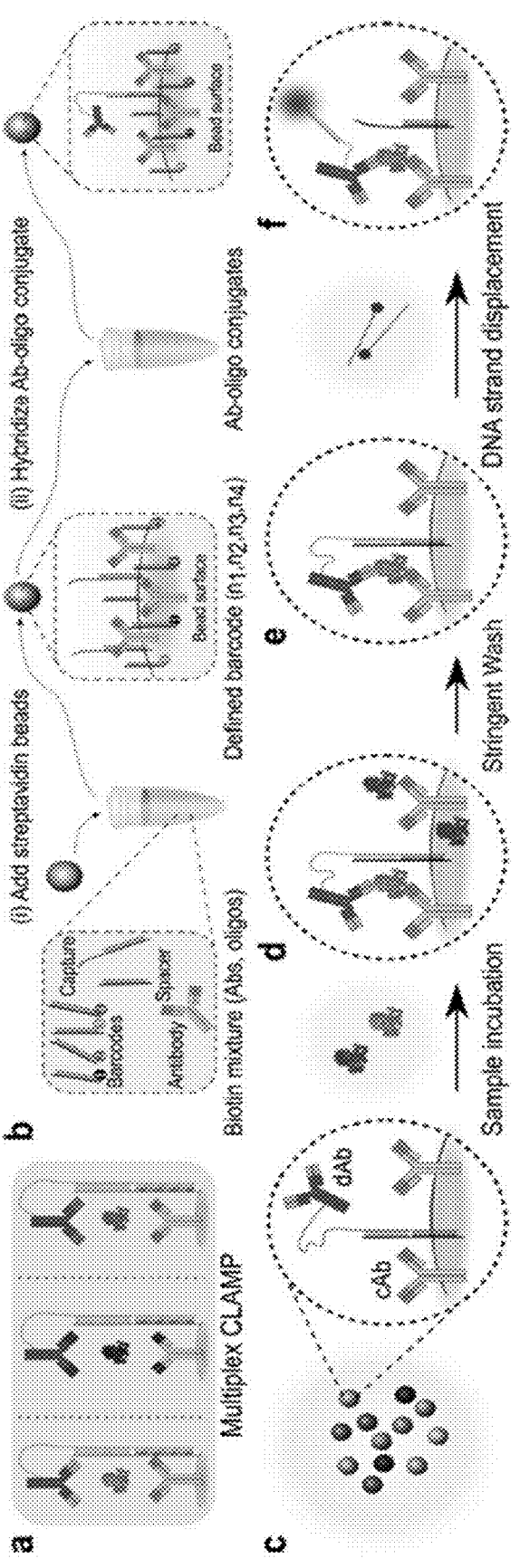
FIG. 2 is a schematic diagram that illustrates certain embodiments of the technology. (a) shows a CLAMP system in which cross-reactivity is prevented by colocalizing antibody pairs on individual beads using DNA linkages. In (b), each member of a CLAMP panel is made via one-pot fabrication of beads with a capture antibody (cAb) and ratios of fluorescent barcoding signals. In (c), bead sets, each with a cAb and a pre-hybridized detection antibody (dAb), are mixed to form a CLAMP panel. In (d), sample addition and target protein binding is shown. In (e), washing removes biomolecules bound non-specifically. In (f), sandwich complexes on each bead are labeled via a fluorescent DNA strand-displacement of the dAb.

In some embodiments, methods and systems provided herein can reduce or eliminate reagent cross-reactivity. As shown in FIG. 2a, which illustrates one embodiment of CLA, the pre-colocalization of two sets of antibodies on a surface using DNA oligonucleotides as flexible and addressable linkers, can eliminate interaction between non-cognate antibodies. Further, upon release of one of the flexible linkers from the surface, a signal is generated only in response to a sandwich antibody-antigen-antibody recognition.

FIGS. 2B-2F show the nanoscale architecture and operating principle of CLAMP, in accordance with one embodiment. CLAMP populations were created through a one-pot functionalization of microparticles with defined ratios of fluorescent oligonucleotides and antibodies (FIG. 2B), followed by hybridization of hook oligo-detection Ab (dAB) complexes to complete the construction of the CLAMP (FIG. 2B). In an embodiment, stable biotin-streptavidin bonds are used for reagent linkages/attachments, with bead sets stored after fabrication. Next, monovalent antibody-oligo conjugates are assembled as pairs on the barcoded bead sets via hybridization (i.e., antibody pairs A1-A2 and B1-B2 are pre-assembled on beads A and B, respectively) (FIG. 2C), and bead sets are then pooled together. When a CLAMP panel is added to a sample, target proteins generate sandwich complexes, while non-specifically bound proteins do not form complete sandwiches (FIG. 2D). After incubation, stringent washing removes non-specifically bound proteins (FIG. 2E). Next, DNA strand displacement is used to simultaneously dehybridize and label one antibody of the sandwich on each bead population, which ensures that only sandwich binding events generate a signal (FIG. 2F). Finally, CLAMP panels are automatically read-out and bead sets decoded using any commonly available multicolor flow cytometer.

In some embodiments, CLAMP panels can have lower development costs than traditional immunoassays; not only is costly re-optimization of panels avoided as new target analytes are added, but CLAMP can also use significantly lower quantities of antibodies per assay.

In some embodiments, in addition to overcoming reagent cross-reactivity, the pair of surface-tethered antibodies in CLAMP can result in a binding avidity effect, giving CLAMP further advantages over conventional sandwich immunoassays. CLAMP can exhibit a higher affinity for targets, as the off-rate (koff) of targets from antibody sandwich complexes in CLAMP can be much lower than in assays using sequential antibody addition. In some embodiments, CLAMP assays can be stringently washed after incubation, reducing assay background and improving specificity. In addition, in some embodiments CLAMP may have a reduced liability for false positives: mis-binding events in CLAMP do not form complete sandwich complexes, and hence they do not lead to false positive signals.

In any immunoassay protocol, the washing step is critical to the assay performance. Thorough washing in the assay reduces background signal by removing unbound signal transducing molecules, as well as low affinity non-specific binding events, and hence improving assay sensitivity. However, over-washing in a typical sandwich immunoassays (e.g. ELISA) can have adverse effects, as the dissociated antibody-antigen complexes can be removed, resulting in lower assay signal. Compared to typical immunoassays, CLAMP assays can be washed more stringently by increasing the number of washing steps, and/or using high ionic strength buffers, decreasing the background signal without the risk of losing the true signal. This can be achieved in some embodiments, where the simultaneous binding of a pair of surface tethered antibodies, to two different epitopes of the same analyte (that is, increased binding avidity) can result in a much lower effective off-rate (koff) in comparison to conventional sandwich assays In an embodiment, the displacer strand displaces the hook by binding to the anchor strand. In this embodiment, the label is a sequence on the hook strand within the hook-anchor hybrid and hence is initially inactive or hidden. To stabilize the signal through the re-bind step In this embodiment, the bridge strand may be designed to hybridize to the displacer and the hook strand specifically, hence reconnecting the hook strand and detection AB to the anchor stand. The active label representing the presence of a target molecule is thus tethered on the support in a stable format.

In another embodiment, the displacer strand binds preferentially to the hook to displace it from the anchor and hence the surface. In this embodiment, the label is a sequence on the displacer strand. To stabilize the signal through the re-bind step in this embodiment, the bridge strand may be designed to hybridize to the displacer and the anchor, hence reconnecting the hook strand and detection AB to the anchor strand. The active label representing the presence of a target molecule is thus tethered on the support in a stable format.

In some embodiments, one or both of the specific binding sites on the bridge reagent can be DNA sequences. The bridge reagent is a DNA oligo that include complementary sequence to the displacer on one end and complementary sequence to the hook or anchor stand on the other end. The length of the hybridizing segments on either end of the bridge oligo can be the same or different to suit various target systems of different physical geometry, affinity and required stability.

In some embodiments, one of both ends of the bridge reagent can include a covalent linker. The connections of the linker to the hook and the anchor strand can be achieved in various conjugation chemistry, eg. biotin-streptavidin and click chemistry. After displacement, the bridge reagent is added to the incubation. The experimental conditions eg.

pH, temperature, additional catalyst, are adjusted in favor of the conjugation reaction to reach maximum conjugation efficiency. The covalent bond formed can ensure the stability of the signal over time and harsh conditions eg. stringent washing and during shipment, that leads to breaking the bonds between targets and capture detection reagent.

In the embodiments a dye is used to report the presence of the analyte, various detectable agents can be used including, but limited to: radionuclides; fluorescent reagents eg. fluorophores, organic polymer dyes, R-Phycoerythrin, quantum dots; chemiluminescent and bioluminescent agent; nanoparticles; nanoclusters; paramagnetic metal ions; and colorimetric label, eg. peroxidase enzyme label, dyes, colloidal gold. The label of choice can be implemented depending on the criteria such as stability in certain sample matrix, pH and temperature requirements from other reagent, the ability to be conjugated to the displacer reagent, interference of the analyte and assay mechanism. The term "fluorescent polymer" refers to polymers with multiple fluorophores. The fluorescent polymer can be synthesized via various polymerization reaction using fluorophore as monomer, includes atom transfer radical polymerization (ATRP), ring-opening metathesis polymerization (ROMP), reversible addition-fragmentation chain transfer polymerization (RAFT), nitroxide-mediated polymerization (NMP) or free radical polymerization. The fluorescent polymer can also be prepared via the post functionalization of various polymers with fluorophores. The polymers refer to various linear polymers, star polymers, or block polymers, and the backbone of the polymers include, but are not limited to poly(ethylene glycol) (PEG), poly (ethylene oxide) (PEO), poly (D, L-lactic-co-glycolic acid) (PLGA), polyacrylamide, poly (N-isopropylacrylamide) (PNIPAM), poly[tri(ethylene glycol)ethyl ether methacrylate] (pTriEGMA), poly(propylene oxide) (PPO), poly(ethyleneimine) (PEI), poly(L-lysine) and poly (pyrrole).

Figure 36:
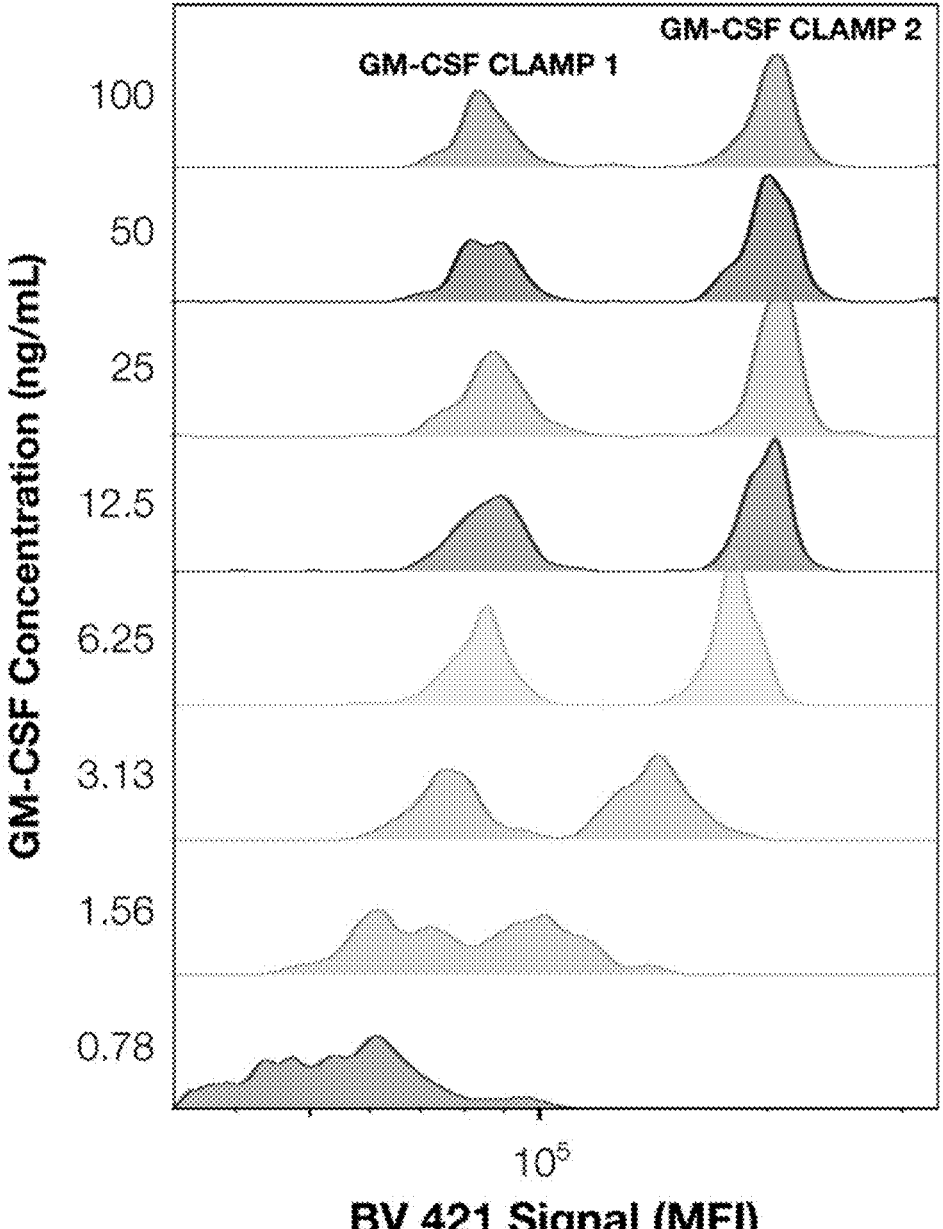
FIG. 36 shows how multiple CLAMPs against the same target (here GM-CSF), designed to respond with differing effective affinity (Kd), can be combined as a single sensor with two outputs that together extend the dynamic range without requiring additional barcodes. Here, the signal distribution in BV421 channel is plotted for the GM-CSF barcode, which again is the same both, against different dilutions of GM-CSF.

Fluorescent polymer dyes are useful for extending the dynamic range for detection of a detectably-labeled displacer reagent (FIG. 36). The term "dynamic range" refers to the magnitude of the measuring range of an assay and is here defined as ratio of upper detection limit (UDL) to lower detection limit (LDL). If not indicated otherwise we use the term measuring range as concentration values starting at the LDL and ending at the UDL. Principally other sensitivity terms may be used than the LDL, like LOD or LOQ, and also other terms describing the upper measuring range than the UDL may be used to calculate the dynamic range.

In some embodiments, to increase the signal amplification and detection sensitivity, a polymer dye such as Brilliant Violet (eg. Brilliant Violet 421 or BV421) or Super Bright 436 may be used as a label. In such embodiments, the polymer dyes may be conjugated to the displacer oligo. The conjugation may be carried out using covalent or non-covalent means, and can be monovalent or multivalent. In such embodiments the release-dependent transduction can be carried out using the displacer-polymer dye to displace the hook oligo. In other embodiments, the label may be a sequence on the displacer oligo, which can be targeted in a later step using a complementary oligo conjugated to the polymer dye.

Multiplexing offers several distinct advantages over singleplex immunoassay, particularly the small sample volume and times required to obtain the same amount of information. Traditional singleplex immunoassay eg. ELISA can been largely miniaturized to reduce sample volume requirements and may be run in parallel using microfluidic approach. However, the singleplex assay format bears fundamental limitations that the target sample need to be split for individual reaction and each of the reaction need to be individually processed. To address these limitations, multiplexing enables multiple analytes to be profiled simultaneously. Planar and bead-based assay are two commonly used formats to facilitate multiplexing. Barcoded (or encoded) microparticles, in particular, are often used in multiplexed suspension assays as they allow particles in a large mixture to be distinguished. The methods of barcoding include, but not limited to spectral, graphical, or chemical means.

In some embodiments, multiplexing and labeling can be simultaneously achieved by CLAMP reagents that use specific DNA sequences as barcodes, wherein specific sequence is used as the label or as barcodes for a specific analyte. For example, specific barcoding DNA sequence can be included in the hook strand, whereby after the detection-by-displacement, the hook strand from a singleplex or multiplex assay can be released from the solid support and read by methods including, but not limited to: hybridization-based microarrays, eg. solid phase DNA chips and beads arrays; Single molecule methods, eg, nanostring; and DNA sequencing methods, eg. next generation sequencing (including Roche 454, Illumina HiSeq, Pacific Biosciences SMRT and the like) and single molecule sequencing (including Oxford nanopore platform and Pacific Biosciences SMRT platform and the like).

In some embodiments wherein a DNA sequence is used as a label, the signal can be identified and quantified via DNA-based detection methods. In a singleplex assay, these methods include, but not limited to: Enzymatic methods, e.g. Polymerase chain reaction (PCR), Loop-mediated isothermal amplification (LAMP), helicase-dependent amplification (HDA) and strand displacement amplification (SDA). For quantitative approach, the label sequence can be detected by a quantitative polymerase chain reaction (qPCR) platform eg. Fluidigm BioMark, whereby the label sequence can be replicated and readout by DNA fluorescent staining. The fluorescent intensity can be recorded after each PCR cycle and the fluorescent intensity growth over cycle numbers may be used to quantify the label sequence concentration. This approach can reach the detection limit of a few to a few tens of copies of the label sequence from the sample. Alternatively, Non-enzymatic methods including, but not limited to: Hybridization Chain Reaction (HCR) and catalyzed hairpin assembly (CHA). In a multiplex assay, an multiplex PCR can be designed using a few pairs of specific primers and the product can be labeled with different fluorescent probe. Simultaneous detection can be achieved with a multiplex PCR platform, eg. Biorad CFX96 Touch Real-Time PCR Detection System and QuantStudio 12K Flex Real-Time PCR System.

As can be appreciated by those skilled in the art, the limit of detection is a key performance indicator in protein assays. A pg/mL detection sensitivity is necessary to detect many signalling analytes, such as cytokines, that are endogenously in low abundance. Improving the limit of detection necessitates a low assay background and a high signal amplification. In particular, where the read-out is a fluorescent signal, signal amplification is proportional to the number of labels (eg. fluorescent dye) that can be used to detect the presence of an individual protein. Assay formats with which each target recognition event transduced with only one dye often yield detection threshold above the concentration of the analyte, and hence an insufficient detection limit. In order to improve sensitivity, DNA oligo constructs that form a key part of the present invention can be utilized to amplify the transduced signal.

In some embodiments where CLAMP reagents are used in a high sensitivity assay, the hook strand can a specific DNA label sequence that can be amplified using enzymatic methods eg. isothermal rolling circle amplification (RCA) or non-enzymatic methods eg. hybridization chain reaction (HCR) and immuno-Saber with single or multiple branches. For enzymatic amplification using RCA, the hook strand or displacer strand contains a label sequence that can be used as the primer of the DNA synthesis. Incubated with a circular DNA template, DNA polymerase, the label sequence can initiate the DNA replication. The DNA polymerase can continue the replication which results in a long concatemer ssDNA containing tens to hundreds of tandem repeats of the circular template. Imager strands with a dye of the complementary sequence to the template can be added and hybridized to the ssDNA concatemer and therefore yield amplified the signal by tens to hundreds of folds.

In another embodiment, non-enzymatic HCR amplification method can be used to amplify the signal generated by the displacement reaction, whereby a label sequence included in the hook strand or the displacer strand can trigger a hybridization chain reaction (HCR). Two kinetically trapped DNA hairpins are added to the reaction where the label sequence on the hook strand triggers a chain reaction of alternating each of the hairpin to hybridize onto the amplification polymer. Each of the DNA hairpin are modified with one or multiple dyes. The signal is therefore amplified due to the increasing number of dyes added onto the amplified polymer, which stemming from the hook strand. In another embodiment, the label sequence in the hook strand or displacer strand may be the starter for branched DNA assemblies. Branch strand and imager strand are added in the reaction. Branch strand bears sequence that partially complementary to the starter stand on the hook and repeated sequence that complementary to the fluorophore carrying imager strands. By hybridizing to multiple branch strands on the same hook and in turns multiple imager strands, the number of dyes carried by a single hook strand has been amplified.

There are a number of methods whereby the CLAMP reagents can be attached onto solid surfaces, for example on the surface of MPs. A commonly used technique herein is by using CLAMP reagent the are covalently bound to a biotin molecule, to which are attached onto a surface that is covalently pre-coated with streptavidin. In other embodiments, CLAMP reagents can be directly linked onto the surface using covalent bonding. In such embodiments, a covalent chemistry referred to as "click chemistry" can be used, whereby alkynyl-modified CLAMP reagents that are designated to be bound onto the surface such as the capture AB and DNA linkage, react to azide functional group present on the surface. In another embodiment, amino-modified DNA and capture ABs can be covalently bound onto a carboxylated surface using carbodiimide chemistry, whereby the carboxyl groups on the surface are activated with 1-Ethyl-3-[3-dimethylaminopropyl]carbodiimide hydrochloride reagent in the presence of sulfo-NHS (N-hydroxysulfosuccinimide) to form a sulfo-NHS-ester intermediate. The intermediate is then replaced by the primary amine of the DNA and detection ABs to form a covalent amide bond.

As used herein, the term "displacer agent" refers to an agent that directly or indirectly causes or initiates release of the releasable linkage between the anchor strand and the hook strand, thereby releasing the hook strand (and the detection AB linked thereto) from the support. The mechanism used by the displacer agent is not particularly limited.

For example, the displacer agent may directly or indirectly cause or initiate cleavage, displacement, or unbinding of the linkage between the anchor strand and the hook strand; other mechanisms are possible and are also contemplated. In some embodiments, the hook strand is displaced from the anchor strand using a DNA oligonucleotide that hybridizes to the hook strand and/or the anchor strand. Examples of displacer agents include but are not limited to a displacement DNA oligonucleotide, a source of mono- or poly-chromatic light, a restriction enzyme, and a reducing agent such as dithiothreitol (DTT). In some embodiments, where photocleavable DNA segments are used, the displacer agent may be a light which effects release via a photocleavage reaction. In some embodiments, the displacer agent is labeled, e.g., with a dye, a fluorophore, a specific DNA sequence, an enzyme, a biotin moiety, and the like. When the displacer agent is labeled, it can serve the dual-function of releasing the hook strand and labelling it simultaneously.

Figure 18:
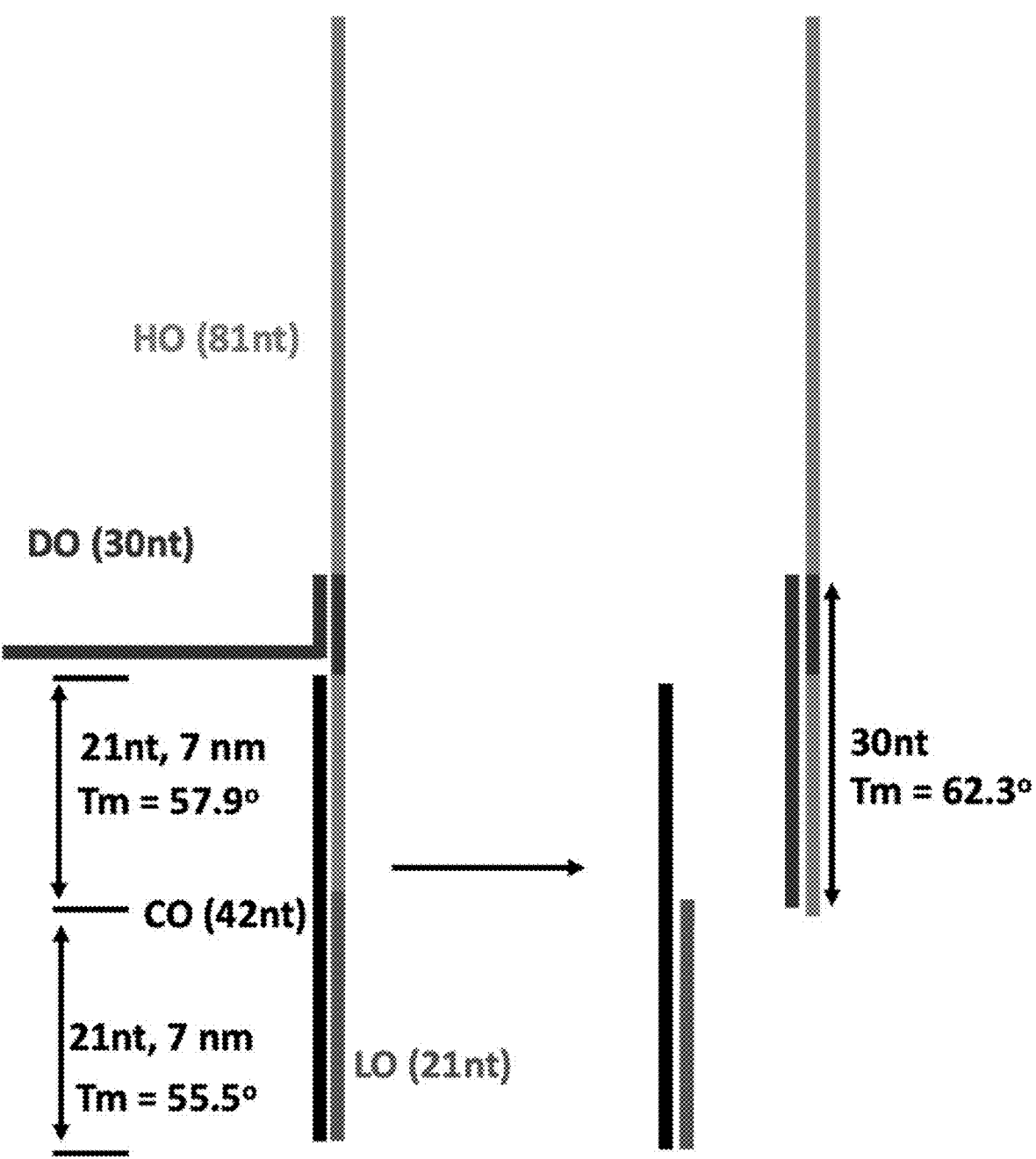
FIG. 18 shows sequences and melting temperatures of oligonucleotides used in CLAMP in accordance with one embodiment. The capture oligo (CO, 42 nt) is bound to the streptavidin surface via 5' biotin, and links both the 3' fluorescent labeling oligo (LO, 21 nt) and 5' antibody-conjugated hook oligo (HO, 81 nt) to the microparticle surface. A displacer oligo (DO 30 nt) initially binds to a 9 nt toehold on the hook oligo to displace the HO-CO hybrid.

In some cases the hook strand may be a polymer chain, such as polyethylene glycol (PEG). The polymer chain may consist of 60, 80, 100, 150, 200, 400, 600, 800, or more than 800 moieties. In some cases the hook strand may be a polypeptide chain. The polypeptide chain may consist of 60, 80, 100, 150, 200, 400, 600, 800, or more than 800 amino acid residues. In some cases the hook strand may be a DNA oligonucleotide. The oligo may consist of 20, 40, 60, 80, 100, 120, 140, 160, 180, 200, or more than 200 nucleotides. The hook strand may be bound directly to the support, or releasably bound to an anchor strand. In the preferred embodiment, as depicted in FIG. 18, the hook strand oligo measures 81 nucleotides in length, having 21 nucleotides complementary to the anchor strand and a further 9 nucleotides complementary to a displacement strand.

In cases where the hook strand is bound to an anchor strand, the anchor strand may be a polymer chain, such as polyethylene glycol (PEG), chitosan, or hyaluronan. The polymer chain may consist of 60, 80, 100, 120, 120, 140, 160, 180, 200, or more than 200 moieties. In some cases the anchor strand may be a polypeptide chain. The polypeptide chain may consist of 60, 80, 100, 120, 120, 140, 160, 180, 200, or more than 200 amino acid residues. In some cases the anchor strand may be a DNA oligonucleotide. The oligo may consist of 20, 25, 30, 35, 40, 45, 50, 55, 60, or more than 60 nucleotides; generally the anchor strand oligo being shorter than the persistence length of double-stranded DNA. In the preferred embodiment, as depicted in FIG. 18, the anchor strand measures 42 nucleotides in length, having 21 nucleotides complementary to the labelling oligo and 21 nucleotides complementary to part of the hook strand oligo. These dimensions were determined experimentally to provide a very low rate of unbinding of the complex at relevant conditions.

In some embodiments, the displacing agent may be a reducing agent such as dithiothreitol (DTT). For example, the hook strand may consist of two or more PEG polymer chains conjugated with disulfide bonds, wherein the introduction of a DTT-containing solution induces cleavage via thiol-disulfide exchange reactions. In an alternative embodiment, the displacing agent may be a buffer of higher or lower pH. For example, the hook strand may consist of two or more polypeptide chains conjugated with hydrazone bonds, for instance via modified amino acid cysteine hydrazide, wherein the introduction of an acidic buffer cleaves the hydrazone bond. In another embodiment, the displacing agent may be a source of mono- or poly-chromatic light. For example, the hook strand may consist of a DNA oligonucleotide which contains a photo-cleavable linker arm, wherein exposure to UV light induces cleavage of the strand. In another embodiment, the displacing agent may be an enzyme, such as cathepsin. For example, the hook strand may consist of two or more PEG polymer chains conjugated to a valine-citrulline or phenylalanyl-lysine dipeptide, wherein the introduction of a solution containing cathepsin B or D respectively induces cleavage at the peptide linker. In the cases described herein it may be necessary to use a different conjugation method between the detection AB and hook strand, if the cleaved strand is to be used or targeted for labelling. It should be understood that the examples described herein are not restrictive, but may be combined as appropriate; ie. a cleavable PEG polymer chain may contain a hydrazone bond or photo-cleavable linker.

In cases where the hook strand and anchor strand are DNA oligonucleotides, the displacing agent may be a heated buffer solution that melts the DNA duplex and releases the hook strand. Alternatively, the displacing agent may be another oligonucleotide which releases the hook strand via a toe-hold displacement reaction. The length of the toe-hold may be 1, 2, 3, 4, 5, 6, 7, 8, 9, 10, or more than 10 nucleotides. In the preferred embodiment, as depicted in FIG. 18, the toe-hold measures 9 nucleotides in length. According to Zhang, D. Y. and Winfree, E., Journal of the American Chemical Society, vol. 131, issue 47, pp. 17303-17314, 2009, the displacement reaction rate increases with the length of the toe-hold region until about 9 nucleotides, beyond which additional nucleotides have no effect on the reaction rate.

In cases where the support is a particle, its size is not particularly limited. In the preferred embodiment, the particle is a 2.8 μm paramagnetic bead with a streptavidin monolayer. This bead type has been determined experimentally to provide high surface area for assays while also being easy to manipulate. In alternative embodiments, it may be more desirable to use particles of 1 μm or even 100 nm in diameter. For example, if the plex number is increased while all other parameters are maintained then the number of beads per target decreases, reducing the accuracy of the data. However, if the total number of beads is increased without increasing the assay volume then both the beads and the released detection ABs will be at a "high" concentration with respect to each other, increasing the rates of labelled, released detection ABs cross-reacting and producing false-positive results. In this case the use of smaller beads would be desirable in order to reduce the volume of beads in solution as well as the concentration of ABs released in solution, since a smaller bead would have proportionately less detection antibodies on its surface. Alternatively, in some cases it may be more desirable to use a particle of 10 μm or even 50 μm in diameter. For example, if using non-magnetic beads then it may be necessary to use a filter to wash away the sample, particularly in the case of a complex sample. A larger bead might be selected to establish adequate separation between the largest un-lysed cell or debris in the sample in order to ensure good filtration.

In some embodiments, methods and systems provided herein can address challenges in profiling of extracellular vesicles. Current analysis technologies only address average expression values across populations, whereas it has been demonstrated that extracellular vesicles have highly heterogeneous expression of surface proteins from the parent cells. For purposes thereof, AB pairs can be pre-assembled on a support such that each AB targets a different surface protein of interest on the extracellular vesicle (for example, CD9 and CD63). Following incubation with the sample, displacement of the hook strand and washing away of unbound detection AB, observation of both the support identity (an encoded bead or location on a surface) and a labelled hook strand would indicate association of the two surface proteins.

In some embodiments, methods and systems provided herein can be used to detect DNA or RNA sequences within short fragments or longer strands of nucleotides. In such cases, the capture and detection ABs would be RNA or DNA oligonucleotides complementary to different parts of the target sequence. The partial sequences recognized by the ABs do not need to be adjacent within the target. Following incubation and washing of unbound sample, signal transduction can proceed via labeled strand displacement, as described herein.

In some embodiments, methods and systems provided herein can address challenges in detecting the secretions of cells. For purposes thereof, the complex may consist of three ABs, wherein one AB targets a surface marker specific to the cell type examined while two other ABs target a protein, DNA, RNA, or other secreted molecule of interest; and wherein one of the two secretion-targeting ABs is bound directly to the support while the other is releasably attached, directly or indirectly, to the support via a flexible hook strand. In such cases, the surface marker-specific AB would localize the support to the cell (ex. An encoded bead) while the secretion-specific ABs would capture secreted molecules. Signal transduction can then proceed via labeled strand displacement, as described herein, and signal quantitation may be via fluorescent microscopy. The use of release-dependent signal transduction offers greater specificity than conventional sandwich assays against secreted targets. In some embodiments, the surface marker-specific AB may also be releasably bound to the support, such that after collection of cell secretions the support may be cleaved from the cell and collected for analysis, such as by flow cytometry. In alternative embodiments, the support may remain bound to the cell to act as a label such that the cell may be isolated via fluorescence-activated cell sorting for further analysis.

In some embodiments, assembling the CLAMP reagents on the surface of magnetic microparticles (such as the commercially available Dynabeads by Invitrogen), offers advantages in liquid handling in both the fabrication and the CLAMP assay protocols. Using magnetic separators, either in tube rack or plate holder formats, allow the rapid aggregation of the beads for the removing of the liquid supernatant, in protocols such as, but not limited to washing steps or buffer exchanges. Magnetic microparticles are also compatible with automated liquid handling stations, for example the Biomek line of instruments by Beckman Coulter. As such, embodiments of the magnetic CLAMP MPs can be seamlessly implemented in protocols and instrumentation used in throughput applications.

As is understood by one with ordinary skill in the art, commercial microparticle-based ELISA technologies and systems are not amenable to long-term storage via freezing. Common, if not all, bead-based reagents are shipped and stored at 4 degrees Celsius. Bead manufacturers, such as Dynabeads, do not recommend freezing microparticles, especially after they have been labeled or coated with antibody or DNA binding reagents.

As those skilled in the art will appreciate, the timing and length of various assay steps are critical to performance and reproducibility of immunoassays. That is because various binding events, specific or non-specific, possess various binding on-rates (k_on) and off-rates (k_off). Hence, it is critical that all samples observe close to exactly the same procedure and timing from the moment they are mixed with the binding reagents.

In the present invention, it was surprisingly turned out that storage of fully-assembled CLAMPs in freezing temperatures (such as −20 degrees Celsius) results in equal or better assay performance compared to CLAMPs stored at chilled temperatures (4 degrees C.). In some embodiments, the frozen CLAMPs can be mixed and distributed into plates before freezing. In some embodiments, multiplexed CLAMPs reagents can be mixed, blocked, and stored in plates at −20 C for several months before utilization in an assay. In some other embodiments, frozen multiplexed CLAMPs can be thawed in staggered approach to ensure all CLAMPs observe the same assay protocol timing.

In an aspect, disclosed is a composition for the detection or quantification of one or more analytes in a sample, comprising a microwell plate that is stored and shipped at freezing temperatures, wherein at least some wells in the plate comprise a mixture of at least two barcoded microparticles coated with at least one type of affinity binders.

In some embodiments, the microparticles are colocalization-by-linkage macroparticles designed to bind analytes in a sandwich format, as described in this invention.

In some embodiments, the microwell plate is 96-well plate. In some other embodiments, the microwell plate is a 384-well plate. In yet other embodiments, the microwell plate is a 1536-well plate. In some embodiments, the microwell plate is a non-standard format with number of wells of at least 2.

In one embodiment, there is provided a method for the detection or quantification of one or more analytes in a sample, comprising the steps of: (1) at the manufacturing site preparing a microwell plate at least partially filled with a mixture of barcoded microparticles, (2) storing said microwell plate at freezing temperatures, (3) transporting said microwell plate, using cold chain or other approaches to the test site.

In some embodiments, the microparticles are colocalization-by-linkage macroparticles designed to bind analytes in a sandwich format, as described in this invention.

In one embodiment, there is provided a method for the detection or quantification of one or more analytes in a sample, comprising the steps of: (1) at the manufacturing site preparing a microwell plate at least partially filled with a mixture of barcoded microparticles, (2) storing said microwell plate at freezing temperatures, (3) transporting said microwell plate, using cold chain or other approaches to the test site, (4) receiving the raw result of the data back from the test site and performing the analysis.

In one aspect, disclosed is a composition for the detection or quantification of an analyte in a sample, comprising a microwell plate that is stored and shipped at freezing temperatures, wherein at least some wells in the plate comprise a mixture of at least two barcoded microparticles coated with antigen specific affinity binders.

Commercial ELISA kits offer the user the reagents needed for the determination of the unknown samples as well as validated test systems. Typical kits shipped to the user contain, separately, all reagents required for the test execution in optimized concentrations and amounts as well as a detailed protocol for performing the test. Bead-based multiplexed ELISA technologies and systems, such as the xMAP based panels, often offer the user pre-mixed antibody-coated barcoded beads to minimize the preparation steps. However, the burden of correctly distributing the beads in the 96- or 384-well plates still lies on the user and at larger scale quickly becomes the key operational challenge. Despite the availability of many automation instruments, the ability to quickly, evenly and homogeneously distribute microparticles onto plates is a challenging task that becomes the bottleneck for preparing any large-scale experiment.

In some embodiments, the methods and systems presented herein can be packaged into a test kit that is simpler, faster and more robust to run for the end-user. Multiplexed CLAMPs can be combined into a single panel, mixed and distributed at appropriate concentrations within 96- or 384-well plates. The "CLAMP Plates" may be stored at freezing temperatures, and shipped frozen to the end-user. The CLAMP Plates integrate allow for much reduced preparation times and enable the user to follow the simple two-step process to initiate the test: thaw plate for 30 mins on ice, add unknown solutions in the wells.

In some embodiments, the multiplexed CLAMP reagents are prefabricated, mixed, and distributed into plates that are shipped frozen to the end-user. In other embodiments, the CLAMP reagents are shipped separately to the user. In some embodiments, the plates are blocked and filled with multiplexed CLAMP reagents.

The availability of flow cytometers provides users the flexibility to execute the assay and read-out in-house, which allows for quicker iterations for assay development. However, flow cytometers may not always be available to the user, as it may be a shared or leased equipment by the academic institute. In large scale experiments, such as when the measurement of >100 samples in a single experiment is necessary, flow cytometers become the bottleneck for such same-day experiment which often important for quantitative comparison in biology.

The methods and systems provided herein allow faster and higher throughput analyses unencumbered by read-out throughput. In some methods provided herein, multiplexed CLAMPs reagents can be frozen after the sample washing step. At this point during the assay analysis, the analytes have been all captured by their respective CLAMPs, the unbinding is minimal due to the bivalent binding to both capture AB and detection AB. In some embodiments, CLAMPs using a re-bind component can be used to further stabilize the signal and allow storage both at chilled or freezing temperatures. This process enables more samples to be processed altogether in the same experiment on the same day. The frozen samples can then be sequentially thawed and analyzed at-will, enabling more robust, quantitative data across plates and wells.

For example, provided herein are methods for detecting and quantifying an analyte within a sample, comprising: (a) contacting the sample with a colocalization by linkage assay (CLA) complex comprising: (i) a support; (ii) a first anchor element attached to the support; (iii) a second anchor element attached to the support; (iv) a capture agent releasable coupled with the first anchor element, wherein the capture agent is configured to bind the analyte; (v) a detection releasably coupled with the second anchor element, wherein the detection reagent agent is configured to bind the analyte; (c) providing a detectable displacer agent configured to couple with the detection agent and release the detection agent from the first anchor element; and (d) detecting a presence or absence of the detectable displacer agent; thereby indicating the presence or absence of the analyte; wherein the method comprises a freezing step after steps (a), (b), or (c).

In some embodiments, the detectable displacer agent is detected when the analyte is bound to the capture agent and the detection agent. In some embodiments, the detectable displacer agent is not detected when the analyte is not bound to capture agent, the detection agent, or both. In some embodiments, the first anchor element comprises a first polynucleotide comprising a first anchoring nucleic acid sequence. In some embodiments, the second anchor element comprises a second polynucleotide comprising a second anchoring nucleic acid sequence. In some embodiments, the capture agent is coupled to a third polynucleotide comprising a third nucleic acid sequence complementary to the first anchoring nucleic acid sequence. In some embodiments, the third nucleic acid sequence is hybridized to the first anchor nucleic acid sequence.

In some embodiments, the detection agent is coupled to a fourth polynucleotide comprising a fourth nucleic acid sequence complementary to the second anchoring nucleic acid sequence. In some embodiments, the fourth nucleic acid sequence is hybridized to the second anchor nucleic acid sequence. In some embodiments, the detectable displacer agent comprises a fifth polynucleotide comprising a fifth nucleic acid sequence complementary a region of the fourth nucleic acid sequence. In some embodiments, the fifth polynucleotide comprises fifth nucleic acid sequence complementary the region of the fourth nucleic acid sequence, and wherein (c) further comprises hybridizing the fifth polynucleotide to the fourth polynucleotide, thereby releasing the capture agent from the support.

In some embodiments, one or both of the capture agent and detection agent is an antibody, an antibody fragment, an aptamer, a modified aptamer, a somamer, an affimer, an antigen, a protein, a polypeptide, a multi-protein complex, an exosome, an oligonucleotide, or a low molecular weight compound. In some embodiments, the capture agent and detection agent are an antibody, an antibody fragment, an aptamer, a modified aptamer, a somamer, an affimer, an antigen, a protein, a polypeptide, a multi-protein complex, an exosome, an oligonucleotide, or a low molecular weight compound. In some embodiments, the capture agent and detection agent are an antibody or an antibody fragment. In some embodiments, the capture agent and the detection agent bind different epitopes on the analyte.

In some embodiments, the analyte is an antigen, an antibody, an affimer, an aptamer, a modified aptamer, a somamer, an antibody fragment, a protein, a polypeptide, a multi-protein complex, an exosome, an oligonucleotide, a hormone, a modified oligonucleotide, or a low molecular weight compound. In some embodiments, the capture agent and the detection agent are both antigens, and the analyte is an antibody. In some embodiments, the capture agent and the detection agent are different antigens, and the antibody is a bispecific antibody or multi-specific antibody.

In some embodiments, the freezing step comprises storing a composition or product of (a)-(c) at a temperature below −20, −6, −5, 0, 1, 2, 4, 5, 6 degrees Celsius. In some embodiments, the freezing step comprises storing a composition or product of (a)-(c) at a temperature below 5 degrees Celsius. In some embodiments, the freezing step comprises storing a composition or product of (a)-(c) at a temperature below 0 degrees Celsius. In some embodiments, the sample of compositions herein are stored at temperature a temperature of about −20 degrees Celsius to about 6 degrees Celsius. In some embodiments, the sample of compositions herein are stored at temperature a temperature of about −20 degrees Celsius to about −15 degrees Celsius, about −20 degrees Celsius to about −6 degrees Celsius, about −20 degrees Celsius to about −5 degrees Celsius, about −20 degrees Celsius to about 0 degrees Celsius, about −20 degrees Celsius to about 5 degrees Celsius, about –20 degrees Celsius to about 6 degrees Celsius, about –15 degrees Celsius to about –6 degrees Celsius, about –15 degrees Celsius to about –5 degrees Celsius, about –15 degrees Celsius to about 0 degrees Celsius, about –15 degrees Celsius to about 5 degrees Celsius, about –15 degrees Celsius to about 6 degrees Celsius, about –6 degrees Celsius to about –5 degrees Celsius, about –6 degrees Celsius to about 0 degrees Celsius, about –6 degrees Celsius to about 5 degrees Celsius, about –6 degrees Celsius to about 6 degrees Celsius, about –5 degrees Celsius to about 0 degrees Celsius, about –5 degrees Celsius to about 5 degrees Celsius, about –5 degrees Celsius to about 6 degrees Celsius, about 0 degrees Celsius to about 5 degrees Celsius, about 0 degrees Celsius to about 6 degrees Celsius, or about 5 degrees Celsius to about 6 degrees Celsius. In some embodiments, the sample of compositions herein are stored at temperature a temperature of about –20 degrees Celsius, about –15 degrees Celsius, about –6 degrees Celsius, about –5 degrees Celsius, about 0 degrees Celsius, about 5 degrees Celsius, or about 6 degrees Celsius. In some embodiments, the sample of compositions herein are stored at temperature a temperature of at most about –15 degrees Celsius, about –6 degrees Celsius, about –5 degrees Celsius, about 0 degrees Celsius, about 5 degrees Celsius, or about 6 degrees Celsius.

In some embodiments, wherein the freezing step is performed after (a). In some embodiments, wherein the freezing step is performed after (b). In some embodiments, wherein the freezing step is performed after (c). In some embodiments, the freezing step is performed after (a), (b), (c), or any combination thereof.

Figure 29:
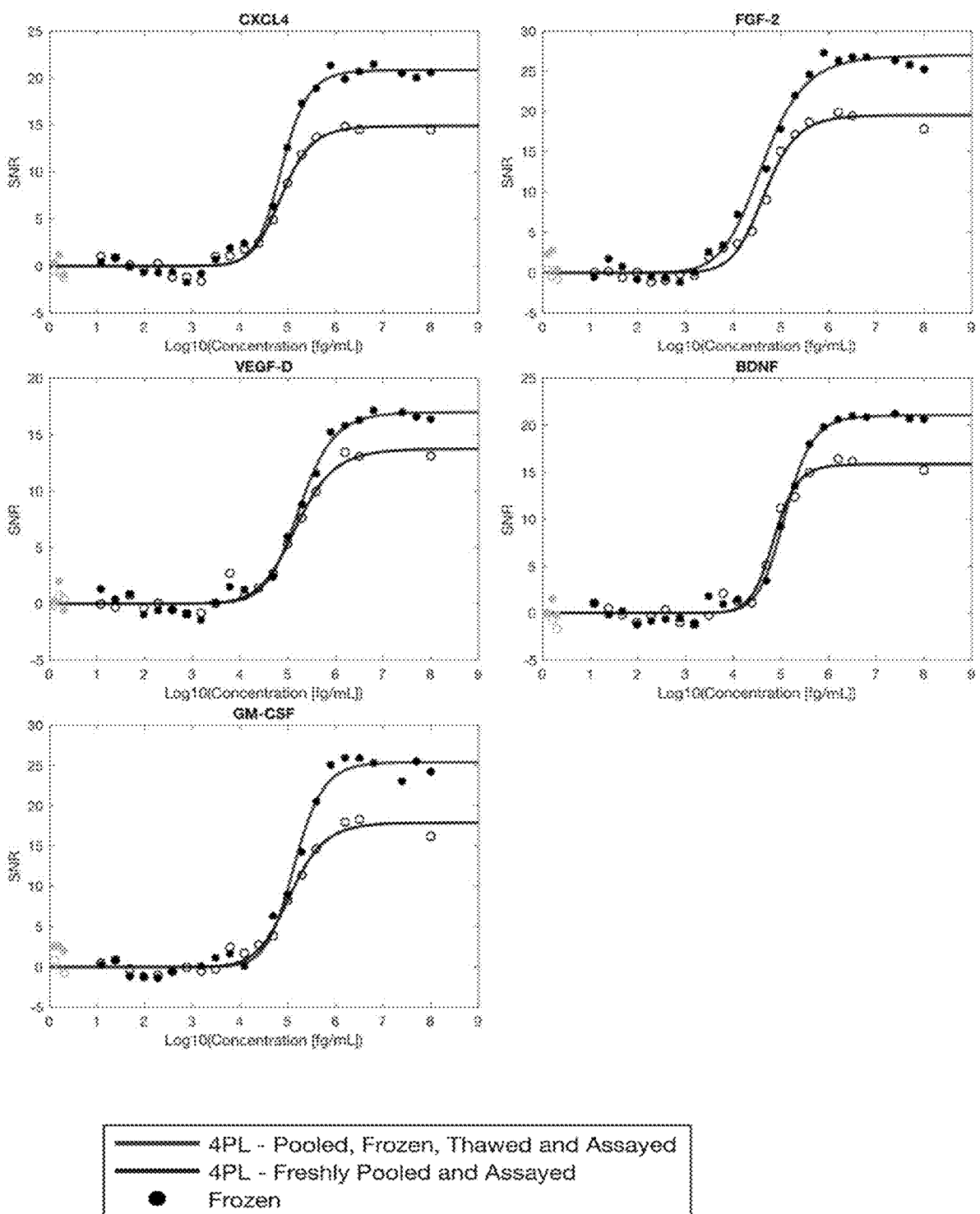
FIG. 29 shows a multiple antigen standard curve comparison between CLAMPs that have been frozen (red curves) for 2 weeks, compared to those that were stored at 4 degrees (blue curves).
Figure 29:
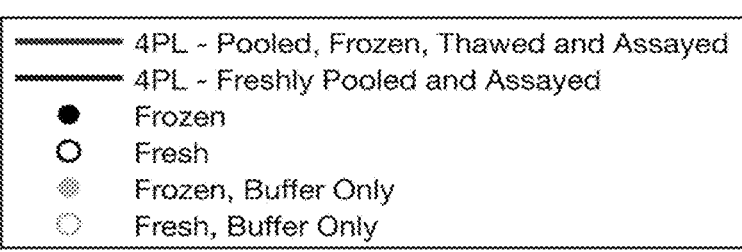
Figure 30:
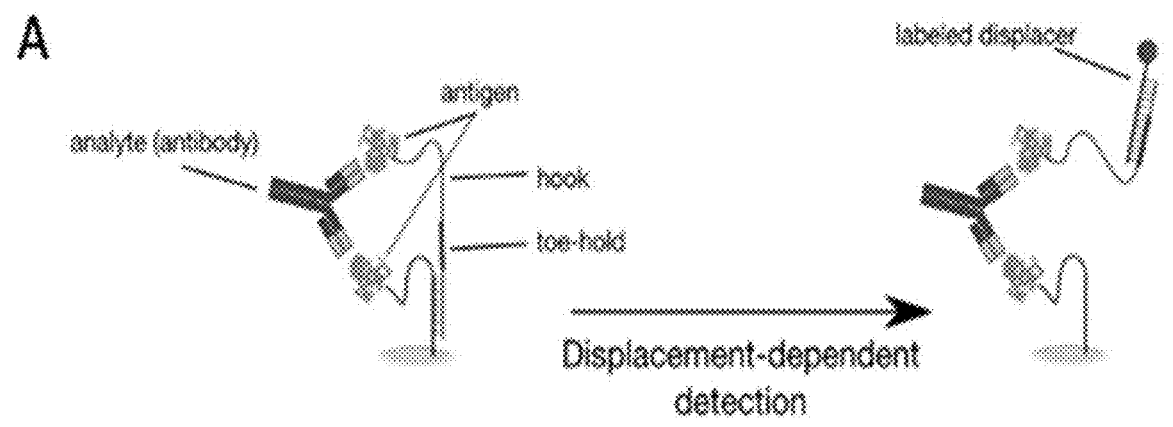
FIG. 30 shows a serological CLAMP against Human Ig specific against SARS-CoV-2 RBD protein. (A) Anti-Ig CLAMP schematic of design and assay workflow. (B) Calibration curve of a dilution series of a reference IgG against RBD protein for two designs with varying surface densities. (B) Measurement of anti-RBD Ig in positive and presume negative control samples.
Figure 30:
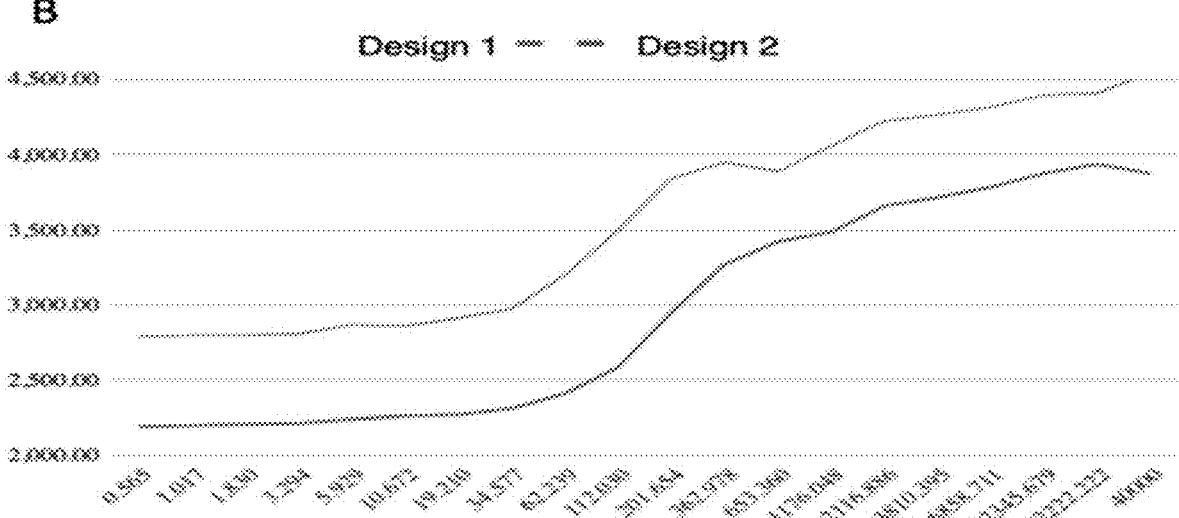
Figure 30:
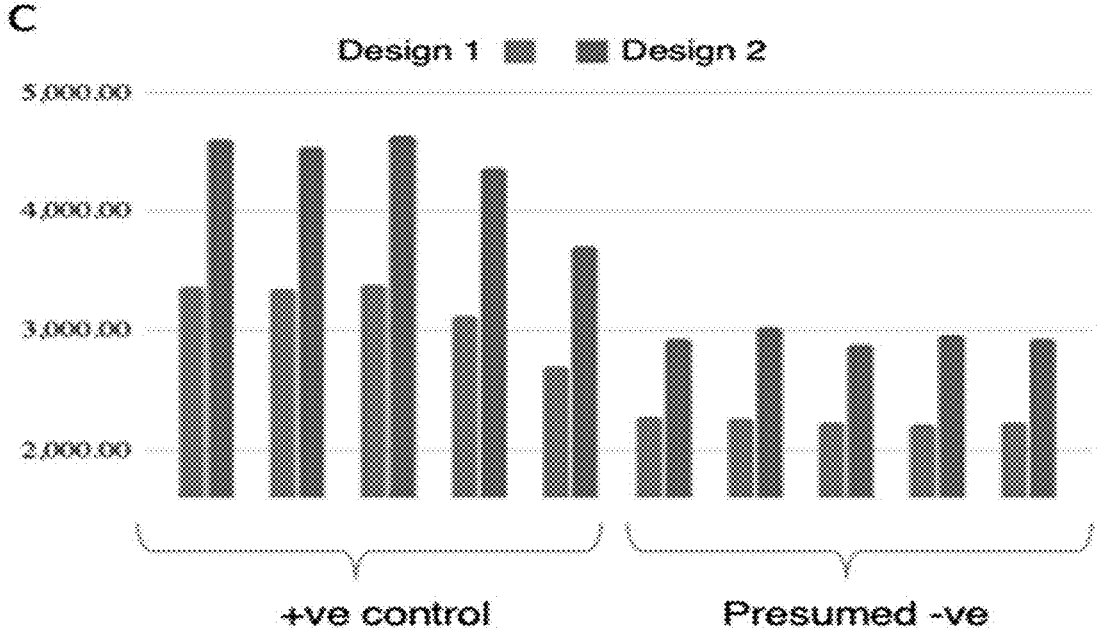
Figure 31:
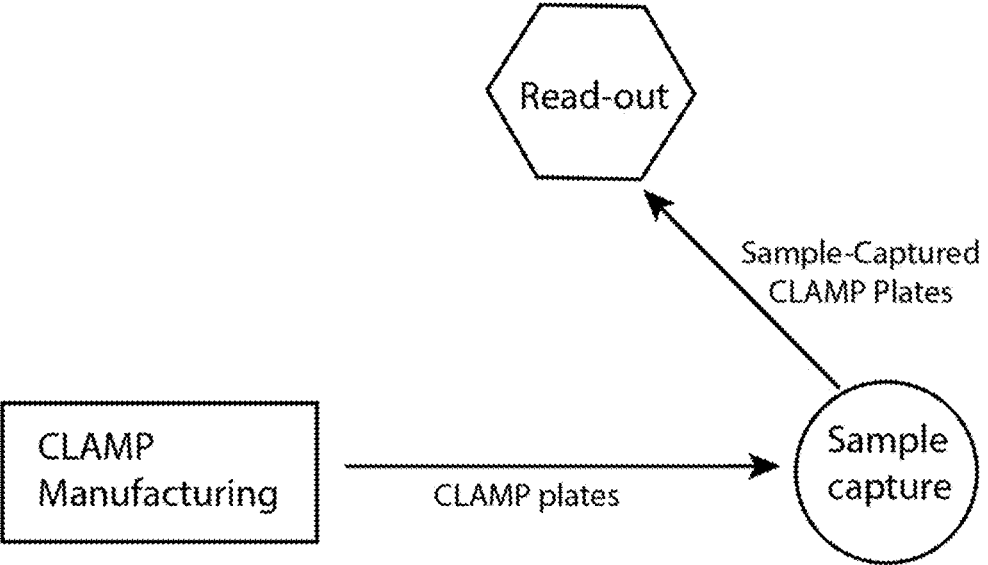
FIG. 31 shows a distributed workflow that allows plate preparation, sample capture, and read-out to be performed at different sites. After manufacturing and plate preparation, CLAMP plates can be frozen, shipped to Sample Capture site, where the sample is mixed with CLAMP pools and stored, either via re-bind method described herein, or via post-capture freezing. Sample-captured CLAMP plates can then be sent, shipped to Read-Out site where data is collected and processed.
Figure 32:
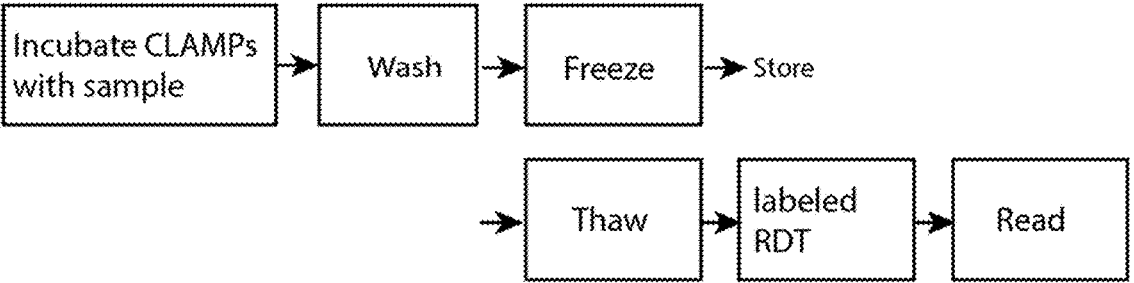
FIG. 32 shows one assay workflow that allows a distributed model based on "Sample-captured CLAMPs" shown in FIG. 31. Here, the CLAMP plates are frozen and stored, shipped, after the sample is incubated and washed with the CLAMPs. Assay completion consists of thawing, labeled-displacement and detection using the RDT method described herein, and read-out.
Figure 33:
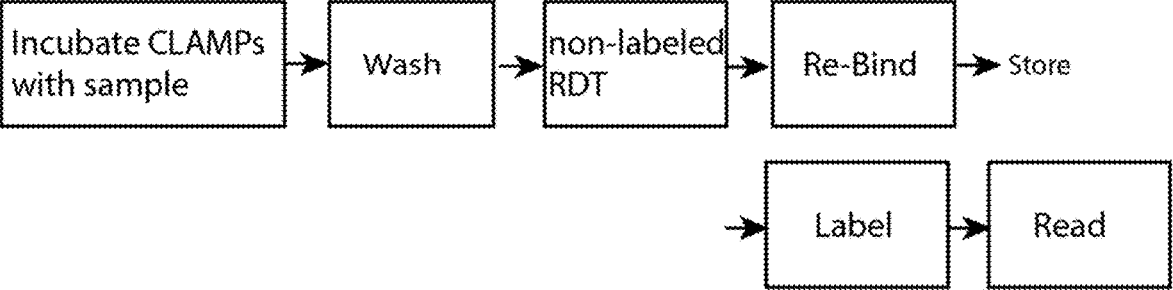
FIG. 33 shows another assay workflow that allows a distributed model based on "Sample-captured CLAMPs" shown in FIG. 31. Here, using the re-bind concept described in this invention, the presence and quantity of the analytes is "recorded" on the CLAMP beads using, for example, stable DNA-hybrids, which stabilizes the signal and allows for storing the now "Sample-Captured CLAMP Plates". In this case, a non-labeled displacer will be used, as described herein.
Figure 34:
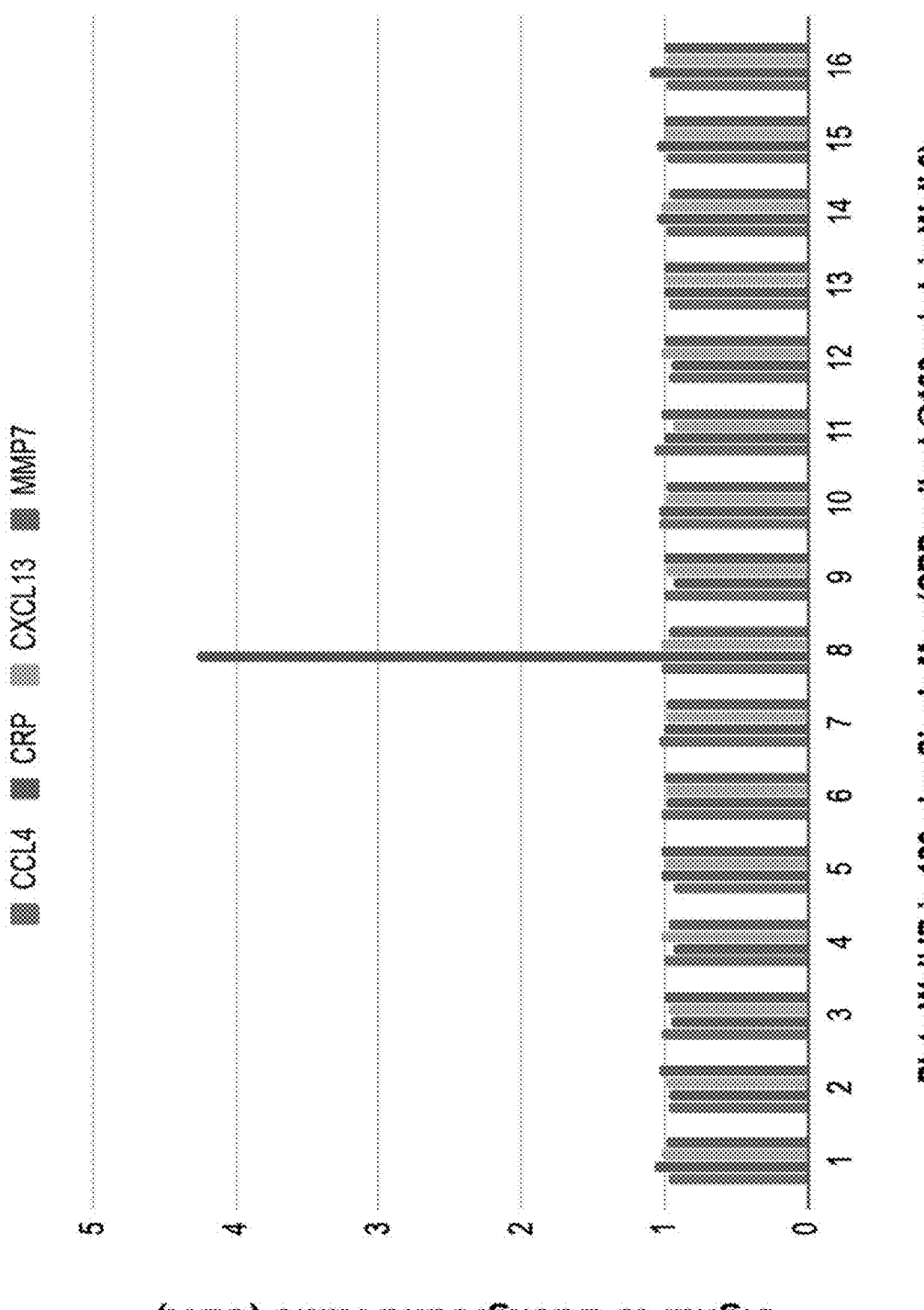
FIG. 34 showing that CLAMPs remain functional if frozen after incubation with sample and wash. Here, single recombinant proteins were spiked into different wells (x axis). After labeled displacement and washing, en lieu of reading the plate immediately, the plate was sealed with a foil cover and stored at −20° C. After 1 week of storage, the plate was thawed on ice for 45 minutes, the beads were resuspended by plate shaking at 950 rpm, and the plate was read by flow cytometry.
Figure 35:
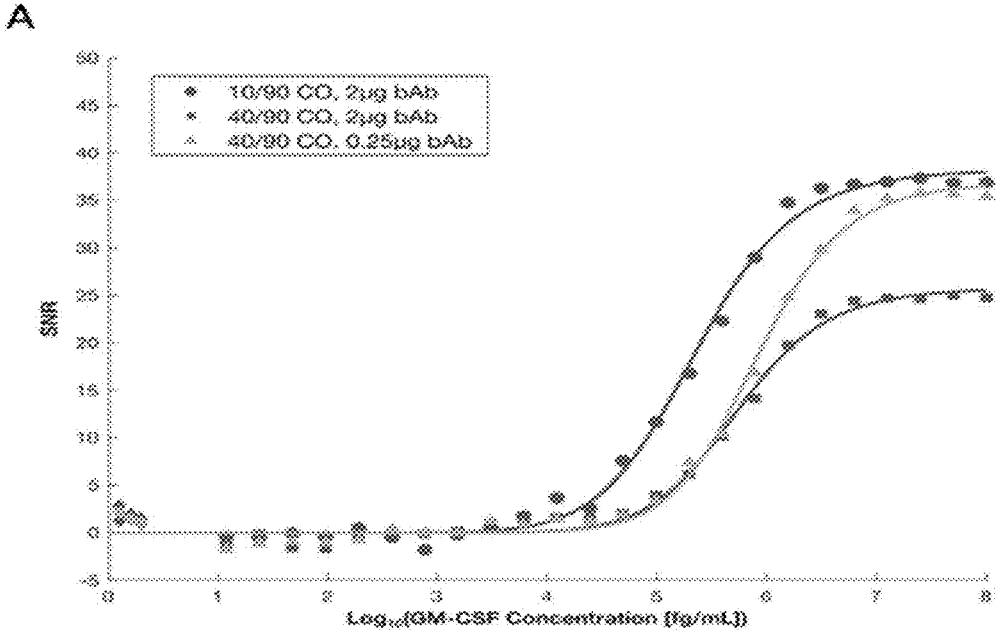
FIG. 35 showing dynamic range modulation and extension for GM-CSF CLAMP using only surface density modification of Capture Oligo (CO) and biotinylated Antibodies (bAb). (A) Standard curve modulation, and (B) effective affinity (Kd) of the standard curve in response to surface density modulation.
Figure 35:
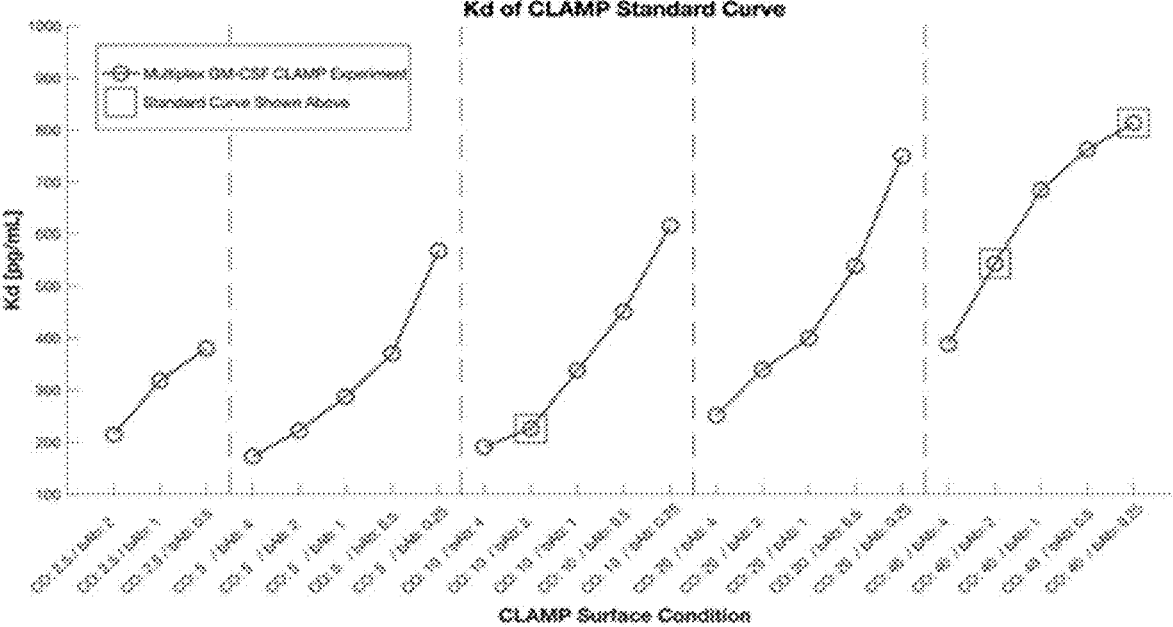

Freezing can increase the ability of a CLA complex to capture an analyte (FIG. 29). In some embodiments, freezing a sample increases the detected signal. In some embodiments, the signal is some embodiments, the signal detected in increased by about 5% to about 50%. In some embodiments, the signal detected in increased by about 5% to about 10%, about 5% to about 15%, about 5% to about 20%, about 5% to about 25%, about 5% to about 50%, about 10% to about 15%, about 10% to about 20%, about 10% to about 25%, about 10% to about 50%, about 15% to about 20%, about 15% to about 25%, about 15% to about 50%, about 20% to about 25%, about 20% to about 50%, or about 25% to about 50%. In some embodiments, the signal detected in increased by about 5%, about 10%, about 15%, about 20%, about 25%, or about 50%. In some embodiments, the signal detected in increased by at least about 5%, about 10%, about 15%, about 20%, or about 25%.

In one embodiment, there is provided a method for the detection or quantification of one or more analytes in a sample, comprising the steps of: (1) at a manufacturing site, preparing a microwell plate at least partially filled with a mixture of barcoded microparticles, (2) storing said microwell plate at freezing temperatures, (3) transporting said microwell plate, using cold chain or other approaches to the test site, (4) thawing the microwell plate, (5) adding in the unknown samples and incubating, (6) freeze the microwell plate, (7) ship the microwell to a read-out site, (8) thaw and perform the labeling and read-out step.

Further provided herein are kits comprising the compositions provided herein. For example, provided is a kit comprising (a) a CLA complex comprising: (i) a support; (ii) a first anchor element attached to the support; (iii) a second anchor element attached to the support; (iv) a capture antibody releasably coupled with the first anchor element, wherein the capture agent is configured to bind the analyte; (v) a detection antibody releasably coupled with the second anchor element, wherein the detection reagent agent is configured to bind the analyte.

In some embodiments, the barcoded microparticles are multiplexed CLAMP reagents and the labeling step is performed via RDT as described in this invention.

Washing steps are essential for performance and sensitivity of sandwich immunoassays but can be, along with mixing steps, a key source of errors and technical variability. Magnetic beads enable highly automated washing and liquid handling procedures to be implemented that allow for more reproducible and high-throughput analyses. However, the implementation by the end-user requires well designed and executed processes and protocols which necessitate intensive validation.

In some embodiments, multiplexed CLAMPs are provided pre-mixed and assembled at appropriate concentrations within 96- or 384-well plates, and provided with a liquid handling instrument to perform all necessary steps for assay handling such as sample-to-bead mixing, washing, and displacer addition, in a semi-automated or fully-automated fashion.

Aside from measurements using a multicolour flow cytometer, some embodiments of CLAMP MPs can be sorted and separated from a mixed solution using a fluorescence-activated cell sorting (FACS) instrument. This enables multiple applications for the CLAMP BMPs, such as, but not limited to, purifying analytes and sorting cell. In one example, magnetic CLAMP MPs used to purify the analytes (such as proteins, oligonucleotides, etc.) for which the CLAMPs have been designed for, from a sample. In such an example, after incubating the magnetic CLAMP BMPs with the samples and subsequent washing steps, the CLAMP BMPs can be separated based on their fluorescent barcodes using FACS. Afterwards the analyte captured from each set of BMPs can be separated from the BMPs. If the analytes are protein, by using an elution buffer (for example a buffer containing 0.1-0.2 M glycine, pH 2.0-3.0), the antibody-antigen bond are weakened and the proteins will be released into the solution. After which the solution can be removed by magnetic aggregation. If the analytes are oligonucleotides, release can be mediated by the a melting reaction, or an additional displacing step.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

Example 1. One-Pot Bead Barcoding and CLAMP Manufacturing

In some embodiments, the multiplexed assay system was implemented on spectrally-encoded beads, wherein a one-pot bead barcoding strategy and automated decoding method can be used in methods and systems provided herein. Examples of such barcoding/decoding methods are described in U.S. patent application Ser. No. 16/153,071 and in Dagher, M. et al., Nature Nanotechnology, vol. 13, pp.

925-932, 2018, the contents of each of which are incorporated by reference herein in their entirety. Such methods use accurate models of fluorophore spectral overlap and multicolor Forster-resonance energy transfer (FRET). For example, such strategies may have a capacity for more than 580 barcodes using two lasers for barcoding and a third laser for assay readout (shown in FIG. 3A). Cytometers with infrared lasers can potentially expand the capacity to more than 5,000 barcodes.

The same manufacturing workflows were used to build a version of a colocalized antibody assay as described herein. Namely, in a first step, streptavidin beads were co-coupled with biotinylated capture antibodies and biotinylated anchor or capture oligos modified with different dyes to yield a distinguishable barcode. Each barcode, and target-specific antibody, were fabricated in separate tubes. In a second step, the detection antibodies (monoclonal) conjugated to a hook oligo were added to the corresponding functionalized beads from the first step. The hook strand oligo was complementary to the anchor strand oligo and hybridized to it, resulting in the assembly and colocalization of matched antibody pairs. The beads can be separately stored for use at a later time.

Figure 3:
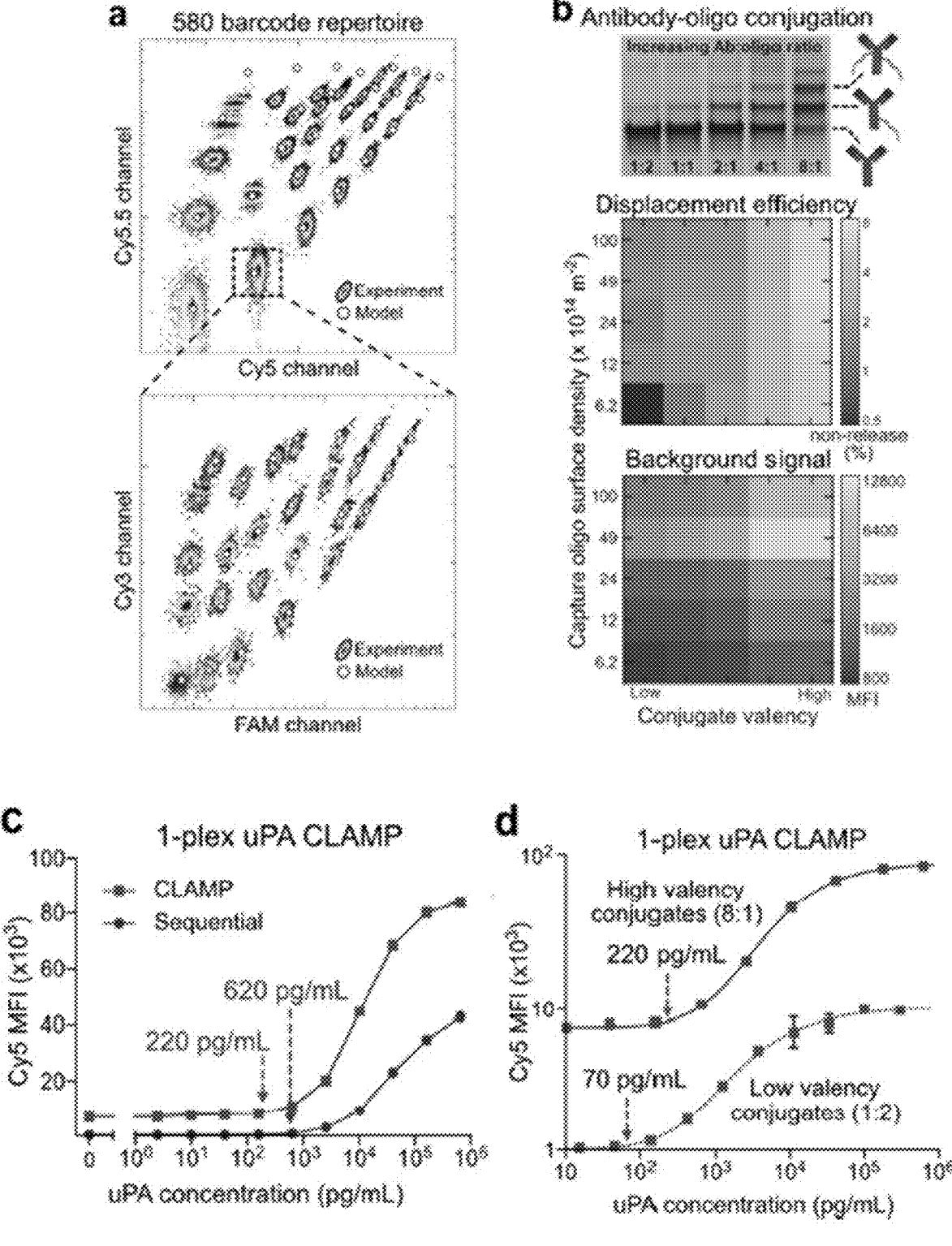
FIG. 3 shows a CLAMP assay in accordance with one embodiment of the technology, in which (a) shows an automated 4-color barcoding strategy, which permits >580 bead barcodes to be implemented on any multicolor cytometer; (b) shows low valency antibody-oligo conjugates dramatically improved strand displacement efficiency (>99%) and minimized assay background signals; (c) shows a 1-plex CLAMP for uPA led to increased sensitivity over a traditional (sequential) immunoassay on beads; (d) shows low valency conjugates improved CLAMP sensitivity further; (e) shows 5-plex CLAMP, assembled with antibody pairs that cross-react extensively in a traditional sandwich format, exhibited no cross-reactivity; and (f) shows individual standard curves for 5-plex CLAMP.
Figure 3:
Figure 3:
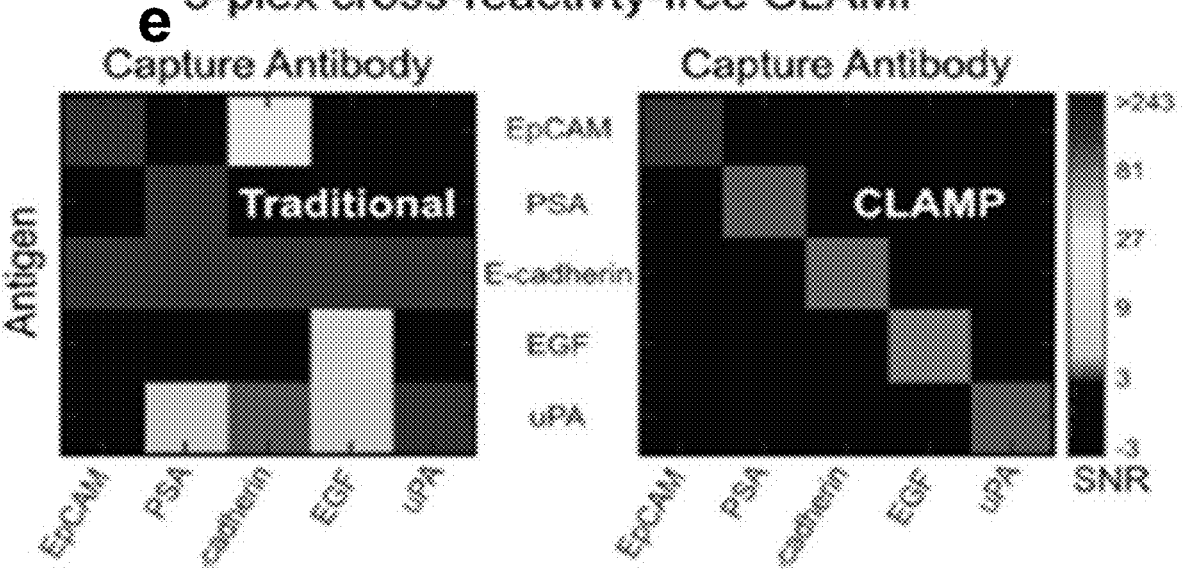
Figure 3:
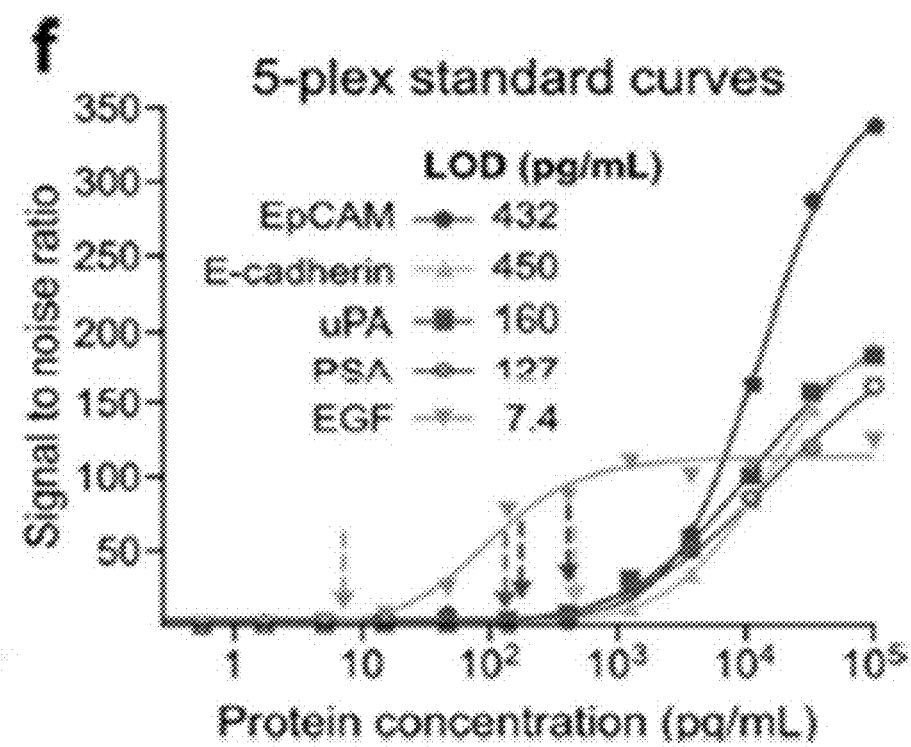

In some embodiments, a low oligo:antibody conjugation ratio or valency and/or two-step purification can be used to optimize (i.e., lower) background signal. For example, low valency antibody-oligo conjugates were shown to maximize CLAMP strand displacement efficiency and minimize background signal (FIG. 3B). After a first optimization round (varying ionic strength, washing and incubation times, nanoscale designs and reagent concentrations) the sensitivity of a 1-plex CLAMP for uPA was improved 3-fold over a traditional sandwich assay (FIG. 3C). Implementing monovalent, rather than high-valency, conjugates resulted in a further 3-fold improvement (FIG. 3D).

In one embodiment, a CLAMP system as described herein comprises the following components:

1) microparticles holding all the other components in place;
2) a type of capture antibodies (cAb) covalently coupled to the microparticle;
3) a type of detection antibodies (dAb) covalently linked to a hook oligonucleotide wherein the detection antibody recognizes the same antigen but not the same epitope as the cAb;
4) an anchor oligonucleotide (AO) linked to the microparticles via a streptavidin/biotin interaction, for example;
5) a stem oligonucleotide (SO) that is fully or partially complementary to the AO and thus renders it at least partially double-stranded;
6) a hook oligonucleotide (HO) covalently-linked to the cAb and partially complementary to the anchor oligonucleotide thus attaching the cAb to the microparticle; and
7) a displacement oligonucleotide (DO) having 2 functions:
   a) containing a fluorescent label and
   b) having a sequence complementary to the HO and overlapping with the sequence of the AO so that the dAb is released from the AO and thus released from the microparticle.

A 5-plex CLAMP using antibodies was assembled wherein the antibodies were highly cross-reactive in a conventional sandwich immunoassay, and confirmed that CLAMP completely avoided cross-reactivity (FIG. 3E). Standard curves for a 5-plex CLAMP are shown in FIG. 3F.

CLAMP was used to profile human serum. Conjugated antibodies and barcoded beads were independently stored for >1 month, and CLAMP yielded good spike-in recovery of PSA in serum (data not shown).

In an embodiment, the CLAMP system described herein is a 10-plex cytokine panel. Cytokines encompassed herein are for example, but not limited to IL1 to IL17, MCP1/3, TNF, EGF/R, and/or VEGF/R. In another embodiment, the CLAMP system encompassed herein is a 10-plex panel focused on breast cancer metastasis, targeting for example, but not limited to, HER2, CEA, p53 and/or CA15-3.

Example 2. CLAMP Assay Architecture

We prepared and tested a colocalization-by-linkage assay on microparticles (MPs) called "CLAMP", in accordance with one embodiment. CLAMP is a multiplexed assay designed to eliminate reagent-driven cross reactivity ("rCR") by colocalizing and confining each antibody pair onto a set of barcoded MPs, thereby avoiding interaction between non-cognate antibodies (FIG. 14C). Oligonucleotides (oligos) are used as programmable building blocks to implement the key molecular 'operations' of CLAMP, including (i) flexible linkage of detection antibodies (dAbs), (ii) on-demand release of dAbs, (iii) transduction of assay signals, as well as (iv) fluorescent barcoding of MPs. Here we detail the conceptual operation and experimental validation and optimization of a CLAMP assay and showcase its efficacy to eliminate rCR using reagents that otherwise strongly cross-react in a conventional MSA.

Figure 14:
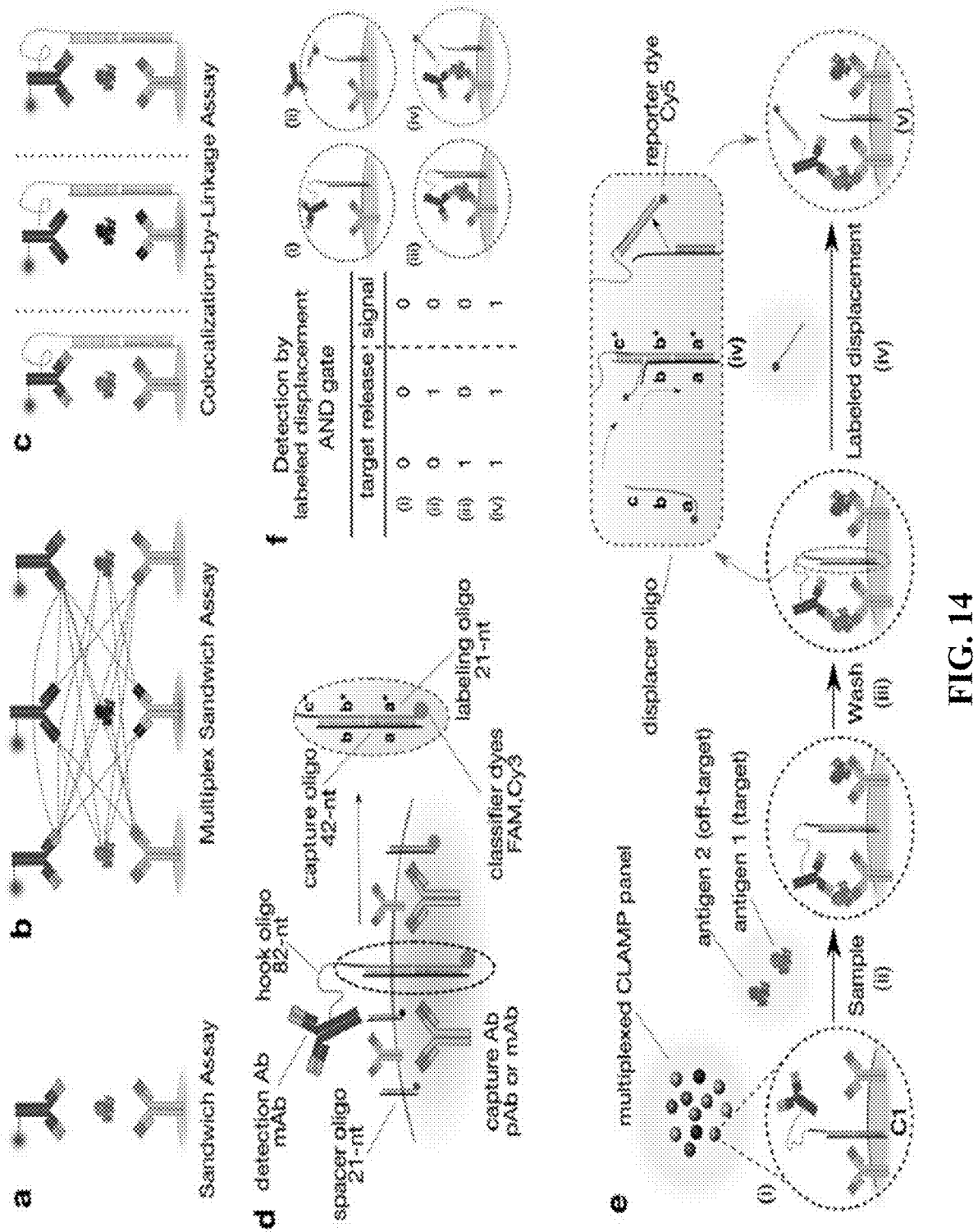
FIG. 14 shows a schematic illustration of single-plex and multiplex sandwich assays, and a CLA system on microparticles ("CLAMP"), in accordance with certain embodiments. (a) Single-plex sandwich immunoassay (also known as ELISA), comprising a pair of matched antibodies. (b) MSA with mixing of antibodies is exposed to a large number of interactions between non-matched antibodies and proteins, often resulting in rCR and false-positives. (c) CLAMP with pre-colocalization of antibody pairs using DNA linkage permitting sandwich binding while eliminating interaction between non-cognate antibodies. (d) The dAb is bound to a hook oligo (HO) that is tethered to the surface via partial hybridization with a capture oligo (CO) strand. A spacer oligo (SO) is used to control the density of the COs and dAb-HOs on the surface (see FIG. 19). (e) A multiplexed CLAMP assay is carried out by (i) mixing barcoded CLAMP microparticle against different targets, (ii) incubating the biological sample with microparticles generating sandwich binding in the presence of the target analyte only, (iii) washing, and (iv) displacing and labeling HOs using a fluorescently-labeled displacer oligo (DO) via toe-hold mediated displacement (inset), leading to (v) labeling of the sandwich complexes that remain on surface. (f) An AND (Boolean) logic gate representation of the detection by labeled-displacement step, where detection at the single-molecule level requires both the capture of target and successful HO release.

The architecture and operative principle of one embodiment, referred to herein as a CLAMP assay, are illustrated schematically in panels d and e of FIG. 14, respectively. To colocalize each pair of antibodies, an 82-nt hook strand oligonucleotide (referred to as hook oligo, or "HO") is covalently bound to a detection reagent which is an antibody, called a detection antibody or "dAb", and is partially hybridized via a 21-bp hybrid to a capture strand oligonucleotide, called a capture oligo ("CO") bound to the surface of a capture reagent which is an antibody, called a capture antibody ("cAb")-coated microparticle ("MP"). Whereas the cAb is immobile on the surface, the dAb is flexible due to the HO's 61-nt single-stranded domain; this flexibility allows formation of a tertiary complex with the analyte (FIG. 14E). The confinement of antibody pairs precludes interaction between non-matched antibodies and restores the singleplex assay configuration on every MP, ensuring that single cross-reacting events (e.g. a target analyte reacting to a non-cognate cAb) do not lead to sandwich binding. A priori colocalization of antibodies allows for rapid dual-recognition of proteins but necessitates a concomitant method for signal transduction and generation. One approach would be to first break the HO-CO linkage. For example, via photo-induced or enzymatic cleavage, or toe-hold mediated displacement, then, after washing of the released dAb-HO complexes, label the dAbs remaining on the surface to signal sandwich formation. However, unbroken CO-HO linkages would result in labeling of the corresponding dAbs irrespective of the presence of the target analyte, which consequently increases the background signal. For example, 2% dAb coverage on a 3 μm MP corresponds to 1000-5000 dAbs that, if labeled, could result in a large increase in background signal and significantly impede sensitive detection.

Figure 7:
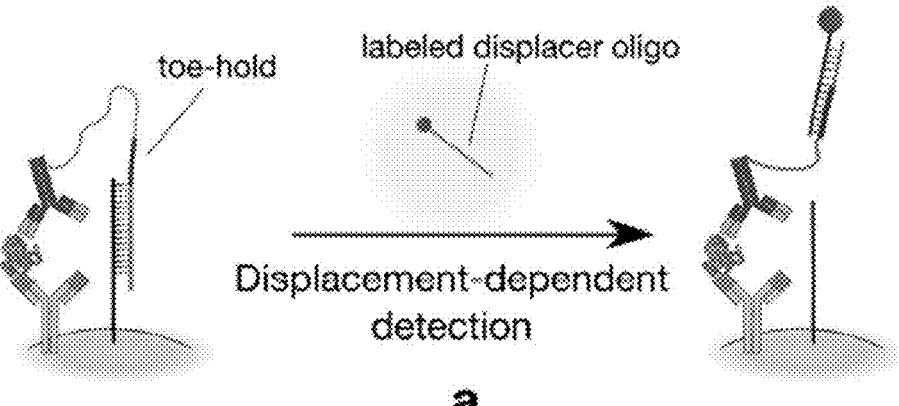
FIG. 7 shows a schematic diagram illustrating an embodiment of displacement-dependent detection. (a) A CLA embodiment is shown, wherein no label is present on the complex, and wherein the analyte is present and bound to both capture and detection ABs in a tertiary complex. A dye-labeled displacer agent, which is an oligo in this embodiment, binds preferentially to the hook strand oligo, simultaneously labeling the hook strand and displacing it from the anchor strand. (b) An AND (Boolean) logic gate representation of the displacement-dependent detection, where detection at the complex-level requires both the bivalent capture of target and successful hook-anchor displacement. Out of the different potential outcomes that consider the analyte presence and displacement success, the scenario shown in (a) is the only scenario that leads to a signal.
Figure 8:
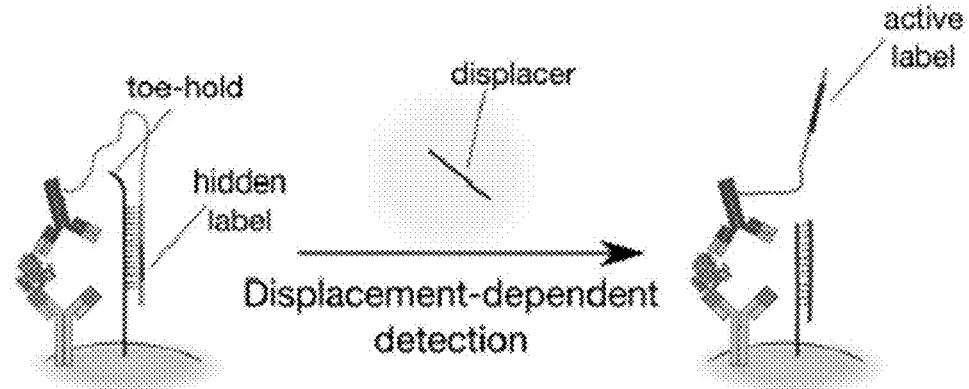
FIG. 8 shows a schematic diagram illustrating an embodiment of displacement-dependent detection wherein the label is a unique DNA sequence that is initially undetectable (i.e., unavailable for binding) because it is masked or hidden by hybridization to the anchor sequence. In the embodiment shown in this figure, the unlabeled displacer agent hybridizes to the anchor's toe-hold sequence to trigger displacement of the hook strand oligo, resulting in the label (unique DNA sequence) being available for subsequent detection, either via secondary hybridization or other DNA detection and/or amplification methods, such as PCR.
Figure 19:
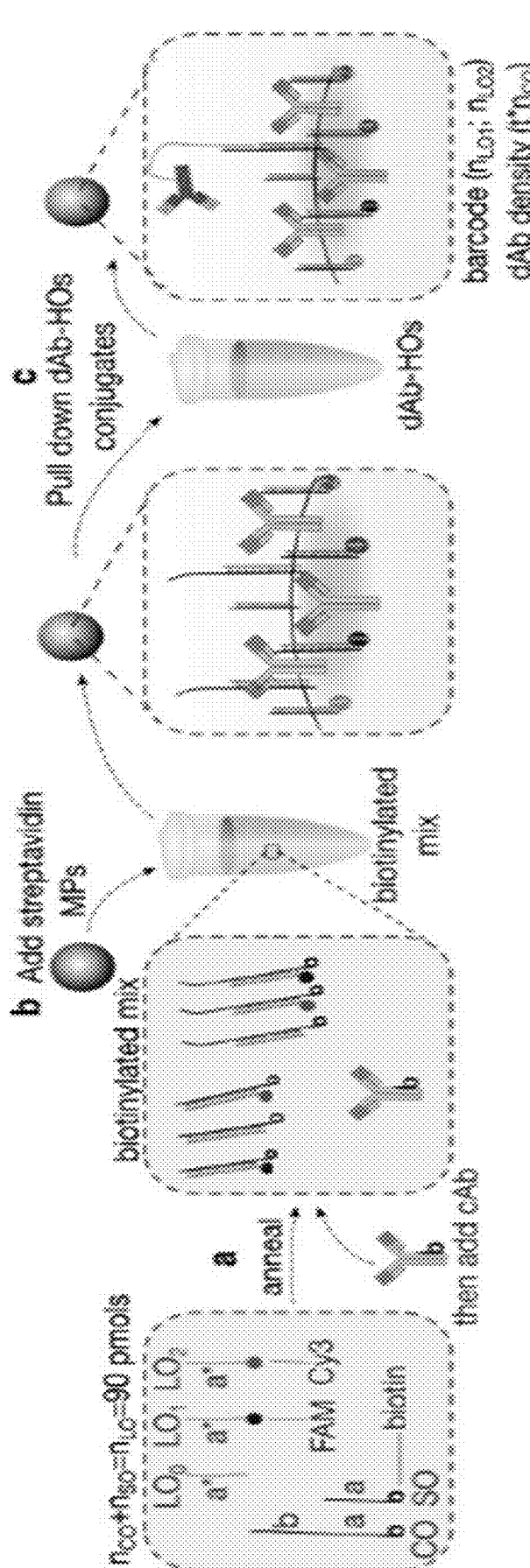
FIG. 19 shows a schematic illustration of synthesis of barcoded CLAMP microparticles, in accordance with one embodiment. Illustration describing the primary steps in the synthesis of the CLAMP microparticles. (a) Oligo constructs are pre-annealed and antibodies are added to form the biotinylated mixture of reagents. The mixture of biotinylated oligos includes precisely controlled proportion of CO/SO totaling 90 pmols and defining the CO (and later dAb-HO) surface density; the biotinylated oligos are annealed to a precisely controlled proportion of $LO_0/LO_1/LO_2$, totaling 90 pmols and defining the barcode. (b) Thereafter, streptavidin MPs are added to the biotinylated mix to proportionally and stochastically label them with reagents on the surface of the microparticles, wherein the relative densities of the oligo components (e.g. $LO_1/LO_2$) is conserved on the surface. (c) The dAb-HOs are finally pulled down on the surface to complete the synthesis of CLAMPs. The dAb density on the surface is proportional to the CO density, and hence, $n_{CO}$.
Figure 20:
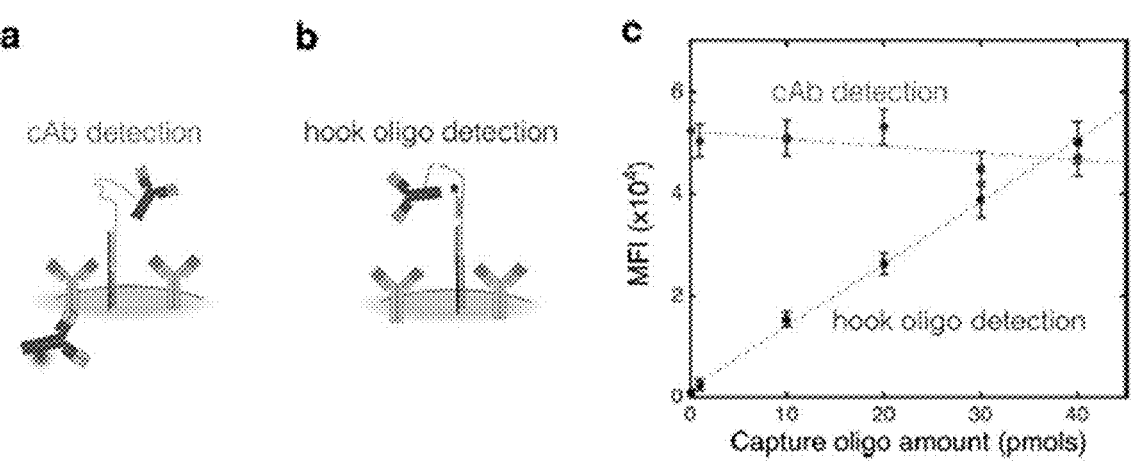
FIG. 20 shows a schematic illustration showing fine-tuning and accurate control of surface densities. (a) cAb detection using anti-goat antibody labeled with AF-647. (b) HO detection using a complementary, but non-displacing, oligo labeled with Cy5. Fluorescent intensities of CLAMP microparticles with varying CO reaction amounts, labeled using AF647 x-goat secondary antibody (red) and cy5-labeled oligos targeting the HOs (non-displacing, blue dots). (c) cAb and HO detection (in red and blue, respectively) for CLAMP prepared with increasing amounts of starting CO and decreasing SO such that $n_{CO}+n_{SO}=90$ pmols. Linear fits to the data are shown in dashed lines, and the error bars plot the standard deviation of the MP fluorescence.

To mitigate this effect in CLAMP assays, we designed a detection scheme to exclusively label 'successfully' released conjugates through the use of a fluorescently-labeled displacer oligo (DO) that binds to a toe-hold domain on HO, displacing and labeling it simultaneously (FIG. 14E, FIG. 7). Importantly, this 'detection-by-displacement' operates as an AND logical gate, requiring both protein dual-capture and dAb release for a detectable signal (FIG. 14F). In this embodiment, CLAMP reagents are assembled on magnetic MPs in two steps, benefitting from the affinity of biotin-streptavidin bond and Watson-Crick base pairing (FIG. 18). In a first step, a mixture of biotinylated oligos and antibodies are co-immobilized to the surface of streptavidin-coated MPs. The one-pot nature of the labeling affords accurate control over the CO surface density (FIG. 19), and simultaneously allows MP-encoding via one-pot labeling with multicolour classifier dyes, as described elsewhere (Dagher, M., et al., Nature Nanotechnology, vol. 13, pp. 925-932, 2018). In a second step, dAb-HO complexes are pulled-down via HO-CO hybridization to complete the assembly of CLAMPs.

Example 3. CLAMP Assay Optimization

We first optimized the efficiency of the toe-hold mediated displacement reaction by displacing unconjugated, Cy5-labeled HOs (FIG. 15). HOs were pulled down on MPs with different CO densities, then released using unlabeled DOs. Increased ionic strengths in the displacement buffer (MNaCl>500 mM) were helpful for screening the negatively charged oligos and improved the efficacy of DO hybridization to, and release of, the HOs. 98% displacement was reached over a wide range of CO densities with increased ionic strengths and DO concentrations (MNaCl~500 mM and MDO=1 μM, respectively).

Next, we studied the impact of antibody-oligonucleotide conjugates on assay background by measuring the residual signal on the MPs following a labeled-displacement step in buffer (see Methods below). We first conjugated HOs to immunoglobulin-G (IgGs) using a commercial kit (Solulink) leading to approx. 90% antibody conjugation yield and an average of 2 HOs per IgG (i.e., $\lambda$~2). Using these conjugates, the assay background was an order of magnitude greater than the assay background of unconjugated HOs (FIG. 16A). The increase in background signal was due to multivalent HO conjugates, which can result in unreleased dAb-HOs complexes (due to an unbroken HO-CO linkage) that are labeled by hybridization of a DO to at least one of the other HO strands, thereby generating a fluorescent signal in the absence of a sandwich binding with a protein (FIG. 16B). An effective way to minimize multivalent dAb-HO conjugates is to reduce the average conjugation valency; for example, by aiming for $\lambda$ of 0.1, Poisson statistics indicates that <5% dAb would be bound to multiple HOs. The trade-off of such a low conjugation valency is a decreased antibody conjugation yield (10%), which leaves 90% of antibodies unreacted. To avoid wasting unreacted antibodies, we developed a conjugation and purification workflow that maintains the native state of unconjugated antibodies and allows their recycling. The relative concentration of dAb and HO were adjusted and was modulated from 1.25 to 0.1 (FIG. 16C). The dAb-HO conjugates of varying valency were pulled down on MPs with varying CO densities. As expected, lower valency significantly decreased residual assay background, matching the background signal exhibited by unconjugated HOs for 0.1<$\lambda$<0.2 (FIG. 16D), leading to low valency conjugates with fewer than 8% of multivalent conjugates. Consistent with a multivalent scenario, increasing CO density amplified the high background signals for higher valency dAb-HOs.

To optimize assay performance, we modulated the dAb-HO density. In CLAMP, adequate local dAb concentrations are key for sensitive and high capacity sandwich binding which, for a set HO length, is chiefly dependent on the surface densities of dAb-HOs and, through hybridization capture, COs. CLAMPs against urokinase plasminogen activator (anti-uPA CLAMP) with varying CO densities were prepared using low valency dAb-HO conjugates with fewer than 8% multivalent conjugates (FIG. 16D; see Methods below). anti-uPA CLAMPs were incubated with a serial dilution of recombinant uPA antigen, followed by washing and detection by labeled-displacement. As expected, increasing CO densities modulated the signal-to-noise ratio (SNR) of the assay, revealing that a density greater than $10^{14}$ $m^{-2}$ is necessary for adequate SNRs (FIG. 16E). Densities greater than $10^{14}$ $m^{-2}$, on the other hand, provided little improvement in SNR as they also resulted in increased background signal. Lastly, to assess the importance of conjugate valency on assay performance, we compared anti-uPA of high valency ($\lambda$~2, Solulink) against low valency conjugates ($\lambda$~=0.1, FIG. 16F). The lower valency conjugates resulted in significantly lower background signals (10-folds) and, correspondingly, a 3-fold improvement in detection limits (FIG. 16F). On the other hand, low valency conjugates exhibited a decreased dynamic range of the fluorescence as sandwich-bound dAb-HO complexes are predominantly labeled with a single dye. Taken together, these results highlight the importance of conjugation valency on background signals and assay performance in general.

Example 4. Multiplexed CLAMP Assay

Figure 17:
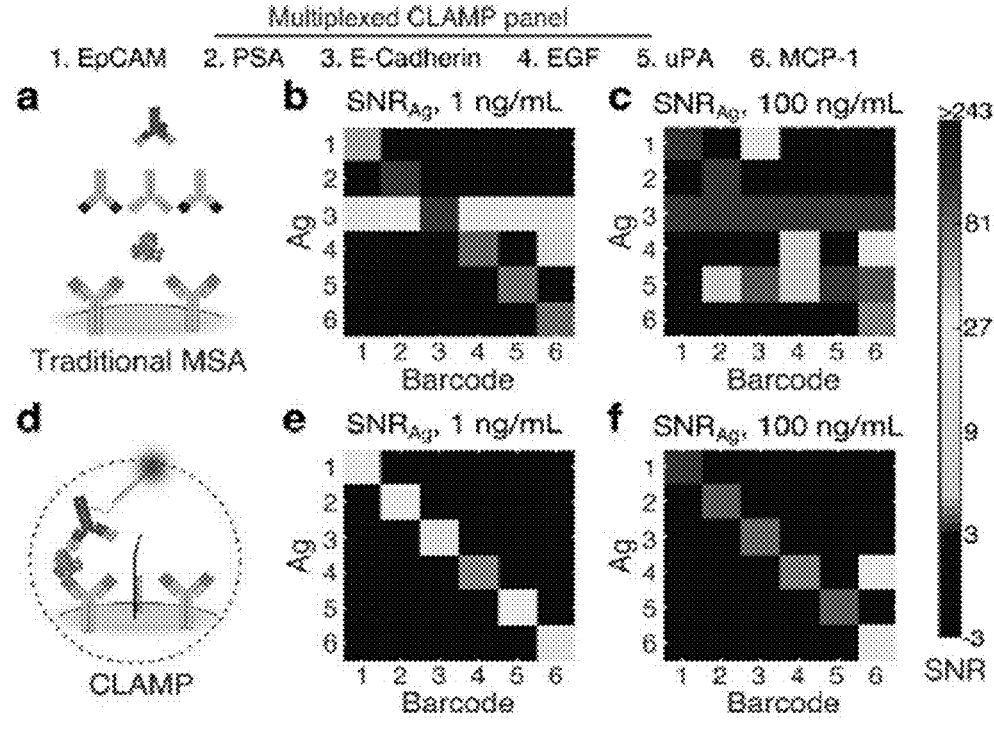
FIG. 17 shows elimination of cross-reactivity (CR) in CLAMP. Schematic representation of the CR screening performed for (a) conventional MSAs and (d) CLAMP assays, wherein the barcoded microparticles are mixed and incubated with one target at a time to reveal CR in a multiplexed format. SNRs quantifying specific (diagonal) and non-specific (off diagonal) assay signals for conventional MSAs (b, c) and CLAMP (e, f) in response to the addition of individual antigens at (b, e) 1 ng/mL and (c, f) 100 ng/mL. (g) Assay MFI of a MCP-1 single-plex sandwich assay with MCP-1 (blue) and EGF (red) spike-ins at the specified concentrations (x-axis). (h) SNR signals of a 5-plex CLAMP dilution series. (inset) SNRs are calculated using barcode-specific backgrounds and global standard-deviations.
Figure 17:
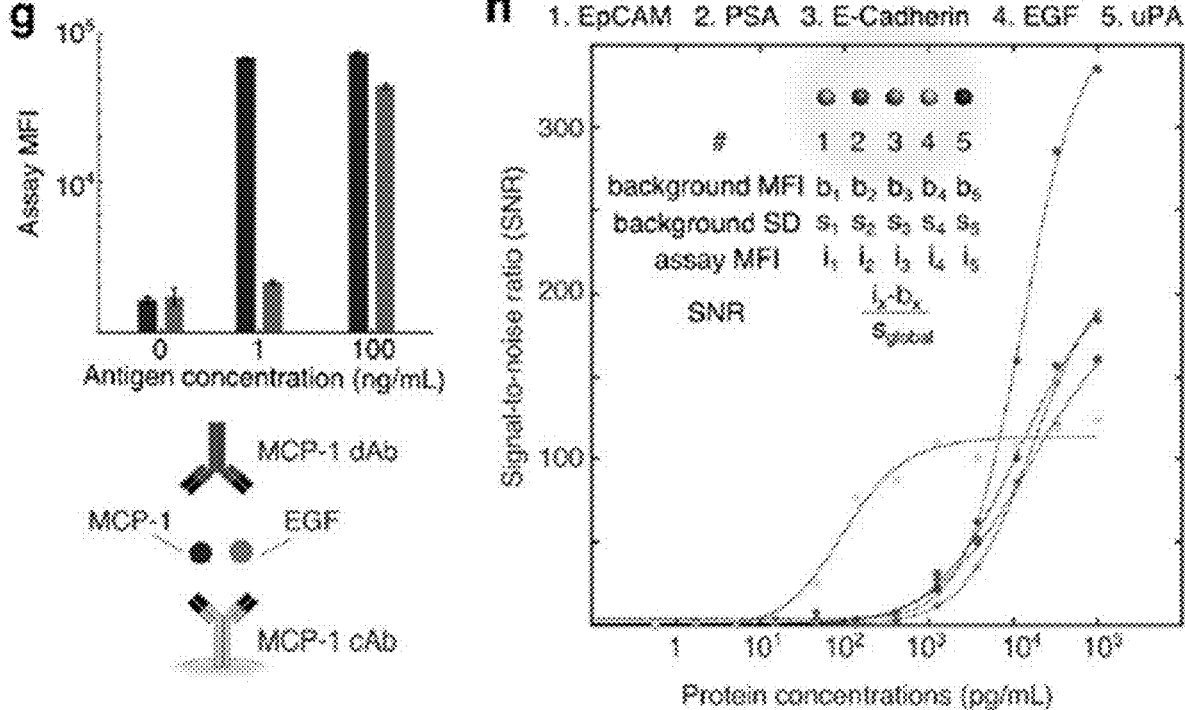

To test CLAMP's efficacy in eliminating reagent-driven cross reactivity ("rCR"), we screened the assay specificity of a multiplexed CLAMP in accordance with one embodiment. In addition, to challenge the CLAMP assay we selected antibody pairs that have been shown to exhibit different types of rCR when used together in a conventional multiplexed sandwich assay ("MSA"). To this end, antibody pairs against six targets (EpCAM, PSA, E-Cadherin, EGF, uPA and MCP) were shortlisted from a 35-protein panel that we previously characterized for specific and non-specific binding in a conventional MSA (Dagher, M. et al., Nature Nanotechnology, vol. 13, pp. 925-932, 2018). For conventional MSAs, the specificity screen consisted of incubating each individual antigen with a pool of cAb-coated barcoded MPs, followed by addition of mixed dAb cocktail and secondary-antibody ("sAb") for detection and labeling, respectively (FIG. 17A). Measuring the fluorescence across the different barcodes in response to an antigen concentration of 1 and 100 ng/mL (FIG. 17B-C) uncovered two types of non-specific binding that generated false-positives, namely indiscriminate sticking of antigens (observed for E-Cadherin and uPA) and cross-reactivity between antigens and antibodies. On the other hand, the specificity screen for CLAMP assays was performed by incubating a single antigen at-a-time with multiplexed CLAMPs and running the detection by labeled-displacement (FIG. 17*d-f*; see Methods below). All but one of the non-specific signals detected in conventional MSAs were completely eliminated using CLAMP assays. For example, the pervasive, non-specific binding of E-Cadherin, which led to a signal on all off-target beads in conventional MSAs, was not detectable in CLAMP assays. In contrast, cross-reactivity was detectable between MCP-1 antibodies and EGF antigen at 100 ng/mL both in conventional MSA as well as CLAMP. To investigate the source of this false-positive signal, we performed single-plex assays using MCP-1 antibodies only, separately spiking MCP-1 or EGF at 1 or 100 ng/mL (FIG. 17G). The detection of EGF by MCP-1 antibodies in single-plex indicated a dCR. Indeed, this dCR cannot be mitigated by CLAMP nor ELISA, and is an of poor affinity binders. Overall, these results showcase the strength of CLAMP in eliminating rCR in a multiplexed assay, as well as identifying dCR in multiplexed, combinatorial fashion. Finally, dilution curves of the remaining 5 proteins were generated and their SNRs were plotted as shown in FIG. 17H.

In summary, we successfully demonstrated use of CLAMP, a homogeneous MSA that uses oligonucleotides to precolocalized antibody pairs on MPs. By confining each antibody pair to their respective MPs during sample incubation, CLAMP can be multiplexed while maintaining single-plex assay environments on each MP and, in doing so, eliminates reagent-driven CR. Notably, the pre-colocalization of antibodies in CLAMP represents a departure from conventional sandwich immunoassays, where matched antibodies are separate at the beginning of the assay. To detect correct sandwich binding, we have shown that a labeled displacer oligo can be used to simultaneously release and label dAb-oligo complexes. We studied and demonstrated the importance of using monovalent antibody-oligo conjugates to avoid labeling unreleased complexes and increasing background signals. We have experimentally validated the assay, both in single-plex and multiplex, and screened the specificity of the assay in multiplex using five antibody pairs pre-selected for CR, demonstrating that CLAMP eliminates all rCR experienced in a conventional MSA.

CLAMP can provide several distinct advantages over currently available MSAs. First, CLAMP can be easily deployable as it does not necessitate dedicated equipment for readout or introduce new workflows. Second, CLAMP can be a rapid assay as it can be completed in little over three hours. Finally, by eliminating the need to incubate detection antibodies in solution (which is typically done at high concentrations), CLAMP can provide significant reductions in reagent consumption. Owing to its highly scalable and highly efficient nature, CLAMP can be used to provide a truly-scalable multiplexed ELISA platform that meets the increasing demands in biomarker discovery and drug development.

Example 6. Low Antibody Concentration Minimizes Cross-Reactivity in a CLAMP Assay Conventional multiplexed sandwich immunoassays are commonly conducted with a mixture of reagents in the solution phase. In particular, the detection antibodies (dAbs) against different targets are mixed and applied to the reaction together. The application of such dAb cocktail leads to spurious binding and generates false-positive signals from non-specific binding events (between a cAb or dAb and a non-targeted analyte) that are difficult to discriminate from the real target protein-binding signal. The risk of reagent-driven CR scales as $\sim 4N^2$ with the number of target analyte N.

In contrast, in embodiments of CLAMP, reagent (e.g., antibody) pairs can be pre-assembled and colocalized on barcoded microparticles to avoid the reagents mixing. The detection antibodies (dAbs) will only be released in solution after the displacement reaction, as described herein. In some embodiments, to avoid re-binding on off-target beads after the displacement reaction, the dAbs released into solution should optimally remain at sufficiently low concentrations.

Figure 16:
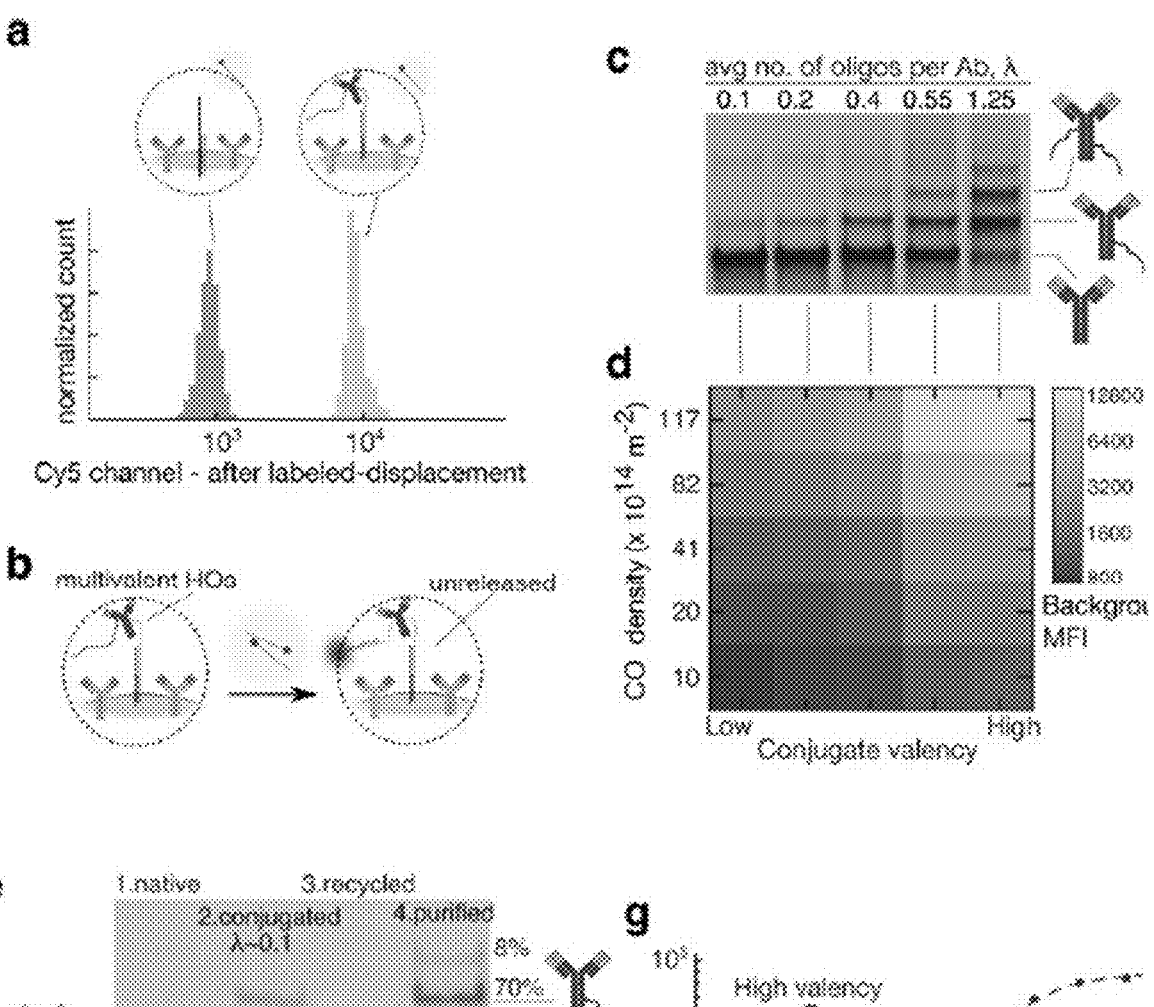
FIG. 16 shows CLAMP optimization by modulating conjugate valency and surface density. (a) Normalized histograms compare the CLAMP background signal (i.e. residual signal after incubation with Cy5-labeled DO) for microparticles without HOs (in blue) and with multivalent dAb-HOs conjugates (in yellow) (see FIG. 6). (b) Illustration depicting how multivalent dAb-HO conjugates may increase background signal by labeling unsuccessfully displaced dAb-HO complexes despite the absence of sandwich binding with the target analyte. (c) SDS-PAGE of mouse anti-goat IgGs conjugated with HOs with increasing valencies and stained by silver amplification. (d) Assay background MFI plotted with respect to increasing conjugate valency (columns) and increasing CO density (rows). (e) SDS-PAGE of low valency dAb-HO (mouse uPA mAbs) conjugates at different stages of the purification protocol where (1) native dAb, (2) conjugation product dAb-HO (non-purified), (3) recycled (non-conjugated) dAb, and (4) purified dAb-HO. (f) MFI assay values for x-uPA CLAMP assays against standard dilutions of uPA antigen and for varying CO densities. Error bars are standard-deviation of the microparticle signals in Cy5 channel. (g) MFI signals in x-uPA CLAMP assays using low (blue dots) and high (red dots) valency conjugates. Error bars are standard deviations of MFI signals across wells (n=3). The LODs shown on each curve are calculated as discussed in Methods below.

FIG. 16 plots the dAb concentration profile with respect to the starting amount (y-axis) and volume of solution during the displacement step. The typical dAb concentration in a conventional ELISA is ~1 μg/mL (67 nM), and with sufficiently-long incubation, binding can still occur when the dAbs are as low as 1 nM (such as in a Simoa assay by Quanterix).

Figure 22:
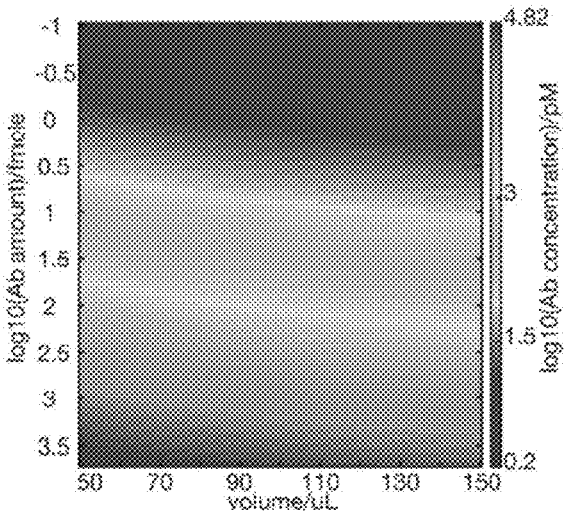
FIG. 22 shows a calculation of the displaced detection antibody concentration profile for a CLAMP assay in accordance with one embodiment, where the detection antibody concentration profile is plotted with respect to the starting amount (y-axis) and the volume of solution (x-axis) during the displacement step.

To ensure that off-binding is avoided after release, the amount of antibodies per target should ideally be kept <10 pM. In a volume of 100 uL, the amount of antibodies is <1 fmoles. In a CLAMP assay, in some embodiments, the amount of released Ab from 1000 microparticles was estimated to be 0.1-1 fmoles (FIG. 22). The numbers indicate that the dAb concentration released from the CLAMP system was significantly lower compared to other methods where free diffusion-based reagent mixing is required.

Example 7. Displacement-Dependent Signal Transduction Minimizes Background Signal in a CLAMP Assay In an embodiment of a CLAMP colocalized assay where both antibodies are precolocalized on the support, signal transduction could be performed by detecting all dABs remaining on the surface after release and washing. However, any non-released hook oligo-dAb complexes could result in an analyte-independent signal, significantly contributing to the background noise. Hence, it will be appreciated that to avoid increasing the background signal, in some embodiments a near-complete anchor-hook displacement and washing of hook oligo-dAB complexes are required.

In some embodiments, the problem of increased background signal due to inefficient release can be addressed through a displacement-dependent signal transduction mechanism. Such a mechanism would ensure that only displaced hook-anchor strands are detectable, and as such, non-displaced strands, which might occur due to inefficient displacement, do not yield a background signal. In such embodiments, signal transduction at the molecular level only occurs if both of the following conditions are satisfied: (i) formation of a tertiary complex, and (ii) displacement of the hook-anchor strands.

In some embodiments, therefore, the detection Ab and the hook strand are not labeled, and displacement occurs using a labeled (e.g., fluorescently-labeled) displacer oligo. In this embodiment, the displacer oligo can bind to the hook strand preferentially which (i) releases it from the anchor strand and (ii) labels it. On the other hand, a non-displaced hook oligo is not labeled and does not contribute to the signal. This mechanism is equivalent to an AND gate where the signal (output) is dependent on both displacement (input 1) and analyte presence (input 2), as shown in FIG. 23.

To demonstrate the effectiveness of the displacement-dependent signal transduction, we performed calibration assays for IL-7, IFN-gamma, and MMP-9. In a first test, the displacer oligos were not labeled, and the mouse-dAbs were targeted using anti-mouse BV421 secondary antibody. The BV421-labelled secondary antibody was targeting at the dAb independent of whether it was released and hence the labelling occurred regardless of the displacement. In a second test, the displacement oligo was labeled using Cy5, which tested the displacement-dependent signal transduction. As shown in the logic gate representation chart (FIG. 23), the BV421 signal would be introduced in condition (i), (iii), (iv), but the Cy5 signal would only appear in condition (iv). Example calibration curves from the targets obtained by using the two labeling methods is shown in FIG. 24. The signal background from BV421 was significantly higher compared to the Cy5 signal, while the assay performance in terms of sensitivity and dynamic range were improved with the labeled-displacement (Cy5).

Example 8. Low Valency Antibody-Oligo Minimizes Background Signal in a CLAMP Assay In some embodiments, the hook and anchor strands are DNA oligonucleotides. Antibody-DNA conjugation can be performed, for example, by targeting the lysine groups on an IgG molecule. Heterobifunctional linkers such as sulfosuccinimidyl 4-(N-maleimidomethyl)cyclohexane-1-carboxylate (sulfo-SMCC) can be used to therefore link a thiol-terminated DNA to an IgG molecule. This reaction, however, results a heterogenous conjugates, wherein the number of oligos per antibody is dependent on the stoichiometry of DNA:antibody during the reaction. Multivalent conjugates (more than one oligo per antibody) can reduce displacement efficiency and hence increase the background signal.

Figure 25:
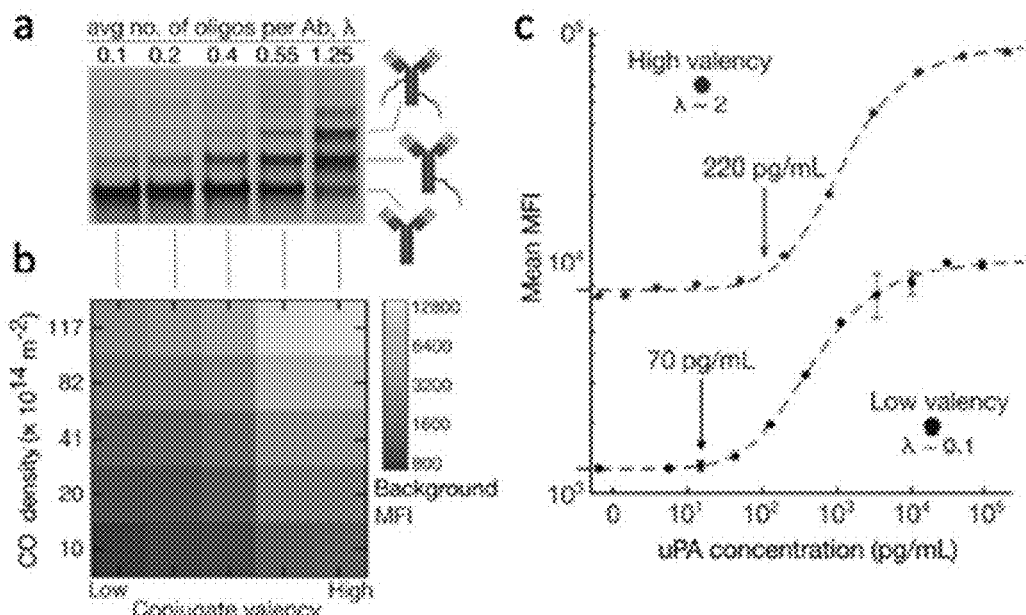
FIG. 25 shows CLAMP optimization by modulating conjugate valency. (a) SDS-PAGE of mouse anti-goat IgGs conjugated with HOs with increasing valencies and stained by silver amplification. (b) Assay background MFI plotted with respect to increasing conjugate valency (columns) and increasing CO density (rows). (c) MFI assay values for x-uPA CLAMP assays against standard dilutions of uPA antigen and for varying CO densities. Error bars are standard-deviation of the microparticle signals in Cy5 channel. (g) MFI signals in x-uPA CLAMP assays using low (blue dots) and high (red dots) valency conjugates. Error bars are standard deviations of MFI signals across wells (n=3). The LODs shown on each curve were calculated as discussed in Methods below.

As shown in FIG. 25A-B, we modulated the binding valency and determined it through SDS-page, and used the resulting conjugates to determine displacement efficiency. High valency conjugates resulted in increased assay background. As expected, a higher anchor strand oligo density resulted in further increase of the background signal. To determine the impact of high conjugate valency on the signal background, we performed a CLA assay using a displacement-dependent detection mechanism (FIG. 25C). High-valency ($\lambda$, avg, no of oligos per antibody~2) and low-valency conjugates ($\lambda$~0.1) were used to generate calibration curves for uPA. Lower valencies resulted in lower background and improved sensitivity by 3-fold.

Example 9. Cross-Reactivity Characterization at 40-Plex

Figure 11:
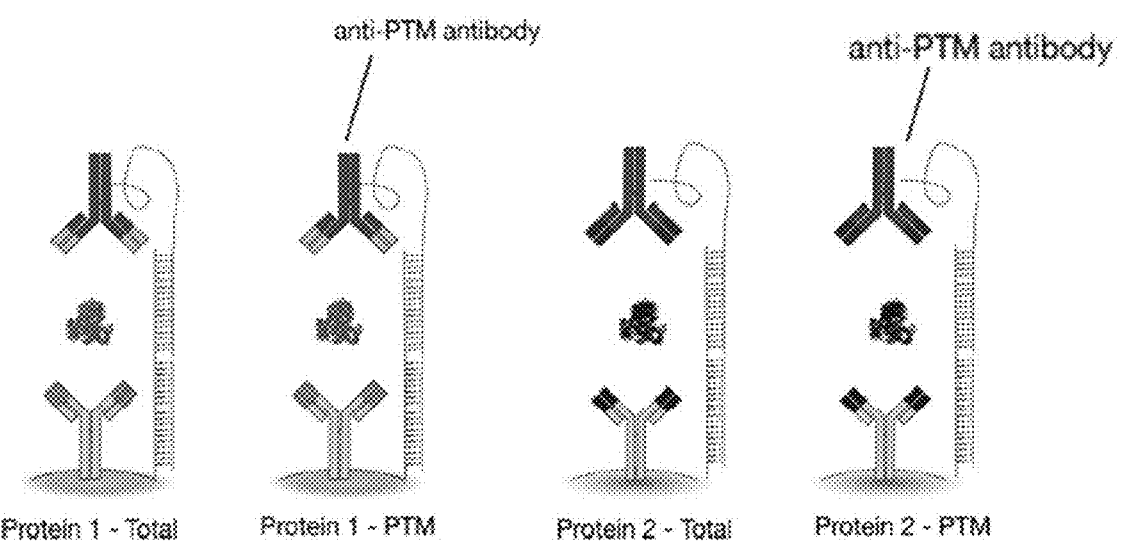
FIG. 11 shows a schematic diagram illustrating an embodiment of CLA used for detection of post-translational modifications (PTM) in multiplex, wherein arrays (planar or beads) are assembled with AB pairs targeting total and PTM-specific protein.
Figure 12:
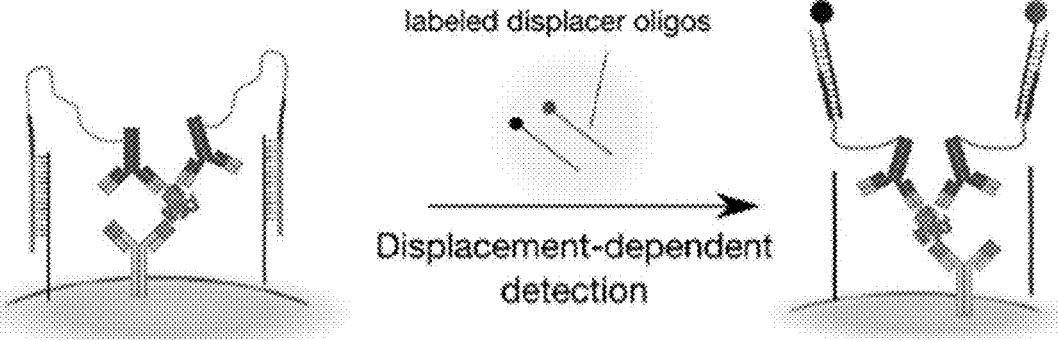
FIG. 12 shows a schematic diagram illustrating an embodiment of CLA where the capture reagent is an antibody attached directly to the support and there are two anchor strands. Each of the two anchor strands is linked by a DNA hybrid to a hook strand linked to a detection reagent (also an antibody). In the presence of analyte, a quaternary complex is formed. The hook strands are released, using labeled displacer agent oligos, from their respective anchor strands. The two labels may be the same or different.
Figure 26:
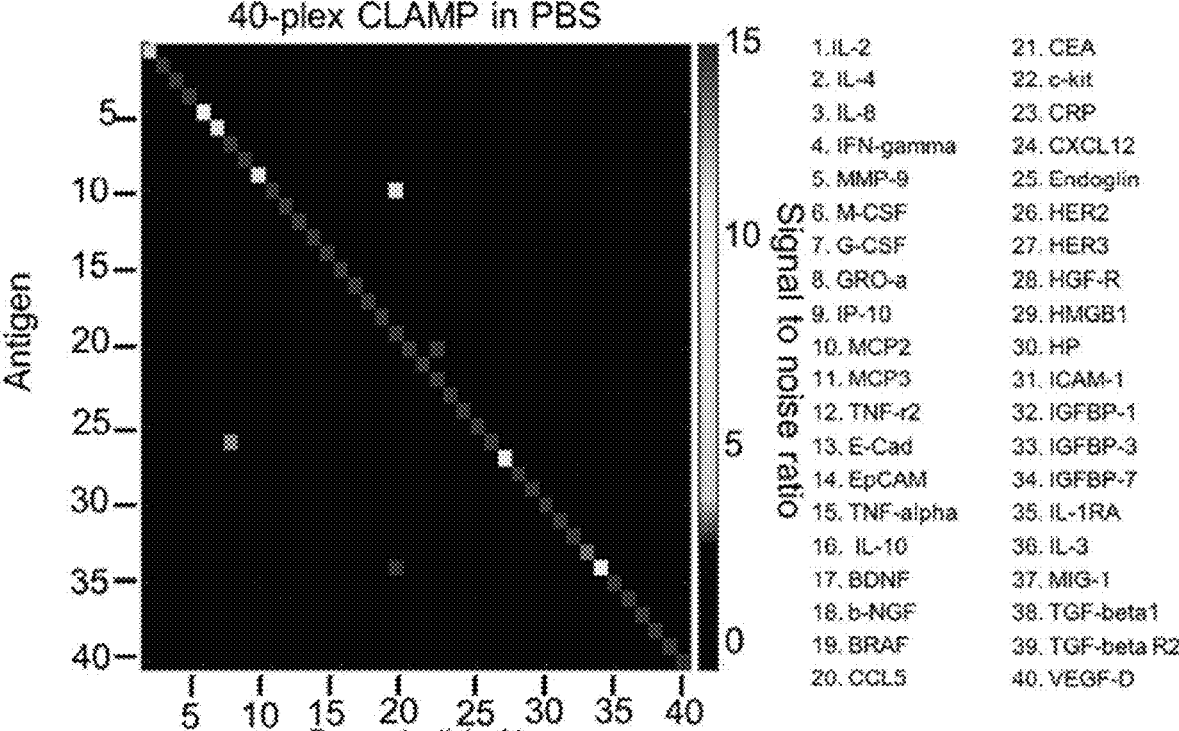
FIG. 26 shows a 40-plex specificity screening of a CLAMP assay, targeting 40 proteins (cytokines and others). Antigens (recombinant) were spiked one-by-one into buffer containing a mixture of multiplexed CLAMPs. Every well contained only one antigen. Detection, read-out, and plotting of the signal-to-noise ratio for every CLAMP for every well indicated minimal interaction of antigens with off-target CLAMPs, as shown by the minimal off-diagonal signals in the heatmap.
Figure 27:
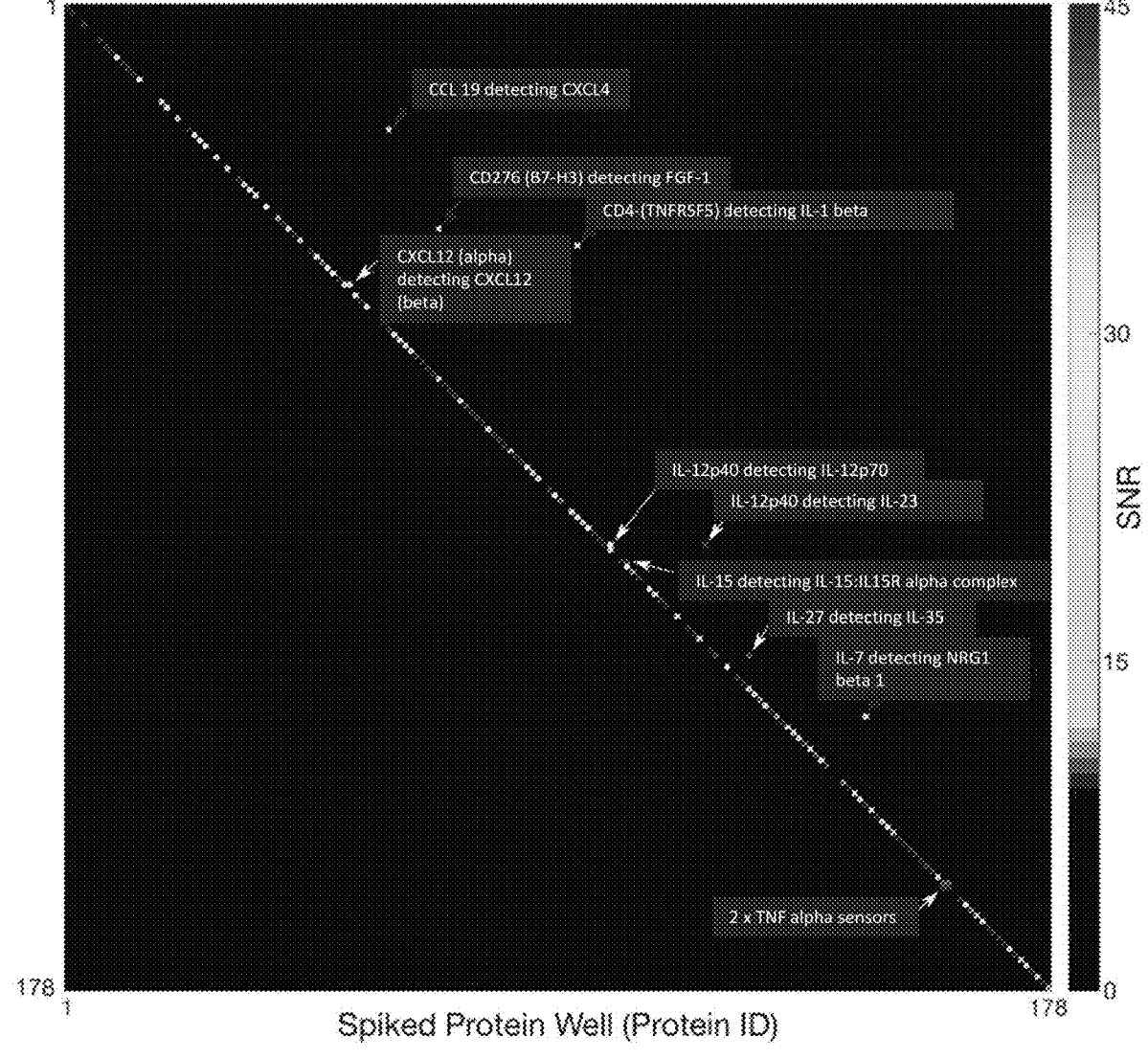
FIG. 27 shows a 178-plex specificity screening of a CLAMP assay, targeting 176 unique proteins (cytokines and others). Antigens (recombinant) were spiked one-by-one into buffer containing a mixture of multiplexed CLAMPs. Every well contained only one antigen. Detection, read-out, and plotting of the signal-to-noise ratio for every CLAMP for every well indicated minimal interaction of antigens with off-target CLAMPs, as shown by the minimal off-diagonal signals in the heatmap.
Figure 28:
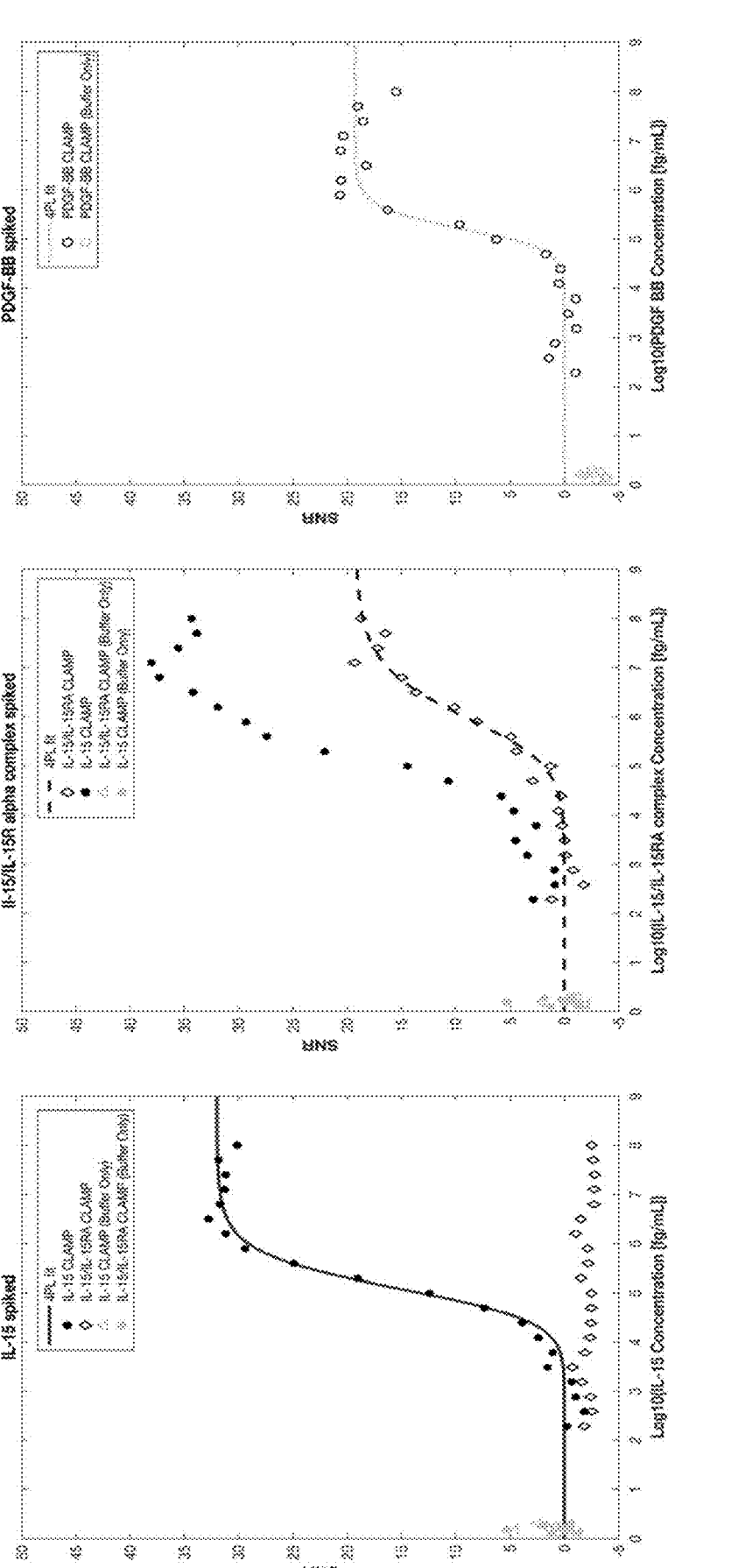
FIG. 28 demonstrates two formats of CLAMP assays for detecting protein-protein interactions. First is a protein-complex-specific CLAMP for the IL-15/IL15-R alpha complex (Middle). The IL-15/IL-15R alpha complex CLAMP was assembled using one antibody for IL-15 and another for IL-15R alpha. The same IL-15-specific antibody was also used to assemble an IL-15 CLAMP that included a second antibody specific to IL-15 protein (Left). A dilution series of IL-15 resulted in the IL-15 CLAMP increasing in signal, whereas the IL-15/IL15-R alpha complex CLAMP yielded no signal increase (Left). A dilution series of the IL-15/IL-15R alpha complex yielded a signal response in both CLAMPs, as desired (Middle). A CLAMP assembled using a DNA-conjugated protein (PDGF R beta protein) and a biotinylated PDGF-specific antibody was also used to detect PDGF-BB in the same assay (Right).

To assess cross-reactivity in multiplexed assays with higher multiplexing, a panel of 40 targets was tested, wherein mixtures of CLAMPs against 40 targets (as shown in FIG. 26) were mixed together and incubated with a single sample at high concentration (100 ng/mL) in each well. The signals seen on the diagonal indicate the specific interaction between the correct antigen and its barcoded microparticle pair. Only a few off-target signals were measureable; however, these were not due to reagent cross-reactivity. Instead, antigens were deemed to be cross-reacting with both antibodies, and hence would likely be noticeable for single-plex ELISA as well, as was demonstrated in FIG. 17.
Methods Materials and Reagents. HPLC-purified oligonucleotides were purchased from IDT (Coralville, IA, USA); the sequences and modifications are shown in FIG. 11. cAbs, antigens, and dAbs were purchased from RnD Systems (Minneapolis, MN, USA), and stored at −20° C. for up to 36 months. Streptavidin- and Protein-G magnetic MPs (M270) were purchased from Life Technologies (Carlsbad, CA, USA).

Synthesis of CLAMPs. CLAMPs were assembled on streptavidin-coated magnetic MPs with a 2.7 μm diameter (M270-Streptavidin) in two steps. The first step consisted of the immobilization of a biotinylated mixture of antibodies and oligos to functionalize the MPs and simultaneously encode them as described in detail elsewhere (Dagher, M. et al., Nature Nanotechnology, vol. 13, pp. 925-932, 2018).

Briefly, 90 pmols biotinylated oligos (COs, and SOs) and a total of 90 pmols of LOs (LO0-LO2) were mixed together in 25 μL of PBS+0.05% Tween20+300 mM NaCl (PBST0.05+NaCl300). Whereas the proportions of each L00101102 is designed to generate a unique ensemble fluorescence to define the barcode, the proportion of CO:SO allows tuning of the surface density of pulled dAb-HOs. The mixture is annealed by heating to 80 $C and cooling back to room temperature by removing the mixture from the heat source. Next, 5 μg biotinylated cAb in 17 μL of PBST0.05+NaCl300 were added to and mixed with the annealed oligonucleotide mixture. The biotinylated reagents are thereafter coimmobilized on the MPs in a single step by adding 3.25M MPs in 10 μL PBST0.05+NaCl300 and immediately mixing by pipetting. The mixture was incubated for 90 min with end-over-end mixing at room temperature, followed by 3× washing by magnetic aggregation in 150 μL PBST0.1. The barcoded and functionalized MPs were stored at 4 $C until needed. In a second step, 100,000 of the prepared MPs were mixed with the HO-containing solution (e.g. dAb-HOs) diluted in PBST0.05+NaCl300 for 30 minutes. After pulldown of HOs, the fully-assembled CLAMPs were washed 3× in PBST0.01, and were stored until the time of the assay for up to a week at 4° C.

Characterization of CLAMPs. To characterize CLAMPs, the immobilization of antibodies and oligos was confirmed by labeling using an anti-goat IgG conjugated with AlexaFluor 647 (AF647), or hybridization of a Cy5-labeled oligo (LO) targeting the HOs. The density of COs was estimated by fitting the ensemble fluorescence response of multicolour MPs using a multicolour fluorescence model, as described elsewhere (Dagher, M. et al., Nature Nanotechnology, vol. 13, pp. 925-932, 2018). To determine the expected assay background signal for a particular set of CLAMPs, the MPs were incubated with 1 μM Cy5-labeled DOs in PBST0.05+NaCl300 for one hour, followed by 3× magnetic washing in PBST0.05, and the residual signal was determined by cytometry.

Antibody oligo conjugation, purification, and characterization. Anti-uPA monoclonal antibodies were conjugated to amine-modified HOs using a hydrazone chemistry (Solulink) followed by purification according to the manufacturer's protocol. Alternatively, monoclonal antibodies were conjugated to thiol-terminated HOs using a heterobifunctional amine/thiol-reactive crosslinker. 40 μL of 30 μM thiol-modified HOs were first reduced in 200 mM dithiothreitol (DTT) in PBST at 37° C. for one hour. The reduced oligos were (i) buffer exchanged into PBS pH 7.0 using a Zeba desalting spin-column (7K MWCO, Thermo), (ii) activated for 10 min using 8 μL of 9 mM sulfosuccinimidyl 4-(N-maleimidomethyl)cyclohexane-1-carboxylate (sulfo-SMCC) dissolved in 80% PBS pH7.0 and 20% anhydrous dimethyl sulfoxide, (iii) buffer exchanged again into PBS pH 7.0 to remove excess sulfo-SMCC, and (iv) a 1-10 μL fraction (depending on the desired) reacted with 10 μL of 1 mg/mL antibodies. The reaction was left at room temperature for 1 hr and incubated overnight at 4 degrees C. thereafter. The conjugates were purified thereafter in two purification steps, an antibody and a DNA purification step, respectively.

Antibody oligo conjugation, purification, and characterization. Anti-uPA monoclonal anti bodies were conjugated to amine-modified HOs using a hydrazone chemistry (Solulink) followed by purification according to the manufacturer's protocol. Alternatively, monoclonal antibodies were conjugated to thiol-terminated HOs using a heterobifunctional amine/thiol-reactive crosslinker. 40 μL of 30 μM thiol-modified HOs are first reduced in 200 mM DTT in PBST at 37° C. for one hour. The reduced oligos were (i) buffer exchanged into PBS pH 7.0 using a Zeba desalting spin-column (7K MWCO, Thermo), (ii) activated for 10 min using 8 µL of 9 mM sulfosuccinimidyl 4-(N-maleimidom-ethyl)cyclohexane-1-carboxylate (sulfo-SMCC) dissolved in 80% PBS pH7.0 and 20% anhydrous dimethyl sulfoxide, (iii) buffer exchanged again into PBS pH 7.0 to remove excess sulfo-SMCC, and (iv) a 1-10 µL fraction (depending on the desired valency) reacted with 10 µL of 1 mg/mL antibodies. The reaction was left at room temperature for 1 hr and incubated overnight at 4° C. thereafter. The conjugates were purified in two purification steps.

Single-plex and multiplex CLAMP assay. Incubations were performed in a conical bottom 96-well plate at room temperature with horizontal shaking at 950 rpm. CLAMPs were mixed at roughly 80 MPs per barcode per µL and blocked with PBST0.05+NaCl150+0.5% BSA (PBST0.05+NaCl150+BSA0.5) for 30 min. A 25 µL aliquot of the blocked, multiplexed CLAMP mixture was added into each well and incubated with 25 µL containing the specified antigen(s) at 2× the specified concentrations in PBST0.05+NaCl150+BSA0.25, the incubation was performed for 3 hr at 950 rpm shaking. Magnetic aggregation and washing with 150 µL of PBST0.1 was repeated 4× in over a total of 30 min. Finally, detection-by-displacement is performed through the addition of 1 µM DO-Cy5 in PBST0.05+NaCl300+BSA0.25 and incubation for 1 hr with shaking, followed by 3× washing in PBST0.1.

Conventional MSA. To screen the specificity and non-specific binding in conventional MSA format, MPs were barcoded and coupled with their respective biotinylated cAbs during synthesis as described above. MP mixtures were combined to a final concentration of 2,000 MPs per barcode per assay. Incubations were performed in a conical bottom 96-well plate at room temperature with horizontal shaking at 950 rpm. Prior to incubation with assay reagents, MPs were first blocked for one hour with 1% bovine serum albumin in 0.05% Tween-20 in PBS (PBST0.05). Incubation with antigens was conducted for 120 min at the specified concentrations. BMPs were incubated with the dAb cocktail for 60 min at 2 µg/mL, followed by incubation with sAbs for 45 mins at 4 µg/mL. SNRAg was calculated by subtracting the cAb-specific mean assay background (n=6) from the MFI signals and normalizing to the global standard-deviation (i.e. across all barcodes, n=210) of the assay background.

Read-out and data analysis. MPs were read out using the FACS CANTO II cytometer by BD with blue (488 nm), red (633 nm), and violet (405 nm) lasers. In blue-laser flow cell, 530/30 and 585/42 band-pass filters were used for FAM and Cy3, respectively. In the red-laser flow cell, 660/20 band-pass filter was used for Cy5/AF647, respectively. The MPs were decoded using an automated algorithm implemented on MATLAB (Dagher, M. et al., Nature Nanotechnology, vol. 13, pp. 925-932, 2018). All data analysis was performed in MATLAB. Single-beads were distinguished from bead aggregates and other particulates by using forward and side-scatter intensities and gating was automated.

Example 10: Improved CLAMP Assay Sensitivity with Stringent Washing

A multiplexed CLAMP panel can be assembled on magnetic MPs to measure the endogenous protein levels in a complex biological sample (e.g. plasma, serum, etc). To improve the assay sensitivity, the CLAMP assay protocol can incorporate a stringent wash regiment whereby the number of wash cycles per step is doubled (increased from 4× to 8×). It can be noted that the MPs assembled with CLAMP reagents are compatible with labware used with automated liquid handling systems and ELISA plate washers. Using such instruments can increase the speed and precision of the washing steps, and the overall assay duration.

The assay protocol with stringent washing is as follows: 1) Block the surface of the MPs by incubating with a blocking buffer consisting of PBST0.05+150 mM NaCl+0.5% BSA. 2) Exchange the blocking buffer with the assay buffer (PBST0.05+0.5% BSA) by pelleting the MPs using a magnetic rack. 3) Add a 25 µL of the multiplexed CLAMP MP mixture into each well, and add 25 µL of the sample (1:1 ratio of sample to MP mixture). 4) Incubate for 3 hr at 950 rpm shaking. 5) Use magnetic aggregation to remove the sample and wash the MPs with 150 of PBST0.1, and repeated 8×. 6) After the last washing step, Add 1 µM DO-Cy5 in DO buffer (PBST0.05+NaCl300+BSA0.25) into each well and incubation for 1 hr with shaking to allow for the detection-by-displacement reaction. 7) Use magnetic aggregation to remove the DO buffer and wash the MPs with 150 µL of PBST0.1, and repeated 8×. 8) After the last wash cycle, resuspend the MP in 50 µL of PBST0.5, after which the MPs are ready for flow cytometry read-out. To identify whether the background signal improvement is due to the removal of the non-specifically bound of the constituents of the sample (due to assay wash in step 5), or the removal of unbound DO-Cy5 on the surface of the CLAMP MPs (due to DO wash in step 7), a sample of the MPs can be taken and measured before and after each washing step each antibody pair, respectively).

Example 11: No Wash CLAMP Method

In high throughput applications, such as compound screening for drug discovery, faster immunoassays with reduced numbers of steps are favored. In some embodiments, the CLAMP assays can be performed without the need for a washing protocol, while maintaining assay sensitivity and/or specificity levels. The CLAMP assay MPs assembled as shown in FIG. 6C, can be measured without the need for the final wash, as the concentration of the dye-labeled displacer on the surface of the MPs exceeds the concentration in the bulk of the solution. And hence signal measurements on any multicolour flow cytometer can be made without the interference of the dye-labeled displacer present in solution. In another embodiment shown in FIG. 6B, whereby the displacer agent is used to release hook strand oligo from the anchor strand, resulting in activation of the label attached to the hook strand. In such a construct, the assay MPs can be measured directly after the displacement reaction without the need for washing, as the concentration of the active dyes released in solution is relatively low to impose background signal during the measurement of the MPs.

Example 12: Screening for Antibody Pairing Cross Reactivity

In another embodiment, the method and assay design presented here provide rapid means for screening AB pair selectivity and sensitivity in high-throughput. It will be appreciated by those skilled in the art that screening of AB sensitivity and selectivity in immunoassays is necessary as a validation and quality assurance step. For use in a multiplexed assay, combinatorial testing is required, wherein every antibody pair is testing against every target within the multiplexed panel. However, these screens are typically performed in single-plexed assays to independently probe assays without being impacted by cross-reactivity. As such, the number of single-plex screens scales quadratically with the number of targets. For example, 400 wells are necessary to validate the selectivity of 20 AB pairs for their 20 targets, every target must tested against every other antibody pair in single-plex assays (20 wells testing target 1 against each antibody pair, respectively).

In contrast, the CLA methods and systems presented provide rapid means for testing the sensitivity and selectivity of antibody pairs. Particularly, given that sandwich immunoassays can be multiplexed without cross-reactivity, screening can be performed in parallel and at high-throughput. In the example above, only 20 wells are necessary to validate the selectivity of 20 antibody pairs for their 20 targets, wherein each target is tested against all 20 antibody pairs in multiplexed format (20 wells containing each all 20 antibody pairs, colocalized on their own CLAMP). In this example, the CLAMP approach allowed 20× more efficient AB screening; more generally, the efficiency improvement yielded by CLAMP is n*n where n is the number of targets (or AB pairs).

For example, 100 different CLAMPs can be fabricated coupled with the respective ABs to screen the sensitivity and selectivity against their respective 100 targets. In each of 100 wells, CLAMPs can be mixed at roughly 80 MPs per barcode per uL and blocked with PBST0.05+NaCl150+ 0.5% BSA for 30 mins. In each well, a purified antigen target is added at a high concentration (10 ng/mL), and the assay resumed as described before. Selective binding occurs when, in every well, only the cognate CLAMP yields a signal above noise. Off-target signal is indication of both AB pairs non-specifically binding to the off-target.

Example 13: Measurement of 50 Cytokine Levels and their Different Variants can be Performed in Multiplexed Format To measure 50 proteins and their phospho and acetylation PTM fractions, 150 CLAMP magnetic BMP mixture can be fabricated: 50 BMPs assembled using a capture AB and a detection AB against the protein of interest, 50 containing capture AB against the corresponding protein and a phoso AB, and 50 containing capture AB against the corresponding protein and a phoso AB. A 25 μL aliquot of the blocked, multiplexed CLAMP mixture can be added into each well and incubated with 25 μL containing sample in assay buffer. Following 3 hr incubation at 950 rpm shaking, magnetic aggregation and washing with 150 μL of PBST0.1 can be repeated 4× in over a total of 30 min. Finally, detection-by-displacement is performed through the addition of 1 μM DO-Cy5 in PBST0.05+NaCl300+BSA0.25 and incubation for 1 hr with shaking, followed by 3× washing in PBST0.1

Example 14: CLAMP Assay with Additional Re-Bind

In some embodiments of CLAMP using flow cytometry readout, a re-bind step can be added after the detection-by-displacement to further stabilize the assay signal. Singleplex or multiplex CLAMP beads of 25 uL can be blocked and incubated with 25 uL sample. Following 3 hr incubation at 950 rpm shaking, magnetic aggregation and washing with 150 μL of PBST0.1 can be repeated 4× in over a total of 30 min. 1 uM of displacer strand in PBST0.05+NaCl300+ BSA0.25 can be added and incubated for 1 hr with shaking, followed by 3× washing in PBST0.1. The displacer strand has the re-bind sequence on the 5' end and a Cy5 modified on the 3' end. The length of the re-bind sequence can be 20 nucleotides to ensure a stable hybridization. After the displacement the bridge strands that can bind both the anchor stand and the re-bind sequence of the displaced strand is added at the concentration of 1 uM, followed by 1 hr incubation with shaking and final 3× washing in PBST0.1. Due to the re-bind step, the fluorescent signal from an analyte binding event is stabilized by having the fluorescent labelled displacer tethered to the support via DNA hybridization which has lower off-rate compared to the antibody-analyte binding. When using the same displacer strand in a multiplexed assay, the same re-bind sequence ensures the signal stability is consistent across all analytes. The flow cytometry measurement can be carried out in a few hours or days later finishing the assay which offer convenience in the logistics of a high throughput assay.

Example 15: CLAMP Assay Signal Amplification Using BV-421 Dye

In some embodiments of CLAMP using flow cytometry readout, polymer-based fluorescent dye BV421 can be conjugated to the displacer. Singleplex or multiplex CLAMP beads of 25 uL can be blocked and incubated with 25 uL sample. Following 3 hr incubation at 950 rpm shaking, magnetic aggregation and washing with 150 μL of PBST0.1 can be repeated 4× in over a total of 30 min. The BV421 conjugated displacer is then added in the detection-by-displacement step. 1 uM of displacer strand in PBST0.05+ NaCl300+BSA0.25 and incubation for 1 hr with shaking, followed by 3× washing in PBST0.1. The fluorescent signal of BV421 is then measured in the flow cytometry measurements. Due to the high quantum yield, photostability and low background of the polymer-based fluorescent dye, the signal to noise ratio is improved compared to commonly used Cy5 conjugated displacer in the same CLAMP assay. The expanded range of fluorescent intensity offers higher sensitivity and accuracy using the same CLAMP format. FIG. 36 shows the effects of BV421 on increasing the dynamic range of detection.

Example 16: Quality Control (QC) of CLAMP Barcoded Microparticles

In some embodiments, a set of reagents referred to as "quality control" reagents or "QC", are designed to bind and label the different elements of the CLAMP structure, whereby validating the presence and functionality of each of the elements of the CLAMP reagents. QC is used to validate and maintain reproducibility in the fabrication process, and can be used as control during a CLAMP assay to verify the mechanisms of signal transduction. The QC reagents may consist of, but not limited to the following: (1) A labeled antibody specific to the species of the capture AB immobilized on the surface, (2) A labeled antibody specific to the species of the detection AB conjugated to the hook strand, and is tethered to the surface be hybridization onto the capture strand. (3) A labeled oligonucleotide (referred to as LO), designed to hybridize specifically onto the hook strand. The signal obtained from the QC reagents are used to determine whether the fabrication process has yielded CLAMP structures that are suitable for usage in assay. In such QC, the ratio of the signal between the detection AB QC and capture AB QC, provides an estimate of the total number of potential sandwich CLAMP assay sites. Another QC is the ratio of signal between the LO and the detection AB, which provides an indication of the valency of the hook strand to the detection AB (i.e. number of oligos conjugated to one antibody). As such, a high ratio in this QC could indicate a high background noise level for the CLAMP.

For the measurement of the levels of 50 cytokines, 50 CLAMP magnetic BMPs are fabricated. For each BMP, target specific AB pairs are arranged on the surface, such that a biotinylated goat-anti-human capture AB is immobilized on the surface, and a mouse-anti-human detection AB, conjugated to the HO is hybridized onto the CO on the surface of the BMP. To confirm the presence and functionality of each element of the CLAMP, QC can be done on the BMP. QC reagents include, a Cy5 labeled oligo (LO) that is complementary to the H to measure detect the density of the HO, a Cy5 labeled anti-mouse AB to detect the levels of the detection AB, and CY5 labeled anti-goat AB to measure the density of capture AB on the surface of the CLAMP BMPs. A 25 μL aliquot of the blocked, multiplexed CLAMP mixture can be added into 3 wells different wells, and incubated with 25 μL containing each of the QC reagents diluted in the assay buffer (PBST0.05+0.5% BSA). Following 3 hr incubation at 950 rpm shaking, magnetic aggregation and washing with 150 μL of PBST0.1 can be repeated 4× in over a total of 30 min. After the last wash cycle, resuspend the MP in 50 μL of PBST0.5, after which the MPs are ready for flow cytometry read-out.

Example 17: CLAMP Assay Signal Amplification Using Hybridization Chain Reaction (HCR)

In some embodiments of CLAMP using flow cytometry readout, HCR amplification methods can be added after the displacement to improve the higher signal gain. A 36 nt HCR initiating label sequence can be included in the displacer strand. 25 μL of blocked singleplex or multiplex CLAMP beads can be incubated with 25 μL of sample. Following 3 hr incubation at 950 rpm shaking, magnetic aggregation, and washing with 150 μL of PBST0.1 that can be repeated 4× in over a total of 30 min. Cy5 conjugated to the displacer oligos is used in the detection-by-displacement step, whereby 40 μL of 1 uM of the Cy5-DO in PBST0.05+NaCl300+ BSA0.25 and incubation for 1 hr with shaking, followed by 3× washing in PBST0.1. After the displacement, a pair of kinetically trapped 72 nt HCR hairpins H1 and H2 can be added to the reaction at the concentration of 1 uM in PBST0.05+NaCl300+BSA0.25. Both H1 and H2 is modified with Cy5. The initiator label in the displacer open up H1 by partially hybridise to it which left the rest of H1 available to open up and hybridise to H2. The opened H2 is in turns open up and hybridise to H1. The chain reaction alternates H1 and H2 to hybridise into an amplification polymer. The HCR reaction can be incubated for 1 hr with shaking, followed by 3× washing in PBST0.1. This amplification can yield a 5 to 10 fold increase in fluorescence intensity signal.

Example 18: Fabrication of CLAMP Sensors for Multiplexed Detection of SARS-CoV-2 Antibodies In some embodiments, the multiplexed assay system was implemented on spectrally-encoded beads, wherein a one-pot bead barcoding strategy and automated decoding method can be used in methods and systems provided herein. Examples of such barcoding/decoding methods are described in U.S. patent application Ser. No. 16/153,071 and in Dagher, M. et al., Nature Nanotechnology, vol. 13, pp. 925-932, 2018, the contents of each of which are incorporated by reference herein in their entirety. Such methods use accurate models of fluorophore spectral overlap and multi-color Forster-resonance energy transfer (FRET). In some embodiments of multiplexed serological assays measuring antibodies targeting several targets of a specific viral strain, for example SARS-CoV-2. Each of the Virus specific antigens and fragments including spike protein (S), nucleocapsid protein (N), envelope protein (E), spike protein S1/S2/RBS domains, are tethered to the surface of separate and barcoded magnetic particles. The same manufacturing workflows were used to build multiplex serological assay as described herein. Namely, in a first step, streptavidin beads at a concentration of 400 k/uL were incubated with biotinylated antigen and biotinylated anchor and/or capture oligos modified with different dyes to yield a distinguishable barcode. Each barcode, and antigen, were incubated in separate tubes at room temperature for one and half hours, followed by washing using 400 uL of 1×PBS, 0.1% tween20. The washing step was repeated three times to remove any excess biotinylation reagents. In a second step, the same antigen modified via conjugation to a hook oligo was added to the corresponding functionalized beads from the first step. The hook oligo was complementary to the anchor strand oligo and hybridized to it, resulting in the assembly of colocalized antigens. Each barcode and corresponding conjugate were incubated in separate tubes. Incubation in the second step was carried out at four degrees for ten hours, followed by washing using 400 uL of 1×PBS, 0.1% tween20. The washing step was repeated three times to remove any excess conjugates. The beads can be separately stored for use at a later time.

Example 19: Multiplexed Detection of SARS-CoV-2 Antibodies Using CLAMP

In a CLAMP assay SARS-CoV-2, 25 uL singleplex or multiplex barcoded magnetic beads were blocked and incubated with 25 uL of plasma or serum samples. The incubation plate was kept on an orbital plate shaker at 950 rpm for 3 hours at room temperature, followed by washing with 100 μL of 1×PBS, 0.1% tween 20. The washing step was repeated three times. The beads were reconstituted into 30 uL in the washing buffer after washing steps. 30 uL displacer oligo (DO) conjugated to Cy5 was then added to each well, followed by 30 min incubation on a plate shaker at 950 rpm at room temperature. As a result, the hook oligo which originally hybridized to the capture oligo were displaced from the surface and hybridized to DO-Cy5 oligo. After displacement, 1×PBS, 0.1% tween 20 was used to wash the plate for 3 times before the cytometry readout.

Example 20: Re-Bind to Stabilize and Record the Analyte Quantities in a Sample In some embodiments, a 'bind back' reagent can be added to the packaged test kit to further simplify protocol for the end user. The protocol includes: thaw plate for 30 min on ice, add unknown samples in the wells. Following the sample incubation, wash the plate 4 times with 100 uL PBST0.1 and add unlabeled displacing reagent. After displacing, the user adds a 'bind back' reagent that enables the displaced hook oligo to bind back to the beads surface to minimize signal loss before measurements. The 'bind back' reagent can be a DNA oligo that is partially complementary to the displacing oligo and the capture oligo on the surface, such as 'GTCCGATCAACAGCCC CATAAACTCT-CAATAACCAAT' (SEQ ID NO: 1). The test plate can then be frozen and sent to the facilitated lab for a scheduled 5 readout that is no longer time sensitive. Before the scheduled measurements, thaw the plate for 30 min on ice, add in a labeled DNA oligo that is partially complementary to the displacer. Following a 30 min incubation, wash the plate 4 times with 100 uL PBST0.1 and then read on a flow 10 cytometer.

While the present disclosure has been described in connection with specific embodiments thereof, it will be understood that it is capable of further modifications and this application is intended to cover any variations, uses, or adaptations, including such departures from the present disclosure as come within known or customary practice within the art to and as may be applied to the essential features hereinbefore set forth, and as follows in the scope of the appended claims.

The contents of all documents and references cited herein are hereby incorporated by reference in their entirety.

---

What is claimed is:

1. A method for detecting and quantifying an analyte within a sample, the method comprising:

(a) contacting the sample with colocalization-by-linkage (CLA) structure that comprises:

(i) a support, (ii) a capture agent attached to the support;

(iii) a detection agent anchor polynucleotide attached to the support, wherein the anchor polynucleotide comprises an anchor sequence and a releasable barcode sequence attached to the support; and (iv) a detection agent linked to a hook polynucleotide that comprises a detection barcode sequence and an anchor-binding sequence complementary to at least a portion of the anchor sequence, wherein the detection agent is releasably bound to the detection agent anchor polynucleotide;

(b) adding a detectably-labeled displacement agent that binds the hook polynucleotide and releases the detection agent and the hook polynucleotide from the detection agent anchor polynucleotide;

(c) detecting the presence or absence of the detectably-labeled displacement agent indicating the presence or absence of the detection agent bound to the analyte;

(d) hybridizing, annealing, or ligating the detection barcode and the releasable barcode to generate a CLA barcode; and (e) identifying and/or processing the CLA barcode.

2. The method of claim 1, further comprising partitioning the CLA structure after (c).

3. The method of claim 1, wherein the detection barcode is releasable from the detection agent.

4. The method of claim 1, wherein the detection barcode identifies the detection agent.

5. The method of claim 1, wherein the releasable barcode identifies the capture agent.

6. The method of claim 1, wherein the releasable barcode identifies the analyte.

7. The method of claim 1, wherein the releasable barcode identifies the capture agent and the analyte.

8. The method of claim 1, wherein identifying the CLA barcode is performed by a sequencing reaction.

9. The method of claim 1, wherein identifying the CLA barcode is performed by a hybridization reaction.

10. The method of claim 1, wherein identifying the CLA barcode is performed by a PCR reaction.

11. A method for amplifying a colocalization-by-linkage (CLA) signal, the method comprising:

(a) contacting the sample with CLA structure that comprises:

(i) a capture agent attached to a support;

(ii) a detection agent anchor polynucleotide attached to the support, wherein the anchor polynucleotide comprises an anchor sequence and a releasable barcode sequence attached to the support; and (iii) a detection agent linked to a hook polynucleotide that comprises a detection barcode sequence and an anchor-binding sequence complementary to at least a portion of the anchor sequence, wherein the detection agent is releasably bound to the detection agent anchor polynucleotide;

(b) adding a detectably-labeled displacement agent that comprises a Hybridization Chain Reaction (HCR) imitating label and binds the hook polynucleotide and releases the detection agent and the hook polynucleotide from the detection agent anchor polynucleotide;

(c) adding a labeled HCR hairpin to the product of (b); and (d) detecting the presence or absence of the detectably-labeled displacement agent indicating the presence or absence of the detection agent bound to the analyte.

\*   \*   \*   \*   \*